(12) United States Patent
Danopoulos

(10) Patent No.: US 11,883,359 B2
(45) Date of Patent: *Jan. 30, 2024

(54) ADAPTER FOR USE IN A PLANETARY MIXER

(71) Applicant: MEDISCA PHARMACEUTIQUE INC., St-Laurent (CA)

(72) Inventor: Panagiota Danopoulos, St-Laurent (CA)

(73) Assignee: MEDISCA PHARMACEUTIQUE INC., Saint-Laurent (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/123,442

(22) Filed: Dec. 16, 2020

(65) Prior Publication Data

US 2021/0186808 A1    Jun. 24, 2021

Related U.S. Application Data

(63) Continuation of application No. 16/372,006, filed on Apr. 1, 2019, now Pat. No. 10,993,876, which is a
(Continued)

(51) Int. Cl.
    *B01F 3/12*      (2006.01)
    *B04B 15/02*      (2006.01)
    (Continued)

(52) U.S. Cl.
    CPC . *A61J 1/05* (2013.01); *A61J 3/04* (2013.01); *A61K 9/0034* (2013.01); *A61K 9/06* (2013.01);
    (Continued)

(58) Field of Classification Search
None
See application file for complete search history.

(56) References Cited

U.S. PATENT DOCUMENTS 947,922 A    2/1910    Lewis
1,059,947 A    4/1913    McHenry
(Continued)

FOREIGN PATENT DOCUMENTS

BR    112019009594    10/2019
CA    1246053 A    12/1988
(Continued)

OTHER PUBLICATIONS

International Search Report dated Feb. 6, 2018 in connection with International Patent Application No. PCT/CA2017/051350, 3 pages.
(Continued)

*Primary Examiner* — P. Kathryn Wright
(74) *Attorney, Agent, or Firm* — Finnegan, Henderson, Farabow, Garrett & Dunner LLP

(57) ABSTRACT

A dispensing container and adapter system for use with a planetary mixer is disclosed. The dispensing container has a longitudinal axis and a transverse axis. The dispensing container may include a nozzle and a removable cap to cover the nozzle. The removable cap may have a first width dimension measured along the transverse axis. The dispensing container may include a body having a second width dimension measured along the transverse axis. An adapter may receive the dispensing container. The adapter may include a cavity to receive the removable cap. The cavity may have a cavity width that exceeds the first width dimension. The adapter may also include a recess for receiving a portion of the dispensing container. The recess may extend from the cavity. At least a portion of the recess may have a width dimension smaller than both the first width dimension and the second width dimension.

20 Claims, 36 Drawing Sheets

Related U.S. Application Data continuation of application No. 16/131,986, filed on Sep. 14, 2018, now Pat. No. 10,420,705, which is a continuation of application No. 15/809,636, filed on Nov. 10, 2017, now Pat. No. 10,231,903.

(60) Provisional application No. 62/420,426, filed on Nov. 10, 2016.

(51) Int. Cl.

| | | |
|---|---|---|
| *A61J 1/05* | (2006.01) | |
| *B65B 7/16* | (2006.01) | |
| *A61K 47/10* | (2017.01) | |
| *A61K 9/06* | (2006.01) | |
| *A61K 31/197* | (2006.01) | |
| *A61K 31/045* | (2006.01) | |
| *A61K 33/14* | (2006.01) | |
| *A61K 31/7048* | (2006.01) | |
| *A61K 31/565* | (2006.01) | |
| *A61K 9/107* | (2006.01) | |
| *A61K 9/00* | (2006.01) | |
| *A61K 47/46* | (2006.01) | |
| *A61K 31/192* | (2006.01) | |
| *A61K 31/196* | (2006.01) | |
| *A61K 31/4418* | (2006.01) | |
| *A61K 47/38* | (2006.01) | |
| *A61K 47/26* | (2006.01) | |
| *A61K 31/4458* | (2006.01) | |
| *A61K 31/137* | (2006.01) | |
| *A61K 31/57* | (2006.01) | |
| *A61K 47/42* | (2017.01) | |
| *A61K 31/135* | (2006.01) | |
| *A61K 31/195* | (2006.01) | |
| *A61K 31/351* | (2006.01) | |
| *A61K 31/4422* | (2006.01) | |
| *A61K 31/445* | (2006.01) | |
| *A61J 3/04* | (2006.01) | |
| *B01F 29/10* | (2022.01) | |
| *B01F 29/32* | (2022.01) | |
| *B01F 29/00* | (2022.01) | |
| *B01F 31/00* | (2022.01) | |
| *B01F 35/42* | (2022.01) | |
| *B01F 35/22* | (2022.01) | |

(52) U.S. Cl.
CPC ............ *A61K 9/107* (2013.01); *A61K 31/045* (2013.01); *A61K 31/135* (2013.01); *A61K 31/137* (2013.01); *A61K 31/192* (2013.01); *A61K 31/195* (2013.01); *A61K 31/196* (2013.01); *A61K 31/197* (2013.01); *A61K 31/351* (2013.01); *A61K 31/445* (2013.01); *A61K 31/4418* (2013.01); *A61K 31/4422* (2013.01); *A61K 31/4458* (2013.01); *A61K 31/565* (2013.01); *A61K 31/57* (2013.01); *A61K 31/7048* (2013.01); *A61K 33/14* (2013.01); *A61K 47/10* (2013.01); *A61K 47/26* (2013.01); *A61K 47/38* (2013.01); *A61K 47/42* (2013.01); *A61K 47/46* (2013.01); *B01F 29/10* (2022.01); *B01F 29/32* (2022.01); *B01F 29/40* (2022.01); *B01F 29/401* (2022.01); *B01F 31/00* (2022.01); *B01F 35/2209* (2022.01); *B01F 35/421* (2022.01); *B65B 7/16* (2013.01); *B01F 29/40365* (2022.01)

(56) References Cited

U.S. PATENT DOCUMENTS

| | | | |
|---|---|---|---|
| 1,101,351 | A | 6/1914 | Suit |
| 1,998,692 | A | 4/1935 | Rossem et al. |
| 2,728,494 | A | 12/1955 | Hobson |
| 3,029,187 | A | 4/1962 | Steinhardt et al. |
| 3,164,303 | A | 1/1965 | Trautmann |
| 3,470,927 | A | 10/1969 | Craig |
| 3,778,033 | A | 12/1973 | Pullman |
| 4,114,803 | A | 9/1978 | Romanuauskas |
| 4,323,492 | A | 6/1982 | Zimmerman et al. |
| 4,497,581 | A | 2/1985 | Miller |
| 4,900,159 | A | 2/1990 | Jamison |
| 4,966,468 | A | 10/1990 | Brüning |
| 5,238,304 | A | 8/1993 | Zimmermann |
| 6,099,160 | A * | 8/2000 | Flackett ............ B01F 15/00824 366/217 |
| 6,634,576 | B2 | 10/2003 | Verhoff et al. |
| 6,755,565 | B2 | 6/2004 | Flackett |
| 7,213,994 | B2 | 5/2007 | Phipps et al. |
| 7,438,460 | B2 | 10/2008 | Schmidt et al. |
| 8,191,729 | B2 | 6/2012 | Deusser et al. |
| 8,360,629 | B2 | 1/2013 | Globerman et al. |
| 8,408,418 | B2 | 4/2013 | Kuzelka |
| 8,845,180 | B2 | 9/2014 | Huckby |
| 8,945,606 | B2 | 2/2015 | Haley |
| 8,950,929 | B2 | 2/2015 | Globerman et al. |
| 9,043,019 | B2 | 5/2015 | Eliuk et al. |
| 9,259,696 | B2 | 2/2016 | Globerman et al. |
| 10,231,903 | B2 | 3/2019 | Danopoulos et al. |
| 10,420,705 | B2 | 9/2019 | Danopoulos et al. |
| 10,631,906 | B2 | 4/2020 | Globerman et al. |
| 10,765,600 | B2 | 9/2020 | Danopoulos et al. |
| 10,766,047 | B2 | 9/2020 | Wong et al. |
| 10,874,489 | B2 | 12/2020 | Pierson et al. |
| 10,993,876 | B2 | 5/2021 | Danopoulos et al. |
| 11,090,224 | B2 | 8/2021 | Danopoulos et al. |
| 11,096,864 | B2 | 8/2021 | Danopoulos et al. |
| 2002/0012701 | A1 | 1/2002 | Kolter et al. |
| 2002/0136089 | A1 | 9/2002 | Folestad et al. |
| 2003/0142583 | A1 | 7/2003 | Santospago et al. |
| 2003/0179646 | A1 | 9/2003 | Miller |
| 2003/0198126 | A1* | 10/2003 | Flackett ................ B01F 9/0032 366/217 |
| 2004/0211747 | A1 | 10/2004 | Whitley |
| 2004/0265344 | A1 | 12/2004 | Zolotariov |
| 2006/0105022 | A1 | 5/2006 | Yokokawa et al. |
| 2006/0108318 | A1 | 5/2006 | Chisholm |
| 2006/0175443 | A1 | 8/2006 | Bysouth |
| 2007/0002680 | A1 | 1/2007 | Vanderbilt et al. |
| 2007/0002681 | A1 | 1/2007 | Vanderbilt et al. |
| 2007/0002682 | A1 | 1/2007 | Vanderbilt et al. |
| 2007/0025180 | A1 | 2/2007 | Ishii |
| 2007/0140049 | A1 | 6/2007 | Johnson et al. |
| 2007/0280038 | A1 | 12/2007 | Schmidt et al. |
| 2008/0212405 | A1 | 9/2008 | Globerman et al. |
| 2009/0040865 | A1 | 2/2009 | Benjamin, II |
| 2009/0163860 | A1* | 6/2009 | Patrick .................. G16H 20/17 604/83 |
| 2009/0196119 | A1 | 8/2009 | Greco et al. |
| 2010/0265791 | A1 | 10/2010 | Ishii |
| 2012/0135047 | A1 | 5/2012 | Dodd et al. |
| 2012/0135846 | A1 | 5/2012 | Yao et al. |
| 2012/0269029 | A1 | 10/2012 | Konietzko et al. |
| 2012/0307586 | A1 | 12/2012 | Globerman et al. |
| 2013/0121105 | A1 | 5/2013 | Denize et al. |
| 2013/0261188 | A1 | 10/2013 | Hibi et al. |
| 2015/0336712 | A1 | 11/2015 | Taheri |
| 2016/0235459 | A1 | 8/2016 | Globerman et al. |
| 2016/0251121 | A1 | 9/2016 | Hadar et al. |
| 2016/0262421 | A1 | 9/2016 | Biglari et al. |
| 2018/0125753 | A1 | 5/2018 | Danopoulos et al. |
| 2018/0345305 | A1 | 12/2018 | Wong et al. |
| 2018/0353919 | A1* | 12/2018 | LaRose .................. B01F 29/10 |
| 2019/0008723 | A1 | 1/2019 | Danopoulos et al. |
| 2019/0224073 | A1 | 7/2019 | Danopoulos et al. |
| 2020/0054522 | A1 | 2/2020 | Danopoulos et al. |

(56) References Cited

U.S. PATENT DOCUMENTS

| | | | |
|---|---|---|---|
| 2020/0345581 A1 | 11/2020 | Danopoulos et al. | |
| 2020/0345582 A1 | 11/2020 | Danopoulos et al. | |
| 2021/0086150 A1 | 3/2021 | Danopoulos et al. | |

FOREIGN PATENT DOCUMENTS

| | | |
|---|---|---|
| CA | 2352874 A1 | 8/2006 |
| CA | 3062126 C | 5/2018 |
| DE | 19855440 A1 | 8/2000 |
| DE | 102008039745 A1 | 3/2009 |
| EP | 0599783 B1 | 8/1998 |
| EP | 1559438 | 8/2005 |
| ES | 2317611 T3 | 4/2009 |
| JP | 2002320835 | 11/2002 |
| JP | 2006305512 | 11/2006 |
| JP | 3977918 B2 | 9/2007 |
| JP | 2008-531572 A | 8/2008 |
| JP | 2009208026 | 9/2009 |
| JP | 2015-500334 A | 1/2015 |
| JP | 2015027676 A | 2/2015 |
| JP | 2016-523950 A | 8/2016 |
| WO | WO 2012/133492 A1 | 4/2012 |

OTHER PUBLICATIONS

Written Opinion dated Feb. 6, 2018 in connection with International Patent Application No. PCT/CA2017/051350, 4 pages.
Non-Final Office Action dated Apr. 10, 2018 in connection with U.S. Appl. No. 15/809,636, 19 pages.
Non-Final Office Action dated Dec. 10, 2018 in connection with U.S. Appl. No. 16/131,986, 18 pages.
Restriction Requirement dated May 24, 2019 in connection with U.S. Appl. No. 16/372,006, 6 pages.
Examiner's Report dated Jul. 25, 2019 in connection with Canadian Patent Application No. 3,043,494, 3 pages.
Non-Final Rejection issued on USPTO dated Aug. 15, 2019 in connection with U.S. Appl. No. 16/372,006, 17 pages.
Non-Final Office Action dated Dec. 9, 2019 in connection with U.S. Appl. No. 16/662,423, 15 pages.
Examiner's Report dated Dec. 13, 2019 in connection with Canadian Patent Application No. 3,043,494, 4 pages.
Final Office Action dated Dec. 16, 2019 in connection with U.S. Appl. No. 16/372,006, 19 pages.
Examiner's Report dated Feb. 6, 2020 in connection with Canadian Patent Application No. 3,062,126 3 pages.
Examiner's Report dated Feb. 12, 2020 in connection with Canadian Patent Application No. 3,043,494, 5 pages.
Advisory Action and Applicant-initiated Interview Summary dated Mar. 26, 2020 in connection with U.S. Appl. No. 16/372,006, 9 pages.
Notice of Allowance dated Apr. 10, 2020 in connection with U.S. Appl. No. 16/662,423, 14 pages.
Supplementary European Search Report dated Apr. 23, 2020 in connection with European Patent Application No. 17 86 8979, 2 pages.
Extended European Search Report dated May 6, 2020 in connection with European Patent Application No. 17 86 8979, 4 pages.
Restriction Requirement dated Aug. 7, 2020 in connection with U.S. Appl. No. 16/932,313, 7 pages.
Restriction Requirement dated Aug. 7, 2020 in connection with U.S. Appl. No. 16/932,171, 7 pages.
Office Action dated Aug. 12, 2020 in connection with U.S. Appl. No. 16/372,006, 25 pages.
Examiner's Report dated Oct. 23, 2020 in connection with Canadian Patent Application No. 3062126, 3 pages.
Applicant-initiated Interview summary dated Oct. 26, 2020 in connection with U.S. Appl. No. 16/372,006, 12 pages.
Esezobo S. et al., "Moisture and gelatin effects on the interparticle attractive forces and the compression behaviour of oxytetracycline formulations" 7 pages (Year: 1977).
English translation of Suzuki et al. JP 2002-320835 (Year: 2002)).
English translation of Thinky Corp et al. (JP 2009-208026) (Year: 2009).
Karim A.A. et al., Food Hydrocolloids, 23, pp. 563-576 (Year: 2009).
Intertronics, THINKY An Introduction to Planetary Centrifugal Mixers, obtained online at: http://www.intertronics.co.uk/wp-content/uploads/2017/04/getting_to_know_thinky_mixers.pdf, pp. 1-26. (Year: 2009).
Intertronics, THINKY An inlioduction to Planetary Centrifugal Mixers, obtained online at https://www.intertronics.co.uk/wp-content/uploads/2017/04/getting_to_know_mixers.pdf, pp. 1-26 (Year:2011).
Ice.edu, Taste Test: Fluid Gels, obtained online at: https://www.ice.edu/blog/taste-test-fluid-gels, pp. 1-5 (Year:2012).
USP on Compounding, A Guide for the Compounding Practitioner—2014, Nov. 2013, (375 pages).
Miyazaki et al., "A novel blending method for dispensing powered medicine", Chem. Pharm. Bull., 2014, vol. 62, Issue 1, pp. 54-57.
Keiichi, Hori "User interview—Prosessor Keiichi hori JAXA", Thinky Library, obtained at: https://www.thinkymixer.com/en-gl/library/interview/user-interview-professor-keiichi-hori-jaxa/ Jul. 14, 2016.
Screen Captures from YouTube video clip entitled "Planetary Centrifual Mixer ARE 310" obtained at https://www.youtube.com/watch?v=flMHXrfWYfM.
Notice of Allowance dated Apr. 10, 2020 in connection with U.S. Appl. No. 16/662,423, 16 pages.
Applicant-initiated Interview Summary dated Apr. 2, 2021, in connection with U.S. Appl. No. 16/932,171, 2 pages.
Examiner Report dated May 21, 2021, in connection with Canadian Patent Application No. 3,043,494, 3 pages.
Examiner's Report dated Mar. 5, 2021, in connection with Canadian patent application No. 3,106,928, 4 pages.
Examiner's Report dated Feb. 5, 2021, in connection with Canadian patent application No. 3,043,494, 4 pages.
Examiner's Report dated May 10, 2021, in connection with Canadian patent application No. 3,106,934, 4 pages.
Notice of Allowance dated Jan. 21, 2021, in connection with U.S. Appl. No. 16/372,006, 18 pages.
Notice of Allowance dated Jun. 7, 2021, in connection with U.S. Appl. No. 16/932,313, 7 pages.
Notice of Allowance dated May 13, 2021, in connection with U.S. Appl. No. 16/932,171, 5 pages.
Office Action dated Feb. 24, 2021, in connection with European Patent Application No. 17868979.0, 6 pages.
Office Action dated Jun. 2, 2021, in connection with U.S. Appl. No. 17/123,400, 16 pages.
Office Action dated Mar. 29, 2021, in connection with U.S. Appl. No. 16/932,171, 7 pages.
Office Action dated Mar. 4, 2021, in connection with U.S. Appl. No. 16/932,313, 21 pages.
Office Action dated Mar. 9, 2021, in connection with U.S. Appl. No. 16/932,171, 12 pages.
Restriction Requirement dated May 12, 2021, issued in connection with U.S. Appl. No. 17/123,400, 5 pages.
Examiner's report dated Jul. 22, 2021, in connection with Canadian Patent Application No. 3,106,928, 3 pages.
Examiner's Report dated Nov. 4, 2021, in connection with CA patent application No. 3,131,133—5 pages.
Examiner's Report dated Nov. 9, 2021, in connection with CA patent application No. 3,106,934—6 pages.
Examiner's Report dated Dec. 2, 2021, in connection with CA patent application No. 3,131,129—6 pages.
Office Action dated Oct. 12, 2021, in connection with Japanese patent application No. 2019-524437—6 pages (+ English translation, 8 pages).
Final Office Action dated Dec. 10, 2021, in connection with U.S. Appl. No. 17/123,400 (7 pages).
Communication under Rule 71 (3) EPC dated Apr. 5, 2022, in connection with EP patent application No. 17 868 979.0 (7 pages).
Notice of Allowance dated Apr. 7, 2022, in connection with CA patent application No. 3,106,928 (1 page).

(56) References Cited

OTHER PUBLICATIONS

Examiner's Report dated May 3, 2022, in connection with CA patent application 3131129 (4 pages).
Notice of Allowance dated Apr. 27, 2022, in connection with CA patent application 3043494 (1 page).
Examiner's Report dated May 4, 2022, in connection with CA patent application 3131133 (4 pages).
A novel Blending Method for Dispensing Powdered Medicine—Chem Pharm Bull 62(1) 54-57 (2014)—(4 pages).
Chen et al., "Nanonization Strategies for Poorly Water-Soluble Drugs," Drug Discovery Today, vol. 16, Nos. 7/8; Apr. 2011; 7 pages.
Food and Drug Administration; Draft "Guidance for Industry Powder Blends and Finished Dosage Units—Stratified In-Process Dosage Unit Sampling and Assessment"; Oct. 2003; 18 pages.
Hiseman et al., "Granular Flow in a Planetary Mixer," Institution of Chemical Engineers, Trans IChemE; vol. 80, Part A, Jul. 2002, 9 pages.
Mehrotra et al., "Comparing Mixing Performance of Uniaxial and Biaxial Bin Blenders," Powder Technology 196 (2009), 7 pages.
Niwa et al., "Novel Technology to Prepare Oral Formulations for Preclinical Safety Studies," International Journal of Pharmaceutics 350 (2008), 9 pages.
Niwa et al., "Universal Wet-Milling Technique to Prepare Oral Nanosuspension Focused on Discovery and Preclinical Animal Studies—Development of Particle Design Method," International Journal of Pharmaceutics 405 (2011), 10 pages.
Sawant et al., "Drug Nanocrystals: Novel Technique for Delivery of Poorly Soluble Drugs," International Journal of Science Innovations and Discoveries, vol. 1, Issue 3, Nov.-Dec. 2011, 15 pages.
Takatsuka et al., "Nanosizing of Poorly Water Soluble Compounds Using Rotation/Revolution Mixer," Chem. Pharm. Bull. 57(10); Oct. 2009; 7 pages.
Yin, Trudy; "A Guide to Blend Uniformity," Journal of GXP Compliance, vol. 12, No. 1, Oct. 2007, 6 pages.
"Pursuing a Bright Future With Mixing Technology"; Thinky; final page of document lists "Apr. 2016"; (8 pages).
"Pioneering Planetary Centrifugal Mixers"; Thinky Mixer Series; final page of document lists "Oct. 2010" (32 pages).
Thinky Mixer ARE-310 Instruction Manual; "Planetary Centrifugal Mixer"; Thinky Corporation; p. 65 of document lists "Issued Nov. 7, 2008" and "Revised Aug. 18, 2010" (66 pages).

* cited by examiner

ADAPTER FOR USE IN A PLANETARY MIXER

CROSS-REFERENCE TO RELATED APPLICATIONS

The present application is a continuation application of and claims the benefit of priority to U.S. patent application Ser. No. 16/372,006 filed on Apr. 1, 2019, which is a continuation application of and claims the benefit of priority to U.S. patent application Ser. No. 16/131,986 filed on Sep. 14, 2018 (now U.S. Pat. No. 10,420,705), which is a continuation application of and claims the benefit of priority to U.S. patent application Ser. No. 15/809,636 filed on Nov. 10, 2017 (now U.S. Pat. No. 10,231,903), which claims the benefit of priority to U.S. Provisional Patent Application No. 62/420,426 filed on Nov. 10, 2016, the contents of all of which are incorporated herein by reference in their entirety.

TECHNICAL FIELD

The present disclosure generally relates to the field of compounding pharmaceutical compositions and, more specifically, to compounded pharmaceutical compositions having improved quality properties as well as to systems and methods for making same.

BACKGROUND

Medical facilities, licensed pharmacist or physicians may produce individual pharmaceutical compositions by blending together various ingredients, such as one or more active pharmaceutical ingredient (API) and pharmaceutically acceptable excipients, diluent or solvents, to create a medicine product tailored to the needs of an individual patient. Such activities are commonly referred as pharmaceutical compounding. Practically speaking, in the context of pharmacy compounding, the pharmacist will typically prepare such product tailored to the needs of an individual patient based on a medical prescription.

Pharmaceutical compounding involves blending of the composition ingredients, which is typically performed using manual mixing, for example, using a pestle and mortar. However, manually mixing ingredients can be time-consuming and is often prone to cross-contamination from poorly decontaminated or sterilized equipment used for the mixing. Along with the contamination risk, there is also the problem that performing manual mixing often results in products that face repeatability and/or quality challenges. In other words, it is often difficult to obtain compositions having consistent concentrations of API from one composition to another and/or consistent homogeneous API concentration within one preparation per se. This may result in substantial qualitative differences during manufacture of the same recipe, which at minimum can have an effect on the effectiveness of the recipe.

In this regard, various practical devices have been previously suggested to overcome the above deficiencies of compounding pharmaceutical compositions using manual mixing.

U.S. 2012/0269029 (Konietzko) describes a program-controlled mixer, which includes a control unit, a motor-driven mixing unit with a blade mixing tool, which engages into a mixing vessel, and a lift unit. The lift unit produces an axial relative motion between the blade mixing tool and the mixing vessel, to move the blade mixing tool in the mixing vessel between an upper end position and a lower one, preferably at a constant lifting speed.

A deficiency associated with many mixing devices is that they often involve mixing using blades that contact the mixture causing high shearing forces, which can generate so much heat during mixing so as to degrade thermally labile API.

Additionally or alternatively, many mixing devices often entrain air into the composition being mixed. The entrained air forms air bubbles in the composition modifying thereafter the specific gravity of the pharmaceutical composition. Since the specific gravity is the ratio of the density of the composition to the density of a reference substance; equivalently, it is the ratio of the mass of the composition to the mass of a reference substance for the same given volume. Variations in specific gravity of a composition can be detrimental in that such variations alters the aforementioned ratio and, accordingly, alters the API weight content which is filled in a pharmaceutical container for a given volume of composition filled in. This is particularly critical for pharmaceutical dispensing devices dispensing measured doses which need to dispense consistent amounts of API for a given volume from one device to another one, and from one dispensed volume to the next in the same dispensing device.

In other cases, the entrained air must be removed in order to eliminate the air bubbles from the pharmaceutical composition and thereby improve the appearance of the pharmaceutical composition. For instance, in the production of either translucent or transparent pharmaceutical compositions, it is mandatory to remove the air bubbles since these would otherwise negatively affect the translucency or transparency of the pharmaceutical compositions by imparting opacity zones thereto. However, such de-aeration is time consuming, lowers throughput and generally requires additional vacuum configurations, which can be cumbersome and increase overall manufacturing costs.

Additionally or alternatively, many mixing devices often require mixing in device-specific mixing containers, which thus requires an additional step of decanting the pharmaceutical mixture into a dispensing device container, thereby increasing the risk of material loss during the decanting procedure. Device-specific containers also limit the volume and/or mass of materials that can be mixed to the specifications of such containers, which is not always ideal from a practical perspective. Device-specific containers also require implementing strict cleaning/sterilization procedures to avoid cross-contamination risk when one wishes to reuse the same mixing containers, which can be cumbersome and time-consuming. Otherwise, operation costs and waste are increased when container are used and are discarded after each mixing procedure, i.e., when used as single-use mixing containers.

SUMMARY

This Summary is provided to introduce a selection of concepts in a simplified form that are further described below in the Detailed Description. This Summary is not intended to identify key aspects or essential aspects of the claimed subject matter.

There is a need to provide improved compounded pharmaceutical composition having improved quality properties as well as devices and methods for making same, which alleviate at least in part the deficiencies of the existing devices and methods for making compounded pharmaceutical compositions.

In one embodiment, the present disclosure aims to at least address how to reduce qualitative differences during manufacturing of compounded pharmaceutical composition mixtures, and/or increase productivity, and/or improve effectiveness of compounded pharmaceutical composition mixtures.

In one broad aspect, the present disclosure relates to a composition comprising an active pharmaceutical ingredient (API) dispersed in a pharmaceutically acceptable excipient, carrier or diluent, the composition exhibiting a concentration gradient of the API with ≤6%, or ≤5%, or ≤4%, or ≤3%, or ≤2%, or ≤1%, or about 0% relative standard deviation (RSD) when measured by high-performance liquid chromatography (HPLC), wherein the concentration is that of at least top, middle and bottom layers of the composition within the container, and wherein the composition is personalized for a patient.

In another broad aspect, the present disclosure relates to a composition comprising an active pharmaceutical ingredient (API) dispersed in a pharmaceutically acceptable excipient, carrier or diluent, the composition exhibiting a concentration gradient of the API with ≤6%, or ≤5%, or ≤4%, or ≤3%, or ≤2%, or ≤1%, or about 0% relative standard deviation (RSD) when measured by high-performance liquid chromatography (HPLC), wherein the concentration is that of at least top, middle and bottom layers of the composition within the container, and wherein the composition is personalized for a patient, the composition having a specific gravity which is within 20% of corresponding specific gravity of the pharmaceutically acceptable excipient, diluent or carrier in absence of the API.

In yet another aspect, the present disclosure relates to a troche comprising an active pharmaceutical ingredient (API) dispersed in a pharmaceutically acceptable excipient, carrier or diluent, wherein the API is thermolabile at a temperature above 60° C., and the troche includes less than 1% degradation products of the API, wherein the troche is personalized for a patient In yet another aspect, the present disclosure relates to a compounding method, comprising: providing a container including therein a pharmaceutically acceptable excipient, carrier or diluent, and an active pharmaceutical ingredient (API); subjecting the container to superimposed revolution and rotation movements to disperse the pharmaceutically acceptable excipient, carrier or diluent, and the API and produce a composition exhibiting a concentration gradient of the API with ≤6%, or ≤5%, or ≤4%, or ≤3%, or ≤2%, or ≤1%, or about 0% relative standard deviation (RSD) when measured by high-performance liquid chromatography (HPLC), wherein the concentration is that of at least top, middle and bottom layers of the composition within the container, and wherein the composition is personalized for a patient.

In yet another aspect, the present disclosure relates to a compounding method, comprising: providing a container including therein a pharmaceutically acceptable excipient, carrier or diluent having a first specific gravity, and an active pharmaceutical ingredient (API); and subjecting the container to superimposed revolution and rotation movements to disperse the pharmaceutically acceptable excipient, carrier or diluent, and the API and produce a composition having a second specific gravity and exhibiting a concentration gradient of the API with ≤6%, or ≤5%, or ≤4%, or ≤3%, or ≤2%, or ≤1%, or about 0% relative standard deviation (RSD) when measured by high-performance liquid chromatography (HPLC), wherein the concentration is that of at least top, middle and bottom layers of the composition within the container, and wherein the composition is personalized for a patient, wherein the second specific gravity is within 50%, or 40%, or 30%, or 20%, or 10%, of the first specific gravity without introducing air into the composition.

In yet another aspect, the present disclosure relates to a compounding method, comprising: providing a container including therein gelatin gum base particles; subjecting the container to first superimposed revolution and rotation movements to disperse the particles and produce a melt composition; adding an active pharmaceutical ingredient (API) into the melt to obtain an API-containing melt; subjecting the container comprising the API-containing melt to second superimposed revolution and rotation movements to disperse the API-containing melt and obtain a dispersed melt composition; and cooling the dispersed melt composition to obtain a dispersed solid composition, wherein the dispersed solid composition is personalized for a patient.

In yet another aspect, the present disclosure relates to a compounding method, comprising: providing a container including therein particles of a pharmaceutically acceptable excipient, pharmaceutically acceptable carrier, or an active pharmaceutical ingredient (API), wherein the particles have a starting $D_{50}$; subjecting the container to first superimposed revolution and rotation movements in presence of grinding beads to produce a milled composition including particles having a milled $D_{50}$, wherein the starting $D_{50}$ to milled $D_{50}$ represent a ratio of at least 2.5, incorporating into the milled composition at least one of a pharmaceutically acceptable excipient, pharmaceutically acceptable carrier, or API and removing the grinding media from the container before or after said incorporating, and subjecting the container to second superimposed revolution and rotation movements to obtain a composition.

In one embodiment, any one of the herein described method is performed in a pharmacy setting.

In another embodiment, any one of the herein described method is performed under the supervision of a licensed pharmacist.

In another embodiment, any one of the herein described method is performed by a licensed pharmacist or a licensed physician.

In one embodiment, the composition can be a cream, ointment, lotion, emulsion, gel, suspension, powder, liquid solution, colloidal dispersion, troche or syrup.

In one embodiment, the composition of the present disclosure is a composition which is personalized for a patient.

For the purpose of the present disclosure, the expressions "compounded pharmaceutical composition" and "composition personalized for a patient" are used interchangeably and refer in particular to those single compositions which are assembled in a medical facility, or by a licensed pharmacy (as opposed to those compositions made in batch in a pharmaceutical industrial plant) where a pharmacist combines, mixes, or alters ingredients in response to a doctor's prescription to create a medicine tailored to the medical needs of an individual patient. In other words, the type and/or concentration of at least one of the API, the excipient, diluent or carrier is customized to create a composition tailored to the medical needs of the patient.

Compounding may, thus, be used in a variety of situations where a patient cannot be treated with a standard, commercially available, FDA- (or other regulatory body) approved medicine.

For example, a patient might be allergic to the kind of dye used in a commercially available medication. In this case, the compounding personnel would formulate the medication without the dye or with another dye. Or, sometimes elderly patients or children who cannot swallow tablets need their medicine in a liquid or suppository form that is not commercially available. Suspensions possess certain advantages over other dosage forms. Some drugs are insoluble in all acceptable media and must, therefore, be administered as a tablet, capsule, or as a suspension. Because of their liquid character, suspensions represent an ideal dosage form for patients who have difficulty swallowing tablets or capsules. This factor is of particular importance in administration of drugs to children. Suspensions of insoluble drugs may also be used externally, often as protective agents.

In addition, disagreeable tastes can be masked by a suspension of the drug or a derivative of the drug, an example of the latter being the drug chloramphenicol palmitate. Finally, drugs in suspension are chemically more stable than in solution. This is particularly important with certain antibiotics and the pharmacist is often called on to prepare such a suspension just prior to the dispensing of the preparation.

Sometimes, a patient may require a special API dosage and thus, the compounding personnel will customize the API concentration in the compounded composition.

In other cases, a patient may be allergic to the API in the commercially available medication and the compounding personnel will thus customize the composition by replacing the API with another one, hypoallergenic for the patient.

The person of skill will recognize that such are examples of a composition which is personalized for a patient.

All features of embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF FIGURES

A detailed description of specific embodiments is provided herein below with reference to the accompanying drawings in which.

Figure 1:
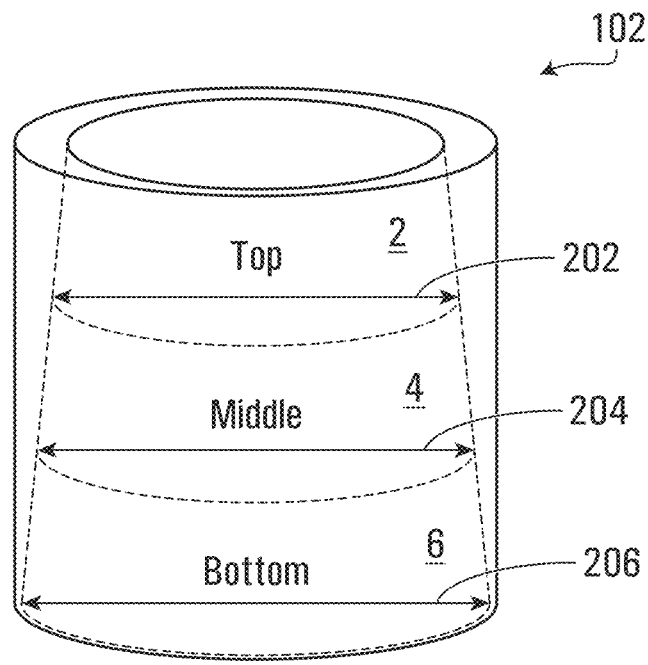
FIG. 1 shows a cross section view of a jar including a composition which is personalized for a patient, where the container is virtually separated in top, middle and bottom sections, each including respective top, middle and bottom layers of the composition, in accordance with an implementation of the present invention.

In the drawings, embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

Illustrative embodiments of the disclosure will now be more particularly described. The same features are denoted in all figures by the same reference signs. While the making and using of various embodiments of the present invention are discussed in detail below, it should be appreciated that the present invention provides many applicable inventive concepts that can be embodied in a wide variety of specific contexts. Specific embodiments discussed herein are merely illustrative of specific ways to make and use the disclosure and do not delimit the scope of the disclosure.

Composition

A composition of the present disclosure includes one or more ingredient which is tailored to medical needs of an individual patient. The composition further includes one or more characteristics which, when compared to compositions obtained with prevalent compounding methods that make use, e.g., of manual mixing, may constitute an improvement from a safety and/or quality and/or effectiveness perspective.

In one embodiment, the composition of the present disclosure can be a cream, ointment, lotion, emulsion, gel, suspension, powder, liquid solution, colloidal dispersion, troche or syrup. For the purpose of the present disclosure, the compounding composition of the present description may be packaged in a metered dose device and/or a unit dose package. A metered dose device allows administrating a dose of compounding composition, the dose of compounding composition being metered by weight or by volume. In one non-limiting example, the metered dose device is an inhaler comprising a canister, a metering valve and an actuator. The canister encloses the compounding composition, while the metering valve allows a metered dose of the compounding composition to be dispensed at each actuation of the actuator, the actuator being a mouthpiece in this example. In another non-limiting example, the metered dose device comprises a container enclosing the compounding composition, an actuator manually operated, and a metering valve allowing a metered dose of the compounding composition to be dispensed at each actuation of the actuator. A unit dose package (also referred as "individual package") allows the compounded composition to be dispensed more safely and efficiently by enclosing each unit dose in a different recipient. A unit dose is typically a dose of medication comprising a dose of at least one compounded composition that is intended to be administrated at once. The recipients may comprise paper, cardboard, plastic, metal and/or glass materials. In one non-limiting example, the recipients are paper envelopes. In another non-limiting example, the recipients are reusable boxes. In one non-limiting example, the recipients are single-use plastic boxes with a detachable paper lid. The recipients may be tagged, marked with information, such as a name of a patient, a name of a medication, a barcode and/or a moment (i.e. a day, a date and/or a moment of the day) at which the unit dose is intended to be administrated. In one non-limiting example, each recipient is tagged with a day of the week and a meal: Monday-breakfast, Monday-diner, Tuesday-breakfast, etc. The unit dose package may be provided by manually packaging the unit doses or by an automated packaging system.

In a first practical implementation, the composition of the present disclosure includes at least one active pharmaceutical ingredient (API) dispersed (mixed) in a pharmaceutically acceptable excipient, diluent or carrier in such a way that the composition has substantially the same API concentration in a top layer, a middle layer and a bottom layer of the composition, as measured with high-performance liquid chromatography (HPLC). Such composition will be referred to in this text as being a "substantially homogeneous composition".

The concept of having substantially the same API concentration in a top, middle and bottom layer of the composition is illustrated in FIG. 1A, which shows a cross-sectional view of a container 102 including a patient personalized composition, where the container 102 is virtually separated in top, middle and bottom sections, each including respective top 2, middle 4 and bottom 6 layers of the composition. The concentration of the API dispersed (mixed) in the composition is then measured in each of layers 2, 4 and 6 using a suitable technique, such as HPLC. The standard deviation (SD) between the API concentrations of the three layers 2, 4 and 6 for a given composition is then determined. The relative standard deviation (% RSD), which expresses the precision and repeatability of an assay, is then calculated based on the ratio of the standard deviation to the mean.

In a non-limiting embodiment, the composition exhibits a concentration gradient of the API having 3% relative standard deviation (% RSD), or 2% RSD, or 1% RSD, when measured at least at the top 2, middle 4 and bottom 6 layers of the composition using HPLC. In a non-limiting embodiment, the concentration gradient of the API is nil (about 0% RSD), when measured at least at the top 2, middle 4 and bottom 6 layers of the composition using HPLC.

In one embodiment, the API can be present in an amount of 80 wt. % relative to total weight of the composition. For example, the API can be present in an amount selected in the range of 0.05 wt. % to 80 wt. %, or 0.05 to 70 wt. %, or 0.05 to 60 wt. %, or 0.05 to 50%, or 0.05 to 50 wt. %, or any other desired amount.

In a non-limiting embodiment, the composition includes at least a second API dispersed (mixed) in the pharmaceutically acceptable excipient, carrier or diluent, the second API, and the composition exhibiting a concentration gradient of the at least second API having ≤6% RSD, or ≤3% RSD, or ≤2% RSD, or ≤1% RSD, when measured at least at the top 2, middle 4 and bottom 6 layers of the composition using HPLC. In a non-limiting embodiment, the concentration gradient of the at least a second API is nil (about 0% RSD), when measured at least at the top 2, middle 4 and bottom 6 layers of the composition using HPLC.

In a non-limiting embodiment, the concentration gradient of the at least second API can be approximately the same as the concentration gradient of the first API.

In another non-limiting embodiment, the concentration gradient of the at least second API is significantly different than the concentration gradient of the first API.

Different types of pharmaceutical compositions have been prepared by the present inventors with the above low % RSD values.

In a second practical implementation, the composition of the present disclosure includes an API dispersed (mixed) in a pharmaceutically acceptable excipient, diluent or carrier in such a way that the composition has reduced air entrapment levels.

One practical way of assessing air entrapment levels in the composition is to measure the specific gravity of the composition before and after the dispersion (mixing) procedure and/or of a composition prepared with the herein described process to a composition prepared with a dispersion procedure of the prior art, such as mixing with an electronic mortar and pestle.

For example, it has been observed by the present inventors that compounding pharmaceutical ingredients using prior art processes such as the electronic mortar and pestle can incorporate significant amounts of air into the composition under certain circumstances (i.e., >30% variation in the composition's specific gravity). In such cases, the air entrapped in the composition creates air bubbles which are undesirable from a product quality perspective. It is, thus, common in the art to further process compositions which have been mixed with the electronic mortar and pestle with another device to remove the air bubbles entrapped therein. In such cases, the compounding process can thus include the use of at least two devices, the electronic mortar and pestle and another device such as the Unguator™ (Gako International GmbH), to remove entrapped air. The use of two devices can be cumbersome, increase operation costs, delays, likelihood of cross-contamination, material loss (e.g., through decanting from one container suitable for mixing with the electronic mortar and pestle to another container suitable for the Unguator), and/or other undesirable effects which will become apparent to the person of skill in view of the present disclosure.

In contrast, and as will be further discussed later in this text, the herein described superimposed revolution and rotation movements, typically, will not introduce air during the dispersing (mixing) process, and if the starting composition ingredients (i.e., before dispersion) initially include air entrapped therein, the herein described superimposed revolution and rotation movements will deaerate the composition while dispersing (mixing) the ingredients. This can be advantageous, in particular when the herein described superimposed revolution and rotation movements is implemented in a single device, as will be further discussed later in this text.

In this particular implementation, the patient personalized composition of the present disclosure includes an API dispersed (mixed) in a pharmaceutically acceptable excipient, diluent or carrier. The composition has a specific gravity which is within 20%, or within 10%, or within 5%, or within 2%, of the specific gravity of the pharmaceutically acceptable carrier, diluent or excipient in absence of the API. Preferably, such composition exhibits a concentration gradient of the API with ≤6% RSD, or ≤3% RSD, or ≤2% RSD, or ≤1% RSD, or RSD being nil (about 0%), when measured at least at the top 2, middle 4 and bottom 6 layers of the composition using HPLC. relative standard deviation (RSD) when measured at least at a top, middle and bottom layers of the composition by high-performance liquid chromatography (HPLC).

In one embodiment, the composition of the present disclosure includes an API dispersed (mixed) in a pharmaceutically acceptable excipient, diluent or carrier, and has a specific gravity which is substantially identical to the specific gravity of the pharmaceutically acceptable carrier, diluent or excipient without the API.

In a third practical implementation, the composition of the present disclosure includes an API which is thermally labile at a temperature above 50° C., or above 60° C., or above 80° C. The API is dispersed (mixed) in a pharmaceutically acceptable excipient, diluent or carrier. This composition includes less than 1.0% degradation products of the thermally labile API. The person of ordinary skill will readily appreciate that the percentage here represents a wt./wt. percentage relative to the total weight of the thermally labile API added into the composition before dispersion (mixing).

In one non-limiting embodiment, the amount of degradation products of the thermally labile API represents less than 0.75%, 0.5%, 0.1%, 0.05%, or 0.01% wt./wt. percentage relative to the total weight of the thermally labile API added into the composition before dispersion.

For the purpose of the present specification, a thermally labile API is an active pharmaceutical compound that is altered or degrades when exposed to high temperatures, e.g. above 50° C., or above 60° C., or above 80° C., or more. Typically, compounding methods that make use of blades for mixing will generate high temperatures, which can alter or degrade thermally labile API to a certain extent such that it increases costs and/or reduces yield of composition having effective API concentrations and/or produces unwanted degradation and/or alteration of the API, possibly generating by-products. In certain prior art compounding methods that make use of blades, it can be quite common to obtain dispersed composition having more than 1.5% degradation products of thermally labile API.

The reader will readily understand that quantification of API degradation product levels in the dispersed composition can be performed using one of a variety of chromatographic or spectroscopic techniques known in the art, including HPLC, thin-layer chromatography (TLC), High performance thin layer chromatography (HPTLC), Atomic absorption spectroscopy (AAS), and the like.

In a fourth practical implementation, the composition of the present disclosure is in the form of a molded troche and includes an API dispersed in a pharmaceutically acceptable excipient, diluent or carrier. The API is thermolabile at a temperature above 60° C. and the composition includes less than 1.0% degradation products of the thermally labile API wt./wt. percentage relative to the total weight of the thermally labile API added into the composition before dispersion.

In one non-limiting embodiment, the amount of degradation products of the thermally labile API in the troche represents less than 0.75%, 0.5%, 0.1%, 0.05%, or 0.01% wt./wt. percentage relative to the total weight of the thermally labile API added into the composition before dispersion.

In a specific embodiment, the troche is a chewable troche.

In a specific embodiment, the troche includes a gum base gelatin.

The troche can have similar features as those set forth previously with respect to the composition, namely a concentration gradient of the API with ≤6% RSD, or ≤3% RSD, or ≤2% RSD, or ≤1% RSD, or RSD being nil (about 0%), when measured at least at a top, middle and bottom layers of the troche by high-performance liquid chromatography (HPLC)

A troche (also interchangeably referred to in the text as a "lozenge") is intended to be held in the mouth or pharynx and contains one or more API(s) either dissolved or dispersed in a base. Troches are typically used for patients who have difficulty swallowing solid oral dosage forms (for example, paediatric or geriatric patients) as well as for API(s) which should be released slowly to yield a constant amount of drug in the oral cavity or to coat the throat tissues with the API(s). Commercial lozenges are made by moulding or by compression.

Compression techniques are typically used when manufacturing solid troches that are intended to slowly dissolve or disintegrate in the mouth. Compression is also advisable when incorporating thermolabile APIs, as there is no excessive heat involved when compressing the troche ingredients.

Moulding techniques are typically used when manufacturing solid, soft or chewable troches and in particular, when one wishes to impart a specific shape to the troche. Moulding techniques usually involve high temperature processing of the ingredients to obtain a melt, dispersing the API in the melt to obtain an API-containing melt, and casting the dispersed API-containing melt into a mold having a desired shape, and cooling the API-containing melt into the desired shape. Because of the high temperatures (e.g., 90-100° C.) usually involved with moulding, troches made with this technique typically do not include thermolabile APIs, as thermolabile APIs will usually degrade or convert to by-products in presence of such high temperatures. This in turn effectively limits the nature or concentration of the API that can be incorporated into molded troches to a certain non-thermolabile subset, which may not be practical for certain applications.

As explained later in the present disclosure, the herein described superimposed revolution and rotation movements can be used to obtain a melt and disperse therein a thermolabile API at a temperature which is sufficiently low so as to limit the degradation of the thermolabile API and obtain an API-containing melt which can be molded into a troche having less than 1.0%, 0.75%, 0.5%, 0.1%, 0.05%, or 0.01% degradation products of the thermally labile API.

Superimposed Revolution and Rotation Movements

A number of devices can be used to obtain the compounded pharmaceutical composition of the present disclosure so long as the device is capable of implementing the superimposed revolution and rotation movements as described herein.

In one non-limiting practical implementation, the herein described superimposed revolution and rotation movements can be performed using a planetary mixer.

A planetary mixer is capable of performing the herein described superimposed revolution and rotation movements by continually and concurrently revolving and rotating a container which includes the composition ingredients. This dual action eliminates the need for mixing rods, blades or media, or an evacuation device and can dramatically reduce processing times relative to other mixing devices that use blades to mix ingredients. In one embodiment, the mixing time may be no more than 900 seconds. For example, the herein described superimposed revolution and rotation movements may be performed for less than 10, 15, 20, 25, 30, 35, 40, 45, 50, 55, 60, 75, 100, 120, 150, 180, 240, 300, 400, 500, 600, 700, 800, or 900 seconds, as well as any values included therein.

Such processing time is significantly reduced when compared to the processing time required for compounding processes known in the art for compounding pharmaceutical compositions, such as the typical mortar and pestle system or devices with mixing blades, which may require an additional vacuum step to remove air entrapment in the composition. While the processing time in the superimposed revolution and rotation movements of the present disclosure is thus relatively reduced, the intensity of the processing procedure is sufficiently intense to disperse the ingredients to the point where the resulting mixture is substantially homogenous and is sufficiently gentle to prevent the internal temperature of the mixture from reaching or getting close to a degradation temperature threshold of the API.

In one embodiment, the superimposed revolution and rotation movement parameters may induce a maximal G force value of at least 50 g (corresponding to approximately 1490 m/s$^2$). In some cases, the superimposed revolution and rotation movement parameters may induce a maximal G force value of less than 500 g, or in the range of 50 g to 400 g, or 75 g to 350 g, or any suitable value within these ranges. Inducing such a maximal G force in a process by performing the herein described superimposed revolution and rotation movements can be useful for compounding compositions which are otherwise difficult or cumbersome to compound using prior art electronic mortar and pestle system or devices with mixing blades.

In one embodiment, the superimposed revolution and rotation movements are operated with operational parameters that may include revolution speeds of from at least 400 revolutions per minute ("rpm" or "RPM"). For example, a suitable revolution speed can be selected in the range of from 400 to about 4000 rpm, or from 400 to about 2000 rpm, or any suitable value within these ranges.

In one embodiment, the superimposed revolution and rotation movements are operated with operational parameters that may include revolution:rotation rpm ratios of about 10:4.

In certain embodiments, the revolution rpm, the rotation rpm and the mixing time are configurable parameters and their values may be individually selectable or they may be selectable from pre-determined combinations of parameter values. In other embodiments, the ratio between rotation rpm and revolution rpm may be a configurable parameter and thus would constrain the revolution rpm for a certain rotation rpm or vice versa. Moreover, the geometric configuration of the planetary mixer (e.g., the eccentricity (distance between the center of rotation and the center of revolution), the dimensions of the container, etc.), combined with the revolution rpm and rotation rpm, results in a certain acceleration (G force, measured in g or m/s$^2$) being felt by the material in the container. In some embodiments, the desired G force may be input to the planetary mixer, which could result in selection, by the planetary mixer, of the revolution rpm and/or the rotation rpm.

In other embodiments, the minimum or maximum G force may be specified, resulting in thresholding of the rotation rpm and/or the revolution rpm, depending on the values entered. In still further embodiments, certain parameters (such as the rotation rpm or the revolution rpm) may be dynamic (i.e., vary over time) and may be input as a function of time function so as to follow a pre-determined curve. There may exist still further controllable parameters of superimposed revolution and rotation movements implemented by a planetary mixer, such as the total weight of the container being mixed.

The reader will readily recognize that the herein described process offers a number of benefits to the compounding industry, in particular when this process can be integrated within a single device, namely a planetary mixer.

Various implementations of the herein described superimposed revolution and rotation movements will now be described with reference to dispersing, milling, melting and de-aerating applications for compounding pharmaceutical compositions (i.e., patient personalized compositions), which can be advantageously performed in a pharmacy setting in a single device, namely a planetary mixer.

While each of these applications is described in the following sections as separate variant processes, the reader will readily understand that these applications are not mutually exclusives. In other words, more than one of these applications can be performed during the same superimposed revolution and rotation movements implemented in single planetary mixer, i.e., ingredients of a patient personalized composition can be processed so as to mix and de-aerate; or so as to mix, melt and de-aerate; or so as to mix and grind; or any other combinations thereof.

Mixing Process

Figure 2:
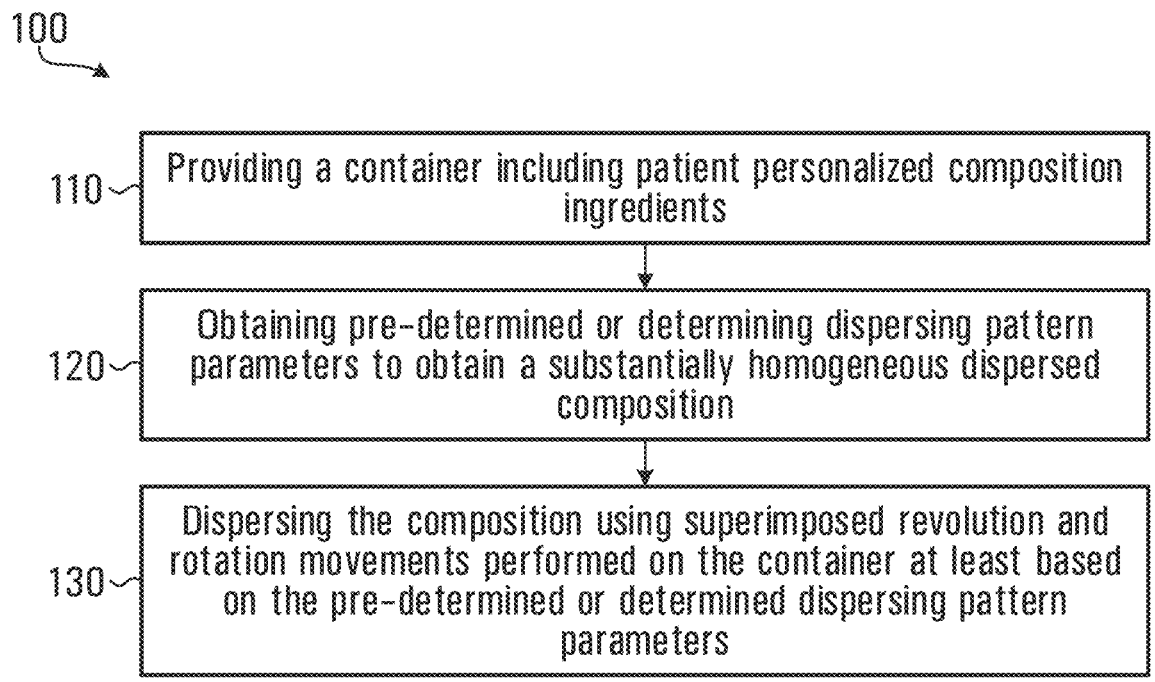
FIG. 2 is a flow diagram of a process to obtain the patient personalized composition of FIG. 1, in accordance with an implementation of the present invention.

FIG. 2 is a flow chart of a general process 100 of preparing a compounded pharmaceutical composition in accordance with an embodiment of the present disclosure.

In the process 100, the superimposed revolution and rotation movements are implemented in a planetary mixer for preparing a patient personalized composition by dispersing an API into a pharmaceutically acceptable excipient, diluent or carrier so as to obtain a substantially homogeneous patient personalized composition.

At step 110, the process includes providing the composition ingredients in a container (also referred to in this text as a "jar") configured for containing the composition ingredients. Typically, the composition ingredients include at least one API and at least one pharmaceutically acceptable excipient, diluent or carrier.

At step 120, the process includes obtaining pre-determined or determining dispersing parameters which are required to perform a superimposed revolution and rotation movements on the composition ingredients to obtain a substantially homogeneous dispersed composition.

At step 130, the process then includes dispersing the composition using the superimposed revolution and rotation movements at least based on the pre-determined or determined dispersing parameters so as to produce the substantially homogeneous dispersed composition.

Melting Process

Figure 3:
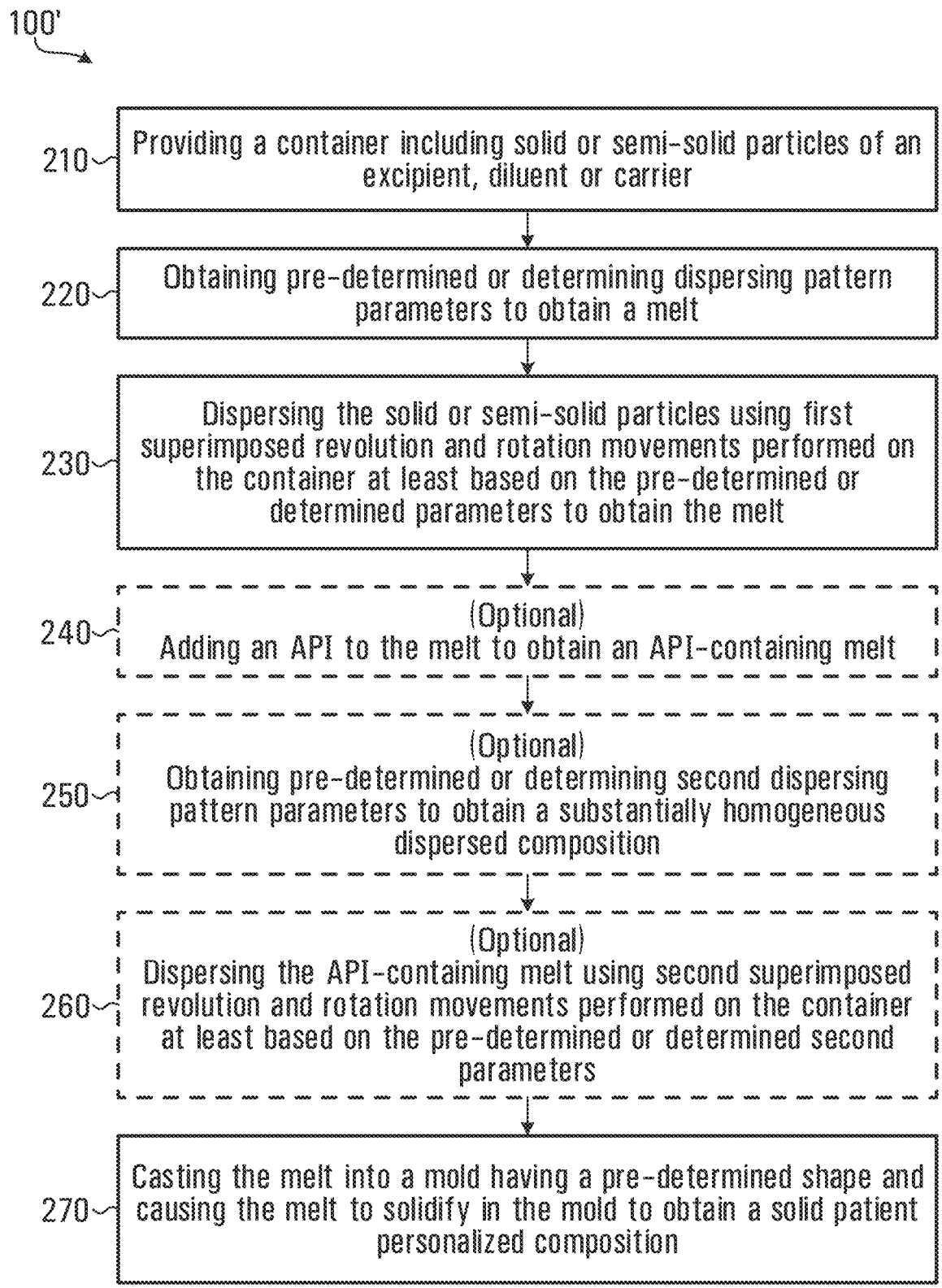
FIG. 3 is a flow diagram of a variant of the process of FIG. 2 including operating superimposed revolution and rotation movements to obtain a melt containing an API, and molding the melt into a solid form of a patient personalized composition, in accordance with an implementation of the present invention.

FIG. 3 is a flow chart of a process variant 100' of preparing a compounded pharmaceutical composition in accordance with an embodiment of the present disclosure. In this variant, the process 100' is implemented in a planetary mixer for preparing a patient personalized composition by reversibly melting pharmaceutically acceptable excipient, diluent or carrier initially in the form of solid or semi-solid particles into the resulting melt an API, dispersing the API into the melt, and casting the melt into a desired shape, such as a troche.

The variant 100' includes at step 210, providing pharmaceutically acceptable excipient, diluent or carrier in the form of solid or semi-solid particles in a container configured for containing the particles. Optionally, at this step, at least one API is also provided in the container.

In one embodiment, the excipient, diluent or carrier in the form of solid or semi-solid particles is a polymeric material which can be reversibly melted. In a particular implementation, excipient, diluent or carrier in the form of solid or semi-solid particles is a gelatin-based material.

At step 220, the process includes obtaining pre-determined or determining dispersing parameters which are required to perform the superimposed revolution and rotation movements on the solid or semi-solid particles to obtain a more or less viscous melt.

At step 230, the process includes dispersing the solid or semi-solid particles at least based on the pre-determined or determined parameters to obtain the melt. Without being bound by any theory, it is believed that the superimposed revolution and rotation movements can melt the solid or semi-solid particles through impact of the particles against each other and/or against the container walls, thus generating kinetic energy, without requiring the addition of external heat. This process advantageously can melt the material at a temperature which is below the Tg or Tm of the solid or semi-solid particles.

In one embodiment, the at least one API is not incorporated into the container at step 210. In such embodiment, the solid or semi-solid particles are thus melted in step 230 in the absence of an API. In such embodiment, it is thus necessary to incorporate at least one API at one point to obtain the compounded pharmaceutical composition. This is achieved with optional step 240, in which an API is added to the melt obtained in step 230 so as to obtain an API-containing melt. In FIG. 3, step 240 is therefore labelled as being optional as it may be discarded in case at least one API was incorporated into the container at step 210 and no further API is added to the composition.

At step 250, the process includes obtaining pre-determined or determining second dispersing parameters which are required to perform second superimposed revolution and rotation movements on the API-containing melt to obtain a substantially homogeneous dispersed composition.

At step 260, the process then includes dispersing the API-containing melt at least based on the pre-determined or determined second dispersing parameters to so as to produce a substantially homogeneous dispersed composition.

At step 270, the process then includes incorporating the dispersed composition into a mold having a desired shape and causing the incorporated dispersed composition to solidify into the mold shape.

This process 100' thus affords the reversible melt of pharmaceutically acceptable excipients, carriers or diluents which can be useful, for example, when making compositions which require pouring into some sort of mold to impart a shape thereto, for instance when making compounded pharmaceutical compositions in the form of troches, suppositories or throat lozenges. Advantageously, the melt can be obtained with the herein described dispersing process at temperatures below the typical molten transition temperature of the ingredients being dispersed such that it may enable the production of solid dispersion systems from thermally incompatible materials. In other words, such composition can advantageously incorporate thermally labile API which are typically not found or are found in limited concentration in troches.

In the prior art, such shaped compounded pharmaceutical compositions are typically made by first thermally treating a suitable pharmaceutically acceptable excipients, carriers or diluents in solid form for a sufficient extent of time so as to obtain a melt, adding the desired API (or mixture thereof), dispersing the API into the melt to obtain a mixture, and pouring the mixture into the mold so as to obtain the desired shaped compounded pharmaceutical composition. It will be noted that, typically, API which are incorporated into such melted pharmaceutically acceptable excipients, carriers or diluents are more thermally resistant so as to be able to bear the higher temperatures involved with melting the carrier, excipient or diluent. This, in turn, can limit the nature of the API that can be incorporated into such melts or requires higher amounts of API to take into account the expected API thermal degradation.

Milling Process

Figure 4:
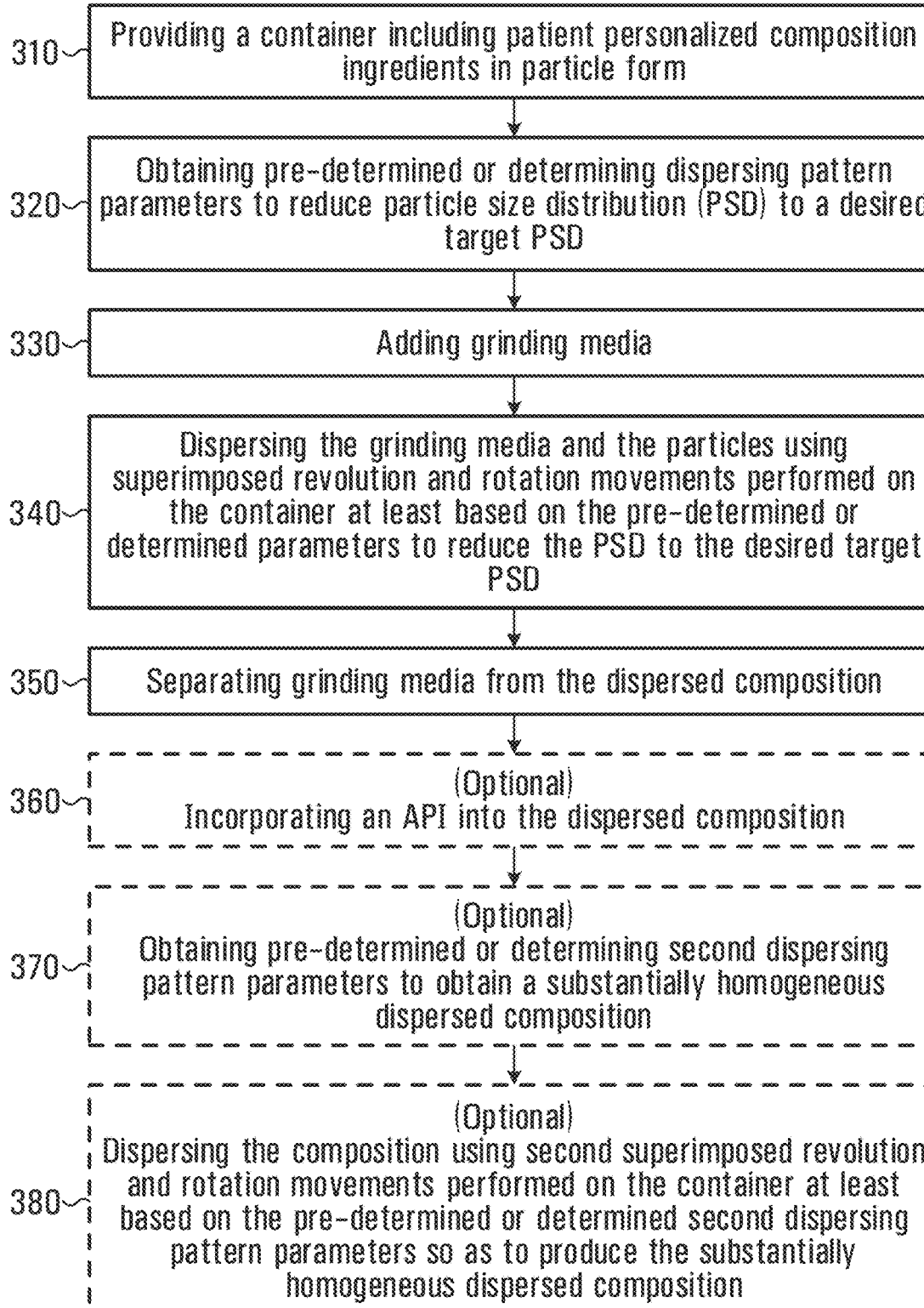
FIG. 4 is a flow diagram of a variant of the process of FIG. 2 including operating superimposed revolution and rotation movements in presence of grinding media to reduce particle size distribution (PSD) of at least one ingredient of a patient personalized composition to a desired target PSD, in accordance with an implementation of the present invention.

FIG. 4 is a flow chart of a process variant 100" of preparing a compounded pharmaceutical composition in accordance with an embodiment of the present disclosure. In this variant, the process 100" is implemented in a planetary mixer for preparing a patient personalized composition which includes a step of reducing the particle size distribution (PSD) of at least one of the ingredients in the patient personalized composition. Reducing the PSD of one of the ingredients can be useful in reducing the gritty feeling of the resulted compounded composition, such as for example but not being limited to the case of a topical cream, ointment or gel.

The process 100" includes at step 310, providing a container including at least one patient personalized composition ingredient such as one of an API, a pharmaceutically acceptable excipient, diluent or carrier in the form of particles where the container is configured for containing the particles.

At step 320, the process includes obtaining pre-determined or determining dispersing parameters which are required to perform superimposed revolution and rotation movements on the particles to reduce the PSD to a desired target PSD. Advantageously, the pre-determined or determined dispersing parameters are selected so as to ensure that any heat generation which could be caused during the dispersing step through the impact of particles and/or grinding media against each other and/or against the container inner walls does not reach a degradation temperature of the API.

At step 330, the process includes adding grinding media to the container. It will be apparent to the reader that steps 320 and 330 can occur in any sequence and are not limited to a serial sequence. In other words, the step 330 can occur before, during or after step 320.

At step 340, the process includes dispersing the grinding media and the particles at least based on the pre-determined or determined parameters to reduce the PSD to the desired target PSD.

At step 350, the grinding media is separated from the dispersed composition. This can be achieved either by removing from the container, the grinding media or the dispersed composition.

When step 310 does not include the addition of an API and/or when the compounding prescription recipe requires addition of an API after the dispersing step 340, the process includes a step 360. It will be apparent that this step is optional as the API can be incorporated at step 310. At step 360, an API is incorporated into the dispersed composition obtained after step 350.

At optional step 370, the process includes obtaining pre-determined or determining second dispersing parameters which are required to perform superimposed revolution and rotation movements on the dispersed composition obtained after step 360 so as to obtain a substantially homogeneous dispersed composition.

At optional step 380, the process includes dispersing the composition using the superimposed revolution and rotation movements at least based on the pre-determined or determined second dispersing parameters so as to produce the substantially homogeneous dispersed composition.

It will apparent that in a variant, the superimposed revolution and rotation movements in presence of grinding media are performed on the API in presence of the pharmaceutically acceptable excipient, diluent or carrier.

In another variant, the superimposed revolution and rotation movements in presence of grinding media are performed on the API in absence of the pharmaceutically acceptable excipient, diluent or carrier.

When performing the process in presence of grinding media, the size of the particles to grind, the size of the grinding media used to grind, and the size of the resulting particles can be selected such that, for example:

$$0.004 < MS(SP)/MS(B) < 0.12$$

$$0.0025 < MS(FP)/MS(SP) < 0.25$$

where MS(SP) represents the mean size diameter of the particles before grinding (starting particles), MS(FP) represents the mean size diameter of the particles after grinding (final particles), and MS(B) is the mean size diameter of the grinding beads.

The grinding media may include balls (spheres) or pellets (cylinders) made of, for example, but not limited to, hardened steel, stainless steel, tungsten carbide, agate, sintered aluminium oxide, silicon nitride or zirconium oxide.

De-Aerating Process

Figure 5:
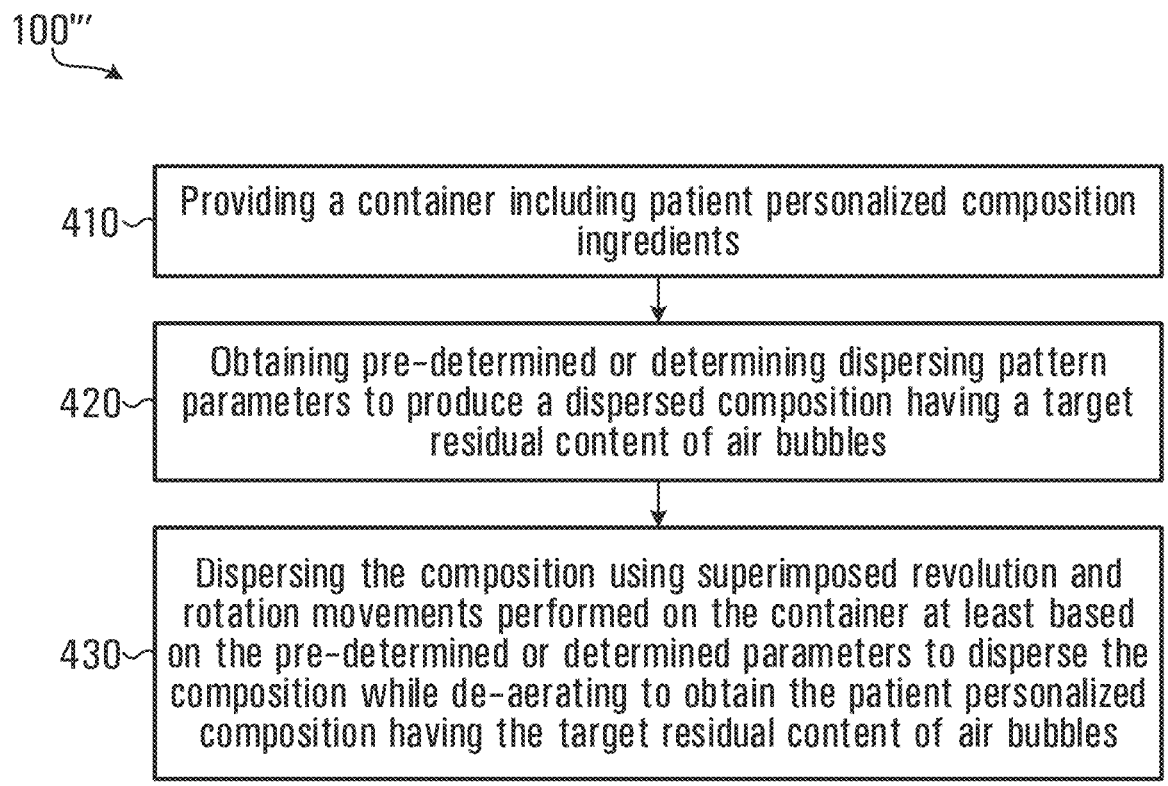
FIG. 5 is a flow diagram of a variant of the process of FIG. 2 including operating superimposed revolution and rotation movements to disperse (mix) and de-aerate a patient personalized composition, in accordance with an implementation of the present invention.

FIG. 5 is a flow chart of a process variant 100''' of preparing a compounded pharmaceutical composition in accordance with an embodiment of the present disclosure.

In this variant, the process 100''' is implemented in a planetary mixer for preparing a patient personalized composition by dispersing an API into a pharmaceutically acceptable excipient, diluent or carrier in such manner as to minimize air entrapment into the dispersed composition or to remove any air which was present in the composition before dispersion. This can be useful in controlling the composition's specific gravity and/or reducing incorporation of air bubbles in the resulting patient personalized composition, such as for example but not limited to topical creams, ointments or gels.

The process 100''' includes at step 410, providing patient personalized composition ingredients such as an API, a pharmaceutically acceptable excipient, diluent or carrier in a container configured for receiving these ingredients.

At step 420, the process includes obtaining pre-determined or determining dispersing parameters which are required to perform superimposed revolution and rotation movements on the personalized composition ingredients to disperse same while reducing or maintaining a target content of incorporated air in the composition.

At step 430, the process includes dispersing the ingredients using the superimposed revolution and rotation movements at least based on the pre-determined or determined parameters to disperse same while reducing or maintaining a target content of incorporated air in the composition.

Equipment and Processes for Industrial Applicability of the Invention

The herein described bladeless dispersion pattern process may be performed in a single device, notably in a planetary mixer.

Commercially available planetary mixers, such as the MAZERUSTAR mixer KK-300SS, KK-400W or KK-1000W from Kurabo Industries, Ltd. of Osaka, Japan or the THINKY MIXER AR-100, ARE-310, ARE-400TWIN, ARE-500, ARV-50LED, ARV-310/310LED, ARV-930-TWIN, ARV-5000, ARV-3000TWIN, and ARV-10kTWIN from Thinky Corporation of Tokyo, Japan, and the like, can be used for this purpose.

A planetary mixer typically includes a jar arranged eccentrically on a so-called sun wheel, at a certain distance from the center. The jar is configured for receiving a container which contains the ingredients being processed. The planetary mixer is configured to impart a revolution movement to the sun wheel and a rotational movement to the jar, where the revolution movement is in an opposite direction to that one of the rotation such that the ingredients contained in the container are subjected to a pattern of motion throughout space, which includes superimposed revolution and rotation movements. Advantageously, this pattern of motion throughout space does not involve any blades, i.e., it is a bladeless dispersion pattern of motion throughout space. When grinding media is added to the container, the grinding media is also subjected to these superimposed movements, where the difference in speeds between the grinding media and the container produces an interaction between frictional and impact forces, which releases high dynamic energies causing size reduction of the materials in the container.

In certain embodiments, the container receiving the ingredient is adapted to receive on a top end thereof, a dispensing system element such as a pump, a spray nozzle, applicator cap, and the like. It will be appreciated that the dispensing system element can further be adapted for dispensing metered doses as described, e.g., in U.S. 2014/0221945 filed Feb. 4, 2014 and PCT/CA2016/050179, filed Feb. 23, 2016. This implementation effectively avoids or eliminates decanting steps, thus, minimizing the risk of material loss. This implementation also reduces time required for cleaning the container after a compounding procedure, which is typically required to avoid cross-contamination risks that exist when using the same container for dispersion of various compounded pharmaceutical compositions. The reader will appreciate that when performing the milling step, the grinding media is preferably removed from the container before the latter receives the dispensing system element at the top end thereof.

Such features are also advantageous to the compounding industry and are believed to address an unmet need in this industry.

Figure 6:
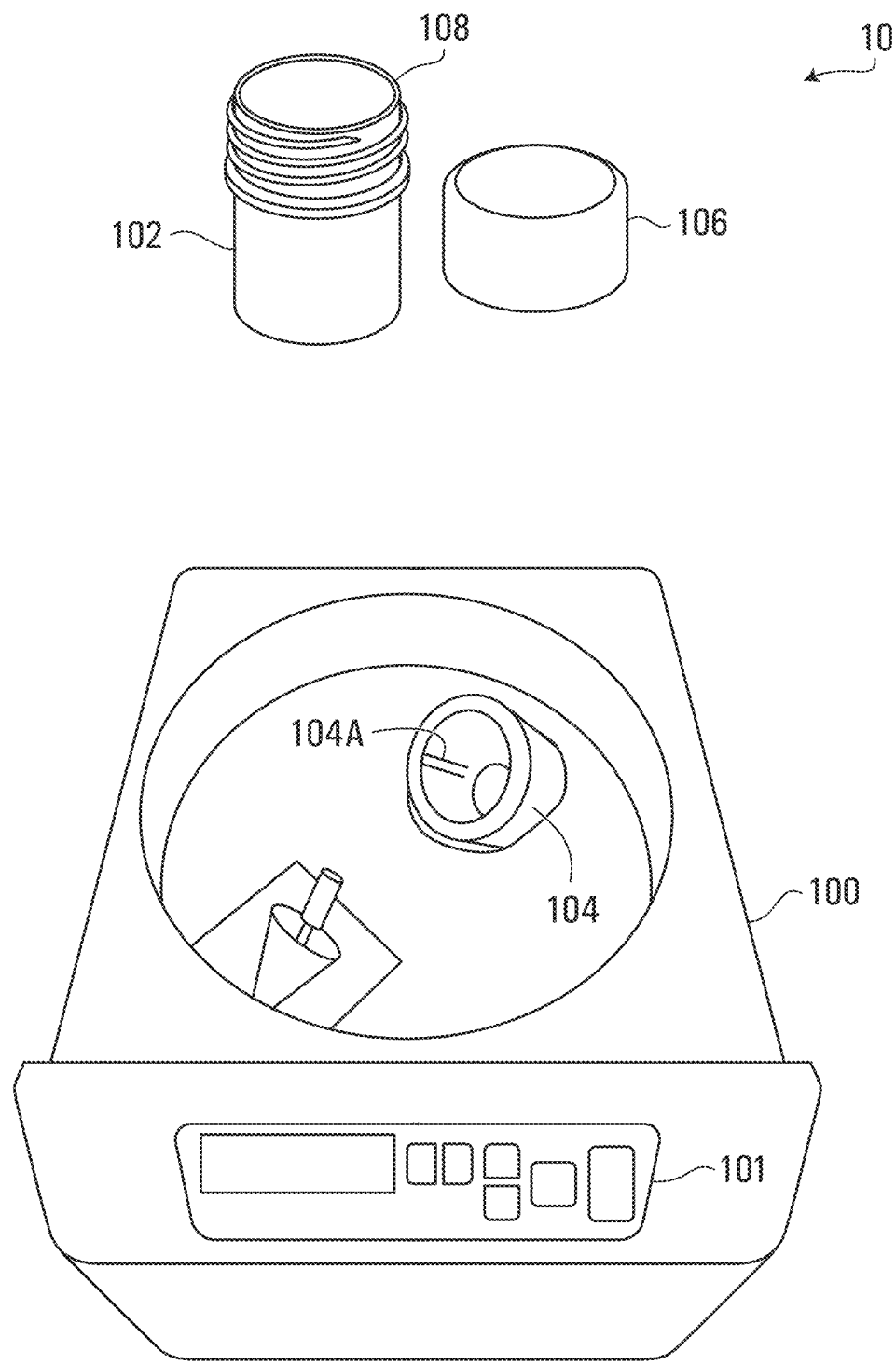
FIG. 6 shows a system for compounding a pharmaceutical composition using superimposed revolution and rotation movements, in accordance with an implementation of the present invention.

FIG. 6 generally shows a planetary mixing system 10 which includes a planetary mixing apparatus 100 configured to effect the herein described superimposed revolution and rotation movements through rotation and revolution of a jar 102 placed in a jar holder 104.

The system 10 includes a lid 106 that attaches onto a mouth 108 of the jar 102. The lid 106 may be a screw-on lid as shown, or it may be a snap-on lid, for example. The jar 102 and the lid 106 may be made of high density polyethylene (HDPE) or polypropylene, for example.

The jar 102 may have different interior and exterior dimensions. With reference to the elevated cross-sectional view in FIG. 1, the jar 102 may have an inside diameter 202, 204, 206 that changes from the top of the jar 102 to the bottom of the jar 102. For example, the inside diameter 202 at the top of the jar 102 may be smaller than the inside diameter 206 at the bottom of the jar 102. This gradient can be achieved in two or more sections or as a gradual taper. In the illustrated embodiment, the jar 102 has three sections 212, 214, 216, with the top section 212 having the smallest inside diameter 202, the bottom section 216 having the largest inside diameter 206 and the middle section 214 whose inside diameter 204 is somewhere in between. Example dimensions for the top, middle and bottom inside diameters, not to be considered limiting, are 65 to 70 mm, 65 to 70 mm and 65 to 70 mm, respectively. Alternatively, one can consider that the top inside diameter 202 is between 90 and 99.9 percent of the middle inside diameter 204, and the middle inside diameter 204 is between 90 and 99.9 percent of the inside diameter 206. Also, there are multiple height dimensions possible for the jar 102. For example, the height dimension of the jar 102 (measure externally) could be in the range from 85 mm to 120 mm.

Figure 7:
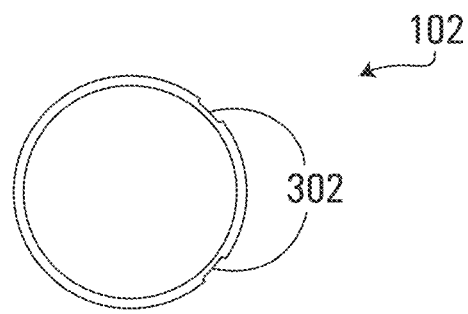
FIG. 7 shows a top view of the jar of FIG. 1 for use with the system of FIG. 6, in accordance with an implementation of the present invention.

The outside of the jar 102 may be configured to be received in the jar holder 104. In particular, the jar holder 104 may include a plurality of circumferentially spaced projections 104A. Correspondingly, and as shown with additional reference to FIG. 7, the jar 102 may, accordingly, include a plurality of circumferentially spaced notches 302 that receive the projections 104A, so as to prevent free-spinning of the jar 102 within the jar holder 104. As a result, rotation of the jar 102 will only occur when the jar 104 holder itself rotates. Other rotational stoppage mechanisms may be provided in different embodiments. In other embodiments, the jar 102 may be of any other suitable shape and may include an internal surface that may be smooth, rough, and/or comprise any suitable texture.

Containers of various sizes for containing pharmaceutical composition exist in the market, such as (i) containers in which compounds are traditionally dispersed by an electric mortar/pestle and (ii) containers from which compounds are dispensed (such as bottles and syringes). As will be discussed later in this text, the system 10 may be configured to implement the superimposed revolution and rotation movements described here in containers/jars of various sizes.

Figure 8:
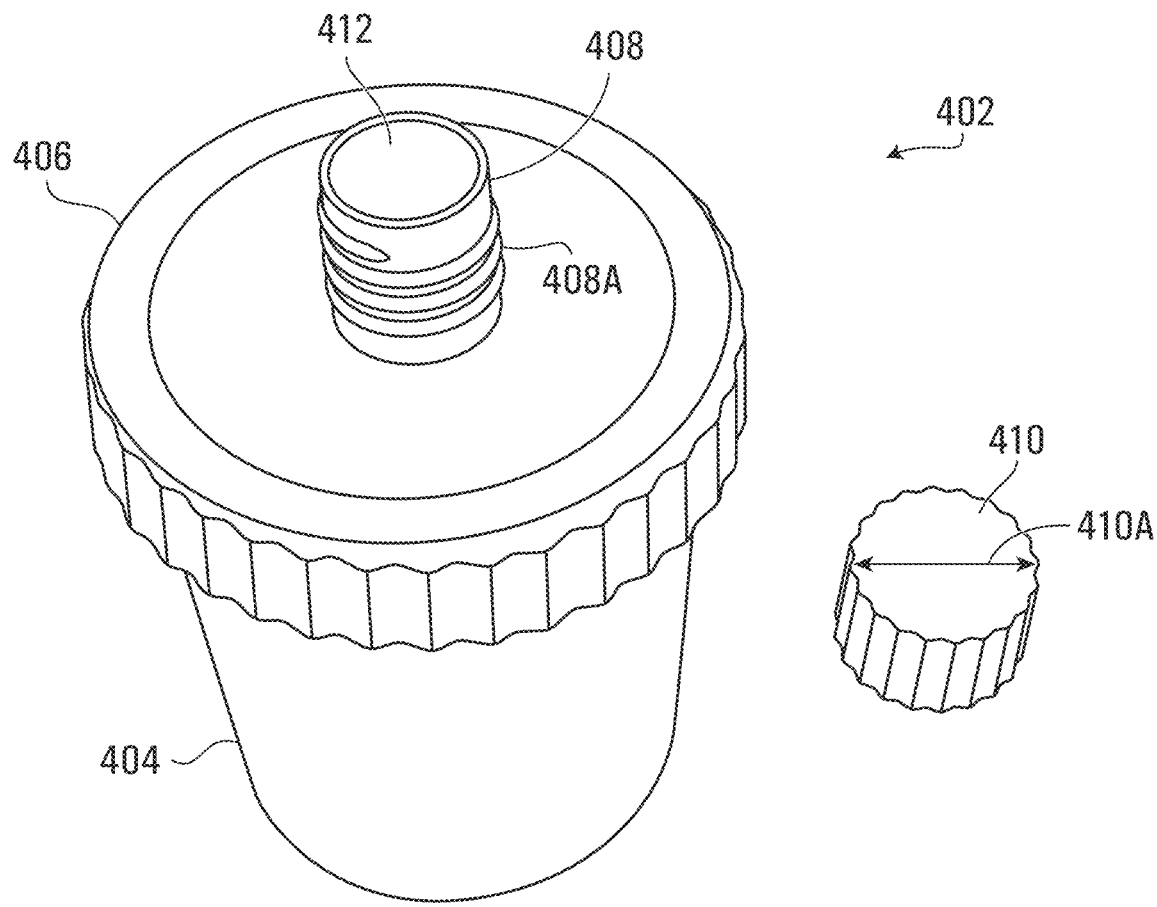
FIG. 8 shows a side isometric view of a variant dispensing jar for use with the system of FIG. 6, in accordance with an implementation of the present invention.

FIG. 8 shows an example container 402 in which pharmaceutical composition ingredients would traditionally be dispersed by an electric mortar/pestle. One example of the container 402 is referred to in the industry as an Unguator™ jar (available from GAKO Konietzko GmbH, Bamberg, Germany), although recently similar containers have been made available by Samix GmbH, Zella-Mehlis, Germany.

The container 402 includes a body 404 and a cover 406. The body 404 and the cover 406 may be complementarily threaded. The cover 406 includes a nozzle 408, which may include an external thread 408A to receive an internally threaded cap 410. The cap 410 has an external diameter denoted 410A. The nozzle 408 has an aperture 412 that allows fluid to escape the container 402 when the cap 410 is removed and a piston (not shown) is pushed from underneath the body 404. For electric mortar/pestle mixing, the cap 410 is removed from the cover, the cover 406 is removed from the body 404, a blade shaft (not shown) is inserted from underneath the cover 406 and through the aperture 412 and connected to a motor (not shown); meanwhile, the body is filled with the composition ingredients to be dispersed, then the blade is positioned inside the body 404 and the cover 406 is secured back onto the body 404.

Figure 9:
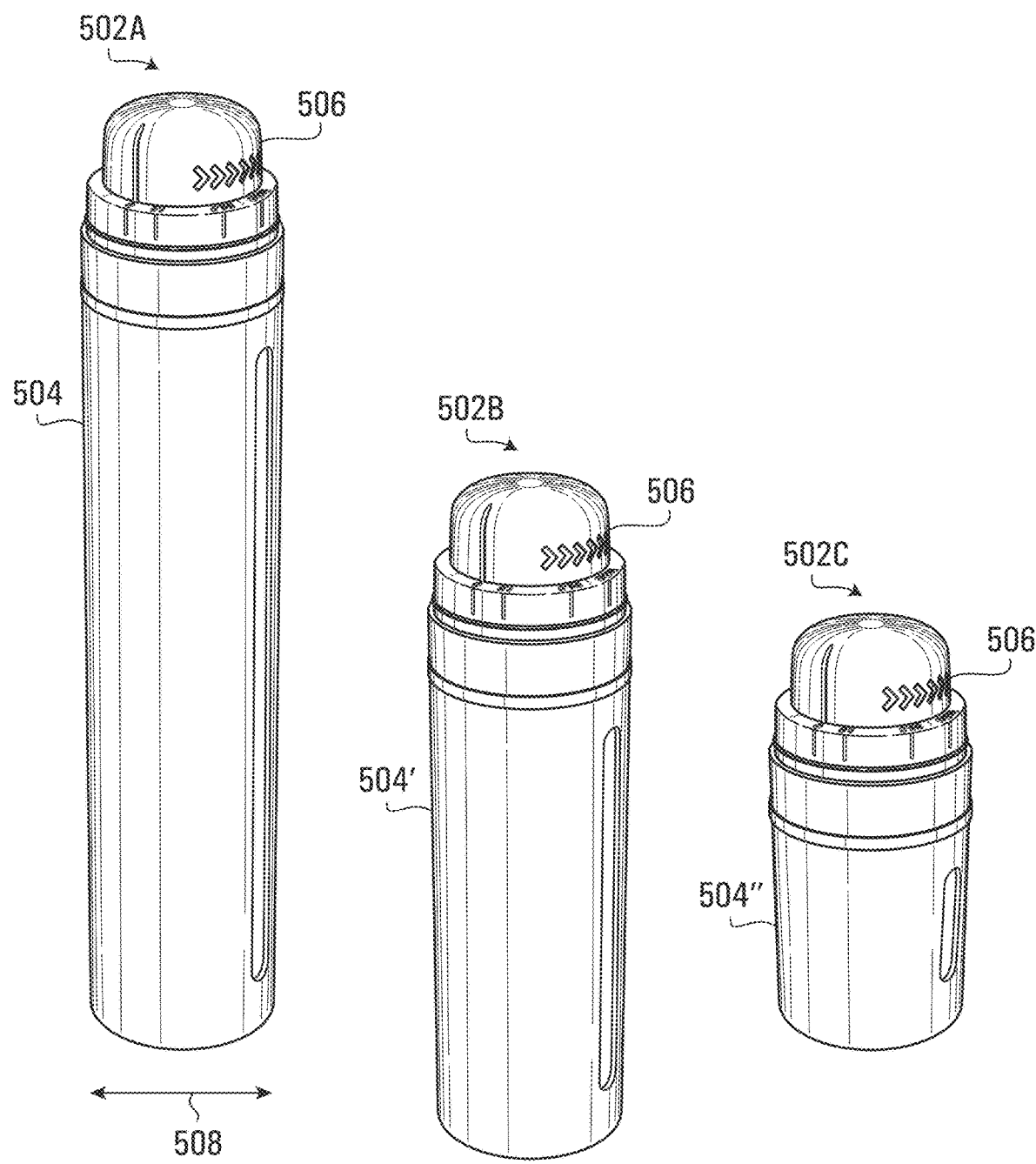
FIG. 9 shows a side isometric view of dispensing jars, each having a respective body having a different size from one another, for use with the system of FIG. 6, in accordance with an implementation of the present invention.

FIG. 9 shows alternative containers 502A, 502B and 502C. The containers 502A, 502B and 502C include a respective cylindrical body 504, 504' and 504", and an actuator 506. The actuator 506 can be actuated by a user to dispense a composition contained in the body 504. Depending on the embodiment, the actuator 506 may in fact allow metered dispensing of the composition.

As is apparent from the above, the containers used for dispersing pharmaceutical composition ingredients (e.g., containers 402, 502A) do not necessarily correspond to the jar 102. As such, in accordance with various embodiments, and with reference to FIG. 10B, there is provided an adapter 602 between the jar 102 and the container 600 (generally referred to by 600 but which could be one of the aforementioned containers 402, 502A). The container 600 has a smaller volume than the jar 102 and is secured to an interior of the jar 102 by the adapter 602. The adapter is designed not to hold the composition but rather to secure the container 600 to the jar 102. The ability to secure a container 600 with a smaller volume entirely within the jar 102 can allow smaller quantities of pharmaceutical composition ingredients to undergo efficient dispersing despite the small amount of the composition.

In one embodiment, the jar 102 may have a volume of approximately 250 ml, while the container 600 may have a volume of approximately 100 ml, or approximately 80 ml, or approximately 50 ml, or approximately 35 ml, or approximately 30 ml, or approximately 20 ml or approximately 15 ml. It should be appreciated that a height-to-base ratio (HBR) associated with a certain quantity of a composition to be dispersed in a particular vessel may be defined as the quotient between a height dimension occupied by the quantity of the composition and a base dimension occupied by the quantity of the composition, when that quantity is placed into the particular vessel. The HBR may be a parameter indicative of how efficiently the composition will be dispersed, where more efficient dispersing could be defined as reaching the same degree of homogeneity earlier in the dispersion process, or reaching a higher degree of homogeneity at the same duration of dispersion.

Figure 10A:
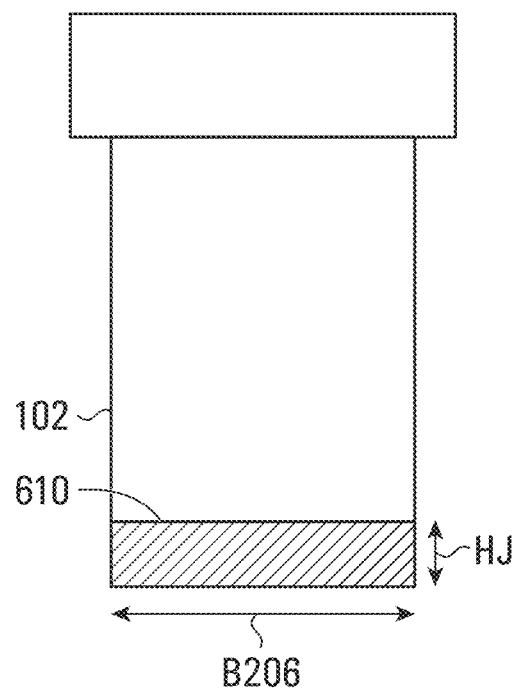
FIG. 10A shows a cross-sectional view of jar which contains a specific amount of composition, in accordance with an implementation of the present invention.
Figure 10B:
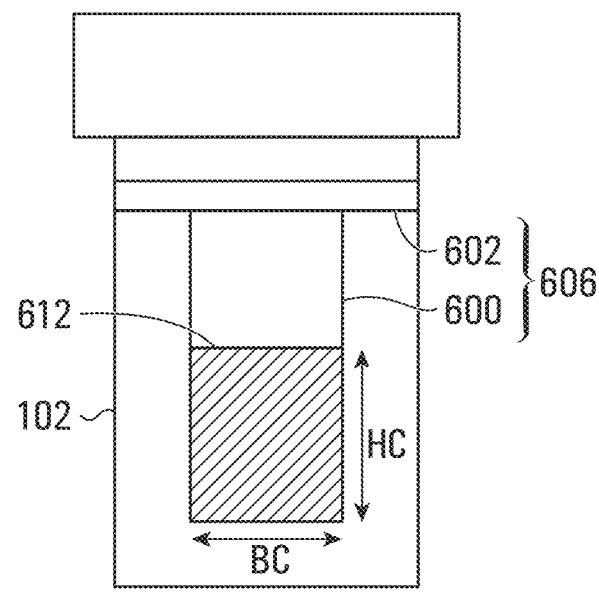
FIG. 10B shows a cross-sectional view of container placed inside jar, where the container contains the same specific amount of composition as in FIG. 10A, in accordance with an implementation of the present invention.

With continued reference to FIG. 10A, there is shown an example quantity of composition 610 placed in the jar 102 and with reference to FIG. 10B, the same quantity of composition 612 placed in the container 600 that is secured to the jar 102 by the adapter 602. The height dimension occupied by the composition 610 in the jar 102 is given by HJ and the base dimension is given by the bottom inside diameter 206 of the jar 102, which can be referred to as B206. Thus, the HBR associated with the quantity of composition 610 is HJ/B206 for the jar 102. Turning now to the case of the container 600, it is seen that the height dimension occupied by the composition 612 in the container 600 is given by HC and the base dimension is given by the bottom inside diameter of the container 600, which can be referred to as BC. Thus, the HBR associated with the quantity of composition 612 is HC/BC for the container 600.

It should be apparent, therefore, that for the same quantity of pharmaceutical composition, the HBR for the container 600 is greater than for the jar 102. In fact, the smaller the quantity of the composition, the greater the difference in HBR between the jar 102 and the container 600. This increase in HBR from the jar 102 to the container 600 (for the same quantity of composition) is a function of the ratio between the base area of the jar and the base area of the container. For certain quantities of ingredients and certain container sizes, the HBR will fall outside a desired range (e.g., 0.75 to 1.5, or 0.75 to 1.33, or even 1 to 1.25) if the composition is placed directly in the jar 102 and will be closer to, or within, the desired range, if the composition is placed in the container 600.

Another parameter that could be indicative of how efficiently the composition will be dispersed may be "percent volume occupancy" (PVO). For a quantity of composition in a vessel with a generally cylindrical internal volume, the PVO may be defined as the ratio of the height dimension occupied by the composition to the overall interior height dimension of the vessel. In the example of FIG. 10A, the PVO for the jar 102 is clearly under 20%, whereas for the container 600 in FIG. 10B it is over 50%. It should be apparent, therefore, that for the same quantity of composition, the PVO for the container 600 is greater than for the jar 102. In fact, the smaller the quantity of the composition, the greater the difference in PVO between the jar 102 and the container 600.

Expressed another way, the use of the container 600 with the jar 102 can allow a composition that occupies ½ of the jar capacity to have an HBR between 0.75 and 1.5 (or between 0.75 and 1.33, or even between 1 and 1.25) when the composition is placed into the container 600.

As such, it may be more desirable to utilize a container 600 having a certain size, rather than the jar 102, in order to process smaller quantities of composition, so as to obtain a more suitable HBR or PVO. This is especially the case when the quantity of the composition to be processed is less than half the capacity of the jar 102 or less than a quarter of the capacity of the jar or less than a tenth of the capacity of the jar.

To allow the use of a smaller container with improved HBR or PVO, the adapter 602 may help reduce or prevent rattling and other instabilities within the jar 102 during processing by the apparatus 100. The adapter 602 is disposed between the interior of the jar 102 and the exterior of the container 600. When the adapter 602 is attached to the container 600, it can be inserted into and removed from the jar 102, and for this reason the container 600 together with the adapter 602 may be referred to as a removable "containing system" 606.

Different embodiments of the adapter 602 may be provided for different versions of the container 600. Thus, depending on whether the container 600 is a compounding bottle with a nozzle (such as container 402) or a cylindrical bottle (such as container 502A), the adapter 602 may take on a different shape or structure. This is now described in some detail.

Figure 11:
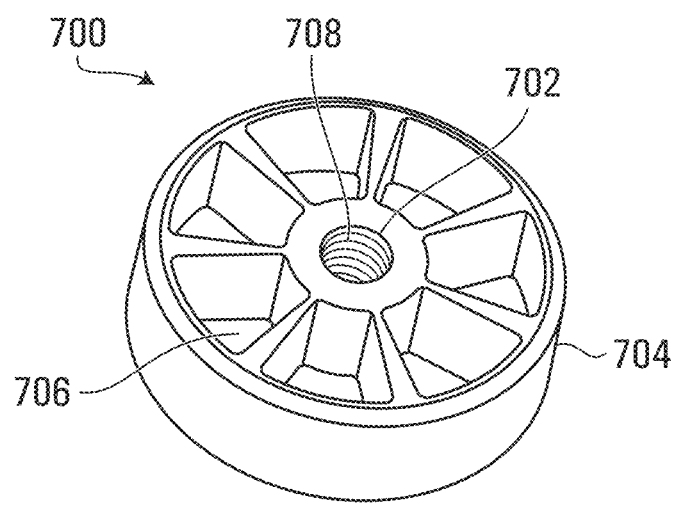
FIG. 11 shows a top isometric view of an adapter for use with a container for use with the system of FIG. 6, in accordance with a first implementation of the present invention.

FIG. 11 shows a non-limiting embodiment of an adapter 700 for use with a nozzled container, such as the container 402. The adapter 700 may be in the form of a disk with an aperture 702 in the center thereof. The adapter 700 occupies an area in 3-dimensional space that is outlined by an envelope 704. The adapter 700 may be populated with voids 706 that reduce the weight of the adapter and therefore the density of the adapter 700 vis-à-vis the envelope 704 that it occupies. In some embodiments, the voids 706 are evenly spaced circumferentially and give the adapter 700 the appearance of a wheel.

Figure 12:
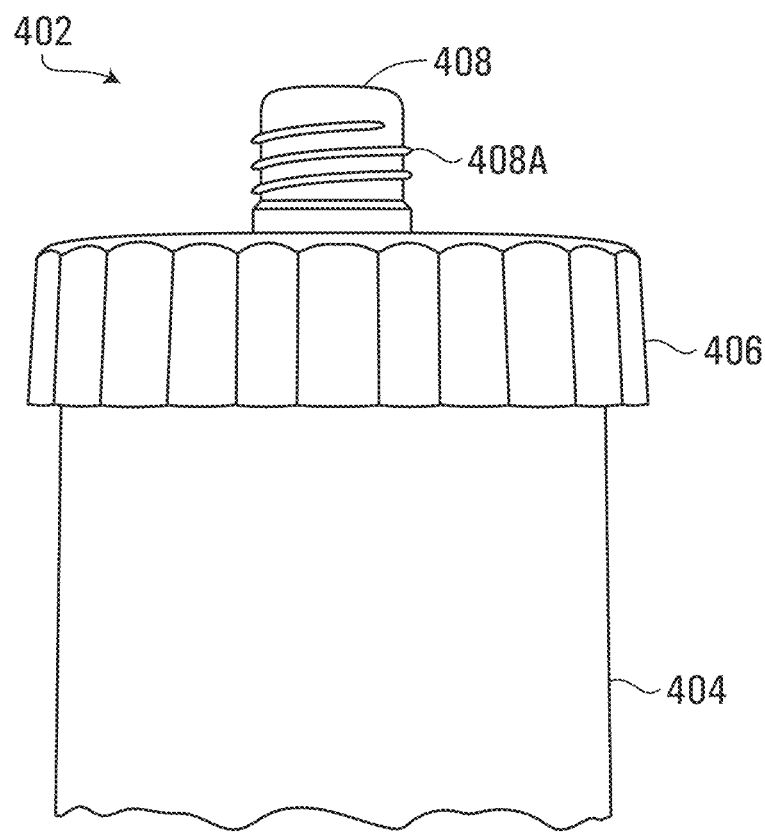
FIG. 12 shows a side view of the container of FIG. 8, including details of the external threads on the nozzle of the container, in accordance with an implementation of the present invention.

In some embodiments, the adapter 700 is configured to attach to a container with a nozzle, such as the container 402 previously described. To this end, the aperture 702 has a dimensionality that is selected according to the configuration of the nozzle 408 of the container 402. In particular, FIG. 12 shows details of the external threads 408A on the nozzle 408 and the adapter 700 shown in FIG. 11 may accordingly include internal threads 708 in the area of the central aperture 702 so as to enable the adapter 700 to be screwed onto the nozzle 408. It should be appreciated that when nozzled containers of different sizes all share the same design of the nozzle 408, the same adapter 700 may be used for these various containers.

Figure 13:
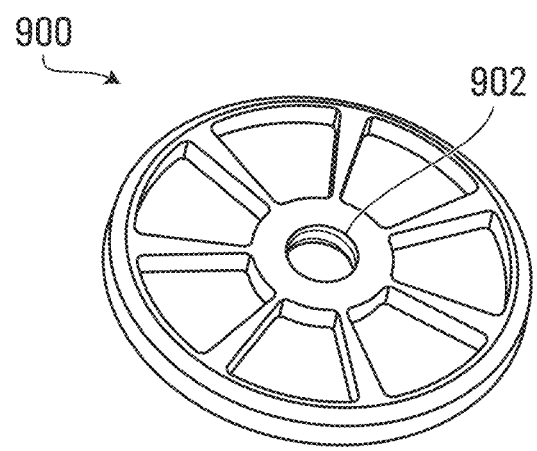
FIG. 13 shows a top isometric view of a variant of the adapter of FIG. 11, in accordance with a second implementation of the present invention.

FIG. 13 shows an alternative non-limiting embodiment of an adapter 900, also including an aperture 902, but where the aperture 902 is made slightly wider than the aperture 702 and in fact slightly wider than the maximum diameter of the external threads 408A of the nozzle 408. However, the width of the aperture 902 is smaller than the external diameter 410A of the cap 410 (shown in FIG. 8). Thus, when the adapter 900 is placed over the nozzle 408 and then the cap 410 is threaded onto the nozzle 408, the adapter 900 ends up being enclosed between the cover 406 and the cap 410.

The adapters 700, 900 may have a thickness of between 0.5 mm and 5 mm, or even between 1 and 3 mm, although it may be thinner in some embodiments and thicker in others. Other design considerations include (i) that there be sufficient threading 408A in the nozzle 408 to allow the cap 410 to be securely mounted thereto and (ii) once the cap 410 is mounted to the nozzle 408 (on top of the adapters 700, 900) and a containing system 606 is positioned in the jar 102, that there be sufficient clearance (the minimum being zero, i.e., flush) between the top of the cap 410 and the underside of the lid 106 of the jar 102 once the lid 106 has been mounted to the mouth 108 of the jar 102.

To mitigate lateral rattling, the containing system 606 should fit frictionally within the jar 102. To this end, with reference to FIG. 14, the adapter 602 is seen as having a cross-sectional width 1002 that is substantially equal to the cross-sectional width 108W of the mouth 108 of the jar 102. When the containing system 606 is placed into the jar 102, the maximum space between the outer edge of the adapter 602 and the inner surface 218 of the jar 102 may be less than 2 mm, in some cases less than 1 mm and in some cases less than 100 microns.

It should be appreciated that although it is important that there be sufficient clearance between the top of the cap 410 (mounted to the adaptors 700, 900) and the underside of the lid 106 of the jar 102 once the lid 106 has been mounted to the mouth 108 of the jar 102, excessive clearance could allow motion along the main axis 608 of the containing system 606 during mixing by the mixing apparatus 100. (Of course, the main axis 608 is shown as being vertical in the drawings, but in use, it is recognized that the jar 102 sits at an angle, and therefore the main axis 608 will be oblique). Excessive clearance is caused by the smaller container sizes that do not have sufficient height dimensions, such that when the adapters 700, 900 are used, the ensuing containing system 606 would still be free to travel in a piston like fashion.

Figure 15:
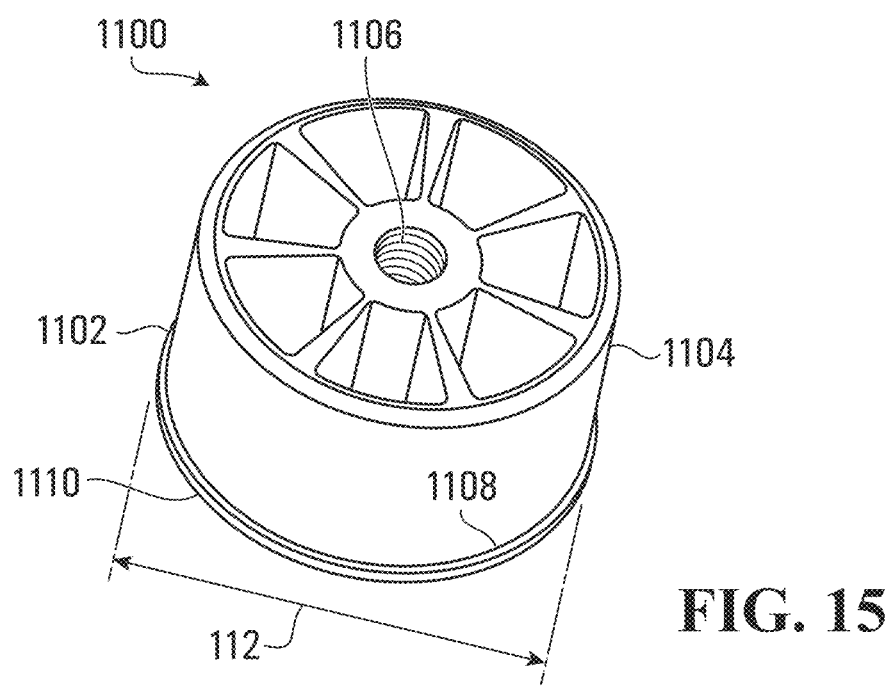
FIG. 15 shows a top isometric view of a variant of the adapter of FIG. 11, in accordance with a third implementation of the present invention.

With reference to FIG. 15, there is shown an alternative embodiment of an adapter 1100, which may be useful with smaller container sizes. The adapter 1100 includes a disk 1102 (also referred to as a second adapter portion) and a band 1104 (also referred to as a first adapter portion) that surrounds and extends upwardly from the disk 1102. The disk 1102 has a central aperture 1106 (also referred to as the recess 1106) that could be similar to the aperture 702 in FIG. 11 (which is internally threaded to engage the external thread 408A of the nozzle 408) or to the aperture 902 in FIG. 13 (which is wider than the nozzle 408). The band 1104 includes a ring 1108 and, optionally, a lip 1110. The ring 1108 has an outside diameter 1112 than is substantially equal to the top inside diameter 202 of the jar 102. The lip 1110 extends radially outwardly beyond the ring 1108, but only slightly, as it is configured to rest on the mouth 108 of the jar 102 without protruding radially from the jar 102. The lip 1110 therefore also has a circular shape and its maximum diameter corresponds to the outer diameter 220 of the jar body 102. The ring 1110 therefore fits frictionally into the jar 102, descending towards the middle section 214 of the jar 102, while the lip 1110 acts as a stopper to prevent the ring 1108 from being pushed too deep into the jar 102. The lid 106 may still be placed onto the mouth 108 of the jar 102, although in reality it is being placed onto an upper surface of the lip 1110. Thus, the height of the jar is increased by no more than 1 or 2 mm, on top of which the lid 106 is positioned.

Figure 16:
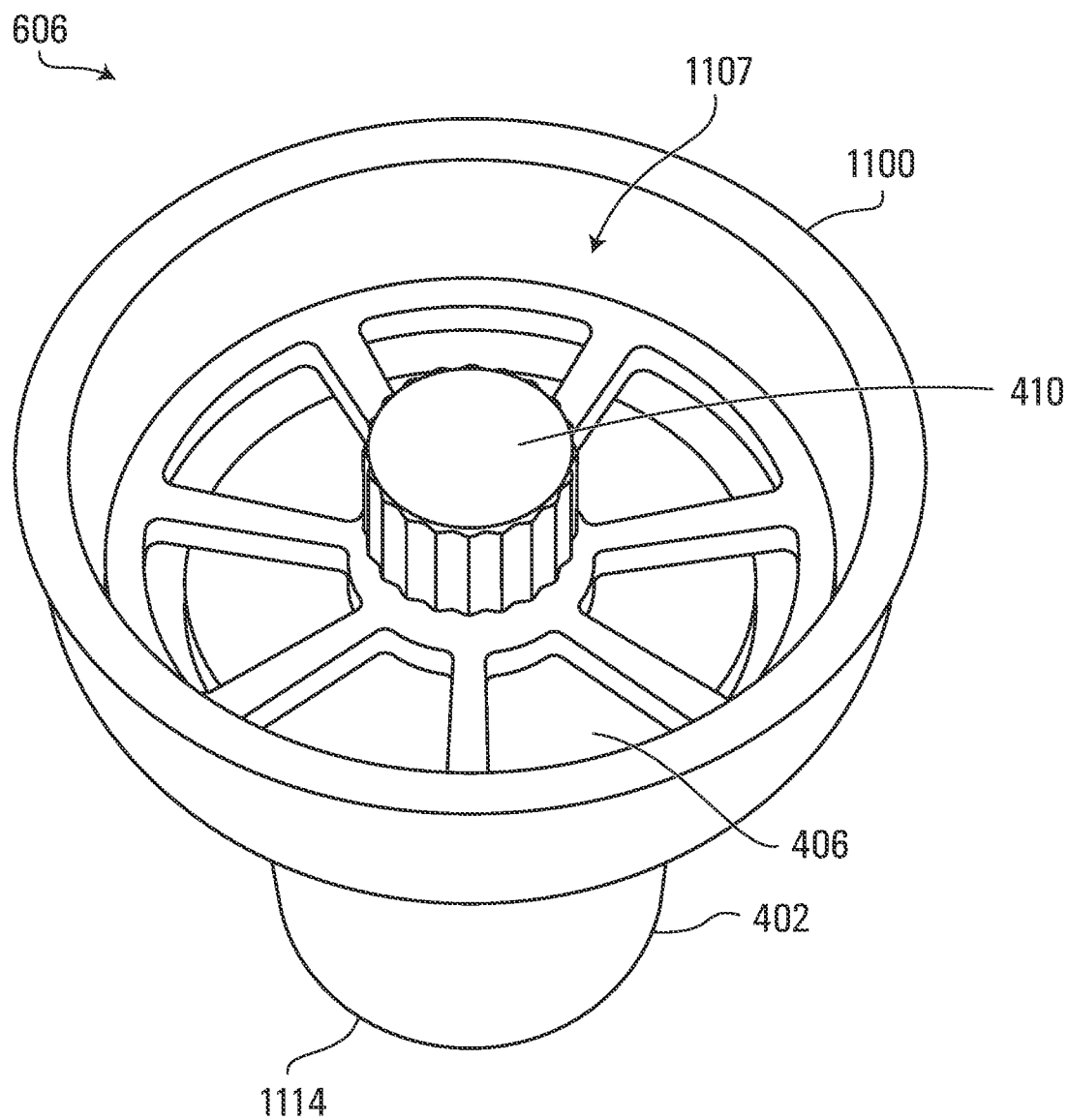
FIG. 16 shows a top isometric view of containing system which includes the adaptor of FIG. 15 mounted onto the container of FIG. 8, in accordance with an implementation of the present invention.

As shown in FIG. 16, the adapter 1100 may be attached to the container 402 between the top surface of the cover 406 and the bottom surface of the cap 410 so that the cap 410 fits within a cavity 1107 of the adapter 1100. When the containing system 606 is placed in the jar 102, a range of smaller sizes of containers 402 can be secured in place by the adapter 1100. In particular, assuming that they all share the same nozzle 408 (also referred to as a second container part) and cap 410 (also referred to as a first container part) configuration, the largest size container 402 will be the one whose bottom 1114 touches the bottom of the inside of the bottom surface of the jar 102 when attached to the adapter 1100 of FIGS. 15 and 16.

Figure 17:
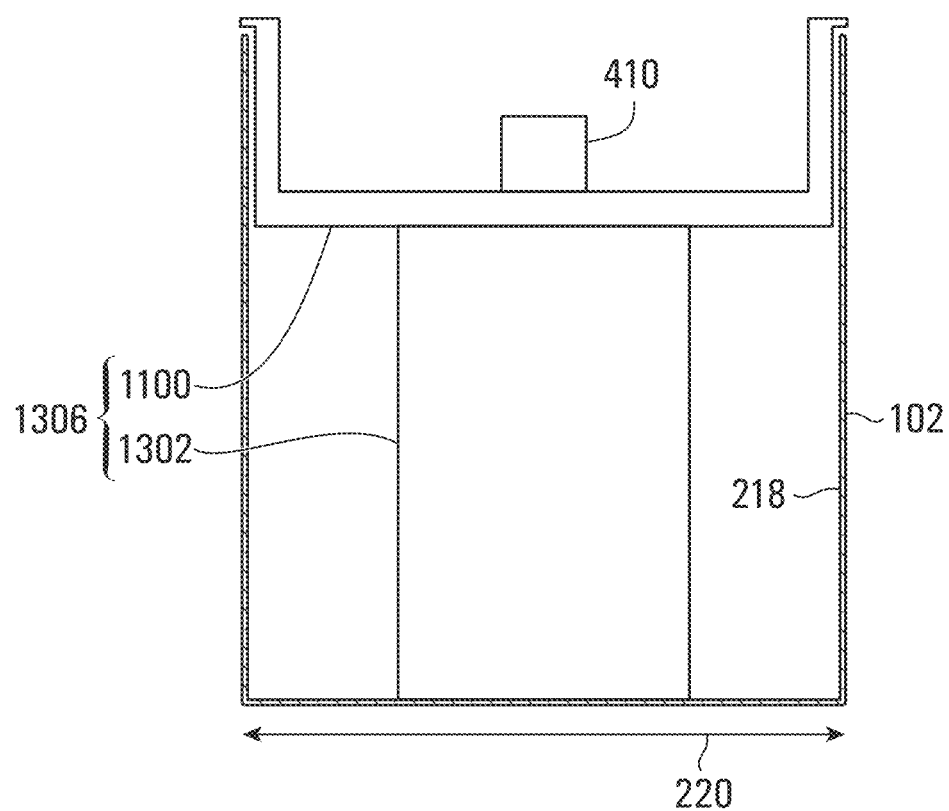
FIG. 17 shows a cross-sectional view of a containing system placed inside a jar, in accordance with an implementation of the present invention.

Thus, smaller sizes of the container 402 can be accommodated by the adapter 1100. In particular, containers having less height can be accommodated by attaching the adapter 1100 in exactly the same way. The difference is that the container will now be suspended within the jar. This is shown in the cross-sectional drawing of FIG. 17. In particular, it is seen that no direct contact exists between the container 1302 and the inner wall 218 of the jar 102. Rather, the adapter 1100 provides the only contact with inner wall 218 of the jar 102. However, this is not a requirement. For example, in other embodiments (not shown), the cap 410 that is threaded onto the nozzle 408 of the container 1302 may contact the underside of the lid 106 of the jar 102. An advantage of the adapter 1100 of FIGS. 15 to 17 may be that the same adapter 1100 can accommodate different size nozzled containers, for example, 50 ml, 30 ml or 20 ml, to name a few non-limiting possibilities.

It should be appreciated that for certain container sizes, although the container 1302 is suspended within the jar 102 at rest by the adapter 1100, during operation, there may be contact between the outer wall of the container 1302 and the inner wall 218 of the jar 102. This may be caused by the high centrifugal force exerted by the apparatus 100 on the containing system 1306 (i.e., the adapter 1100 and the container 1302, including its contents), which could temporarily deform the container 1302 and/or the adapter 1100 to a point where at least a portion surface of the container 1302 makes direct contact with the inner wall 218 of the jar 102.

In another embodiment, the container that contains the composition to be dispersed does not have a cover with a threaded nozzle. Rather, the container may be a cylindrical container with a substantially smooth and even cylindrical profile. In this case, the adapter may be configured to clamp the container from the sides.

Figure 18A:
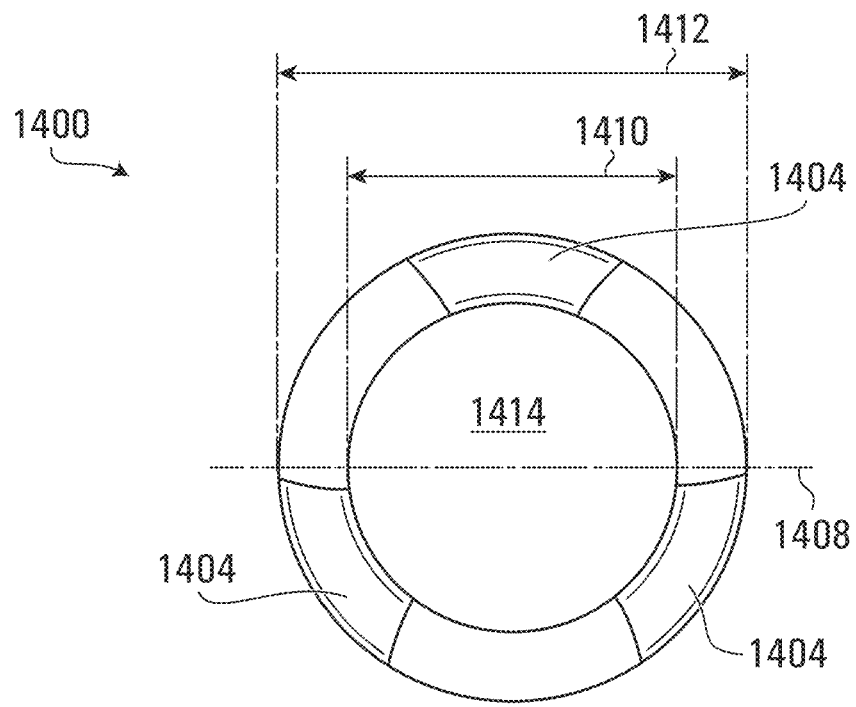
FIG. 18A shows a top view of an adaptor having three prongs for use with a container, in accordance with an implementation of the present invention.
Figure 18B:
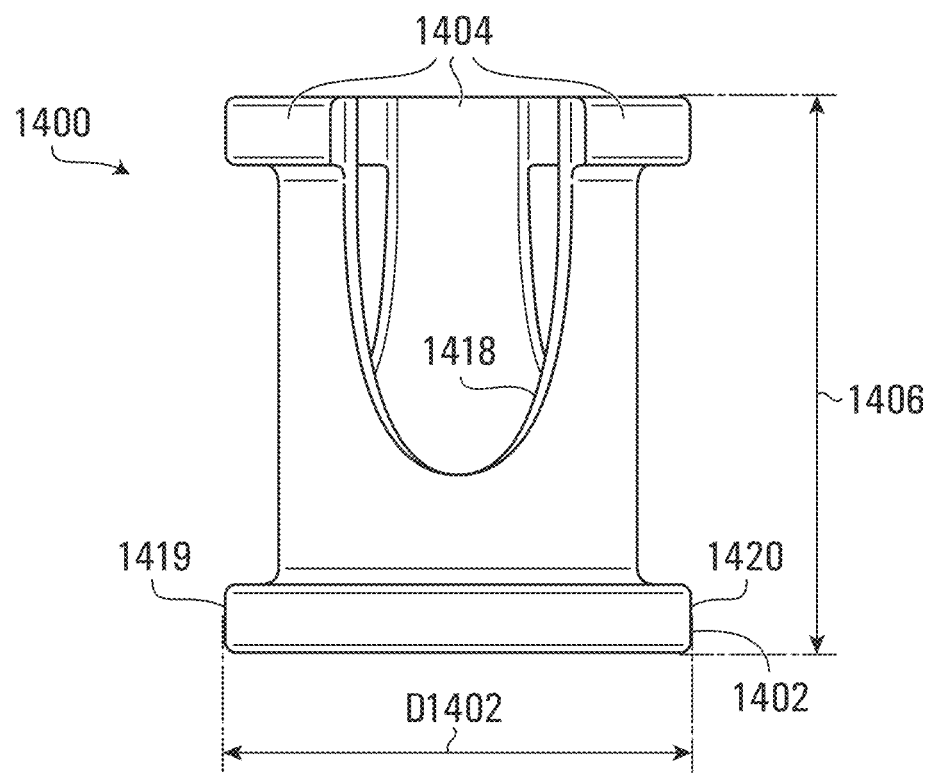
FIG. 18B shows a side view of the adaptor of FIG. 18A, in accordance with an implementation of the present invention.
Figure 19:
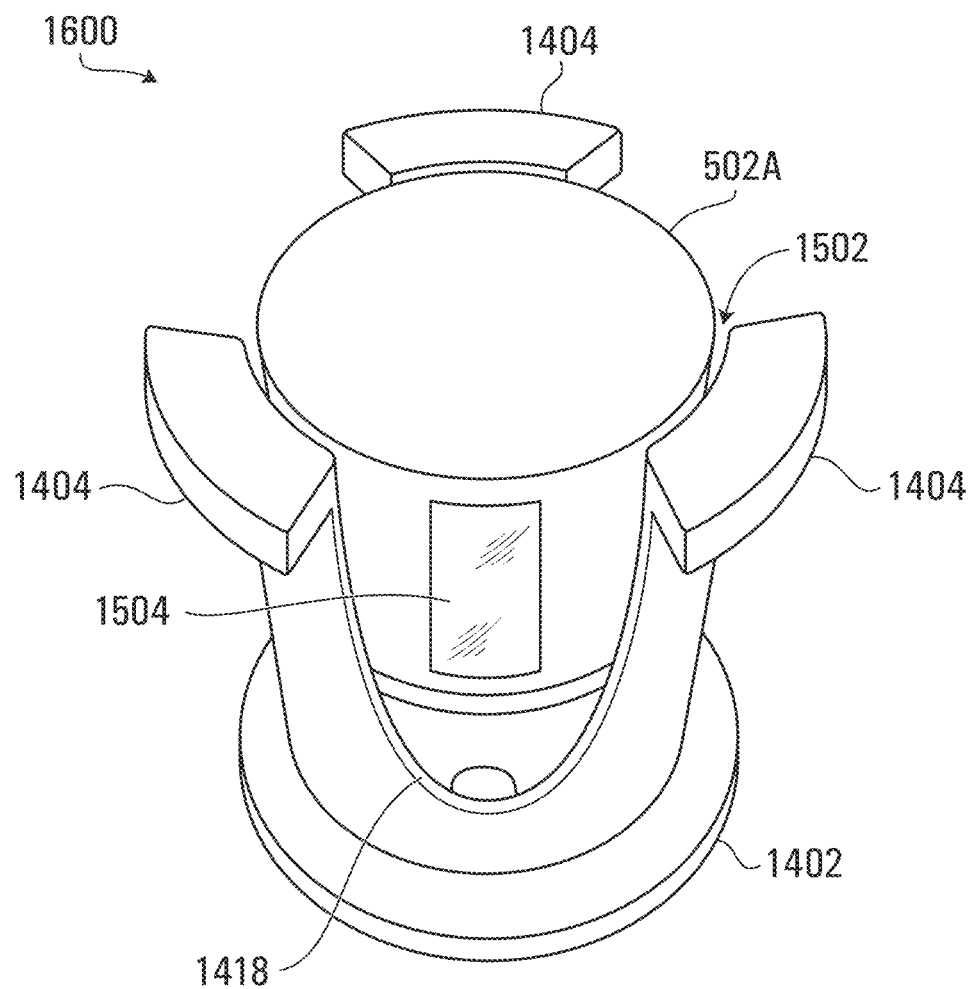
FIG. 19 shows a top isometric view of adaptor of FIG. 18A in which is located the container, in accordance with an implementation of the present invention.

Specifically, FIGS. 18A and 18B each show an embodiment of an adapter 1400 at rest, including a base 1402 and a plurality of prongs 1404 distributed circumferentially. The adapter 1400 defines a central opening 1414 into which a container such as the container 502A may be inserted and surrounded by the prongs 1404. The adapter 1400 has a height dimension 1406 that may correspond substantially to the inside height of the jar 102. The prongs 1404 may be resilient and slightly outwardly biased. As such, when the adapter 1400 is at rest (outside the jar 102, as shown in FIGS. 18A and 18B), the prongs 1404 define a substantially band-like cross-section 1408 with an inside width 1410 and an outside width 1412. The inside width 1410, near the top of the adapter 1400, is slightly greater than an outside diameter 508 of the container 502A for which it is configured. Thus there is a gap 1502 as shown in FIG. 19. Also, at rest, the outside width 1412, near the top of the adapter 1400, is slightly greater than the top inside diameter 202 of the jar 102 (see FIG. 1). As will now be explained, there is enough resiliency in the prongs 1404 so that they may be compressed radially inwardly.

Figure 20:
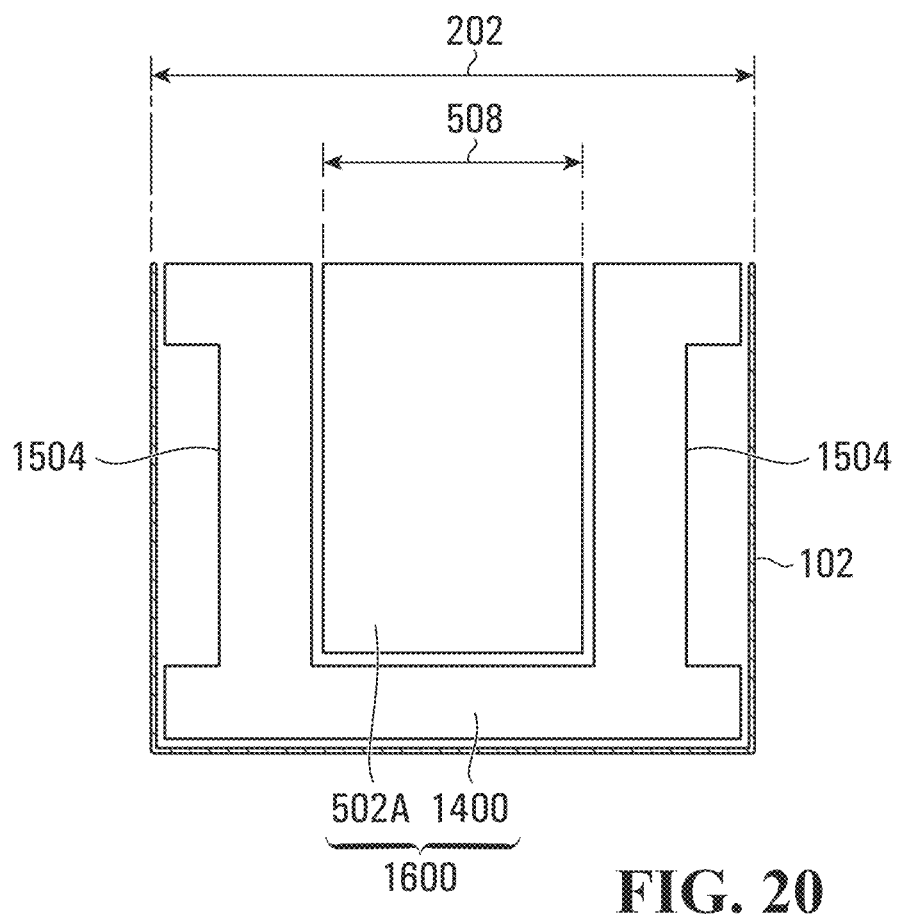
FIG. 20 show a cross-sectional view of the containing system placed inside a jar, in accordance with an implementation of the present invention.

In particular, FIG. 20 shows a cross-sectional view of the adapter 1400 when the containing system 1600 (including the adapter 1400 and the container 502A) is placed inside the jar 102. Here, the prongs 1504 are compressed inwardly (towards the center) and the inside width 1410 of the band-like cross-section 1408 formed by the prongs 1404 is now substantially the same as the outside diameter 508 of the container 502A and the outside width 1412 of the band-like cross-section formed by the prongs 1404 is now substantially the same as the top inside diameter 202 of the jar 102. As a result, the container 502A is more snugly maintained by the prongs 1404 within the central opening 1414.

The number of prongs 1404 is not particularly limited. The embodiment of FIGS. 18A and 18B show the adapter 1400 having three prongs 1404. However, in other embodiments, such as in FIG. 21, the adapter 1700 has four prongs 1704.

Figure 21:
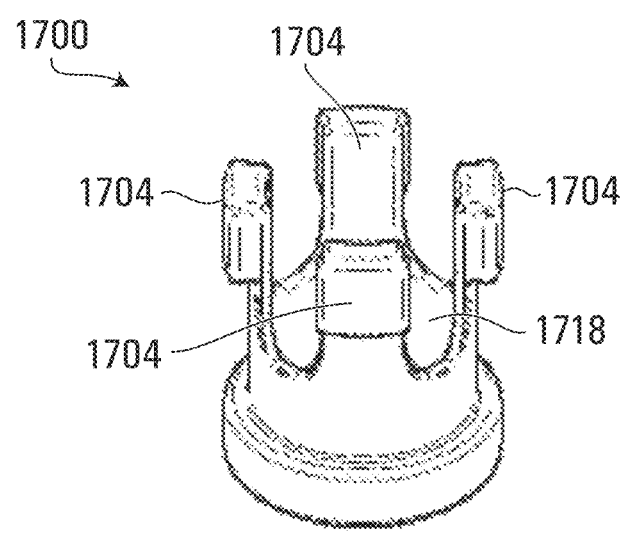
FIG. 21 shows a top isometric view of an adaptor having four prongs for use with a container, in accordance with an implementation of the present invention.

To limit the amount of material used to make the adapter 1400, 1700, the adapter may include cut-outs 1418, 1718 between the prongs 1404, 1704. The cut-outs have a depth defined as a relative distance occupied by the cut-outs in a height dimension of the adapter compared to the overall height of the respective adapter 1400, 1700. For example, for the adapter 1700 for which a side elevational view is shown in FIG. 21, the depth of the cut-outs 1718 is over 50%. In other embodiments, such as for the adapter 1400 for which a side elevational view is shown in FIG. 18, the depth of the cut-outs 1418 may be over 60%, over 70% or even over 80%. In further embodiments, it may be between 40% and 50%.

The cut-outs 1418, 1718 may take on different shapes and configurations. In FIGS. 18B and 21, the cut-outs 1418, 1718 have a deep parabolic shape. In other embodiments, the cut-outs may have a more square-like (or rectangular) appearance.

In certain embodiments, as shown in FIG. 19, the container 502A may include a vertical viewing window 1504 that allows a user to see a level to which the container 502A is filled. Accordingly, the cut-outs 1418 may be shaped so as to allow at least part of the viewing window 1504 to be unobstructed.

Figure 14:
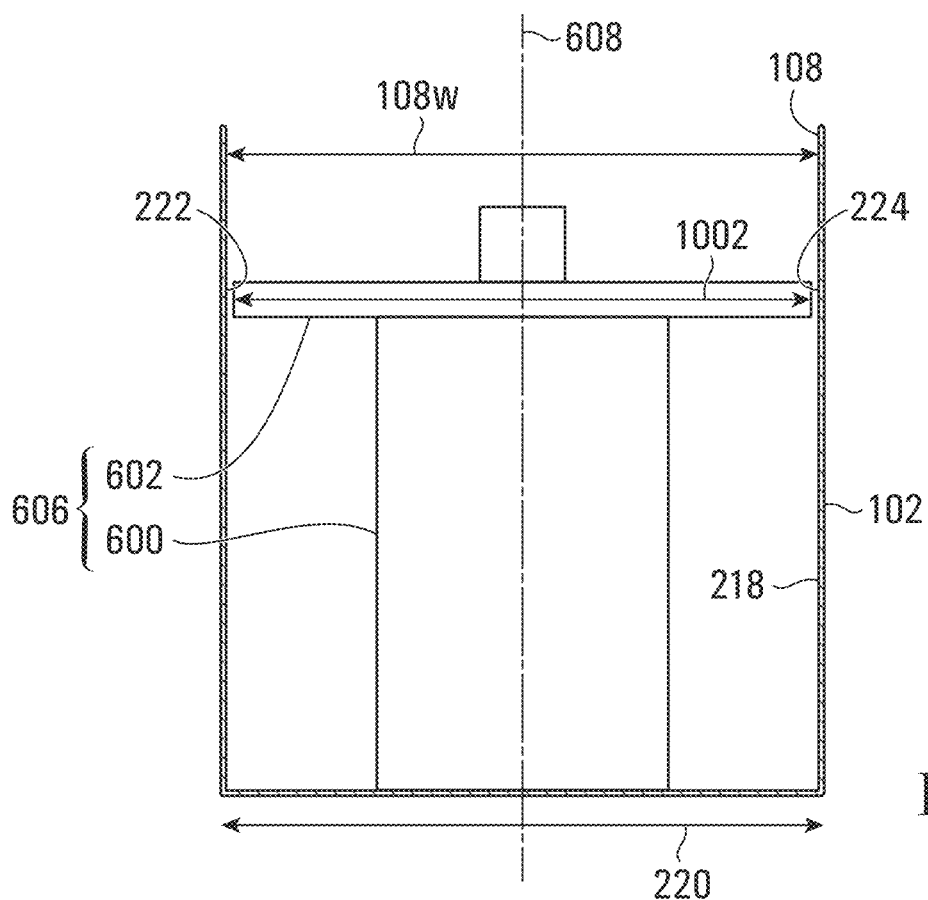
FIG. 14 shows a cross-sectional view of container secured to an inside surface of a jar via an adaptor, in accordance with an implementation of the present invention.

Turning back to FIG. 18, with additional reference to FIG. 14, the base 1402 of the adapter 1400 may be circular and may have a diameter D1402 that is substantially identical to the top inside diameter 202 of the jar 102, or even slightly greater than it (e.g., corresponding to the middle inside diameter 204 or by up to 1 mm or even 2 mm larger). Thus, aligning the base 1402 of the adapter 1400 with the mouth 108 of the jar 102 may make it difficult or even impossible to fit the adapter 1400 into the jar 102. Thus, a different technique for inserting the adapter 1400 into the jar 102 may be required. To this end, the base 1402 can be tilted and then placed onto the mouth 108 of the jar 102, such that only two diametrically opposite extremities 1419, 1420 of the base 1402 are in contact with the inner surface 218 of the jar at respective contact points 222, 224 of the adapter 1400. The adapter 1400 is then urged into the jar, which causes a very slight expansion of the width of the mouth 108, while resulting in a contraction of the mouth elsewhere between the two aforementioned contact points 222, 224. However, since the adapter 1400 is not in contact with these contracting regions, the jar 102 is allowed to flex, and thus allows the adapter 1400 to slip into the jar 102. Once the two contact points 222, 224 of the adapter 1400 pass the top section 212 of the jar 102 (which has the smallest width, namely the top inside diameter 202) and move to the middle section 214 of the jar 102 (which has the second-smallest width, namely the middle inside diameter 204), the mouth 108 of the jar 102 returns back to its original shape, which may be circular.

It should be appreciated that in the case of the container 502A, with a cylindrical exterior shape, the actuator 506 may be provided so that the mixed composition can be dispensed to an end user without the need for transfer into a separate dispenser. Of course, the actuator 506 takes up part of the headroom available between the container 502A and the underside of the lid 106, thus limiting the volume of the composition that can be placed in the body 504 for mixing. Thus, it is possible to provide a container consisting primarily of the body 504 but without the actuator 506. In this case, a temporary cap (not shown) could be fitted on the container body 504, with the temporary cap being relatively short (a height less than that of the actuator 506) and having a maximum width that is no wider than the body 504 of the container 502A. After mixing, the temporary cap may be removed, and replaced with the actuator 506. Because the temporary cap can be designed with a smaller height dimension than the actuator 506, higher (i.e., more voluminous) containers may be accommodated.

Those ordinarily skilled in the art will appreciate that further improvements may be made to the design of the adapter. In particular, in the case where an adapter is designed that has a maximum width that is less than the width of the jar, rotational motion of the jar may induce slippage in the containing system (which includes the adapter and the container). The amount of slippage may further be a function of the dimensions of the container and the weight and/or volume of the composition contained therein. To reduce slippage, various possible anti-slippage mechanisms may be provided, depending on operational requirements.

Figure 22:
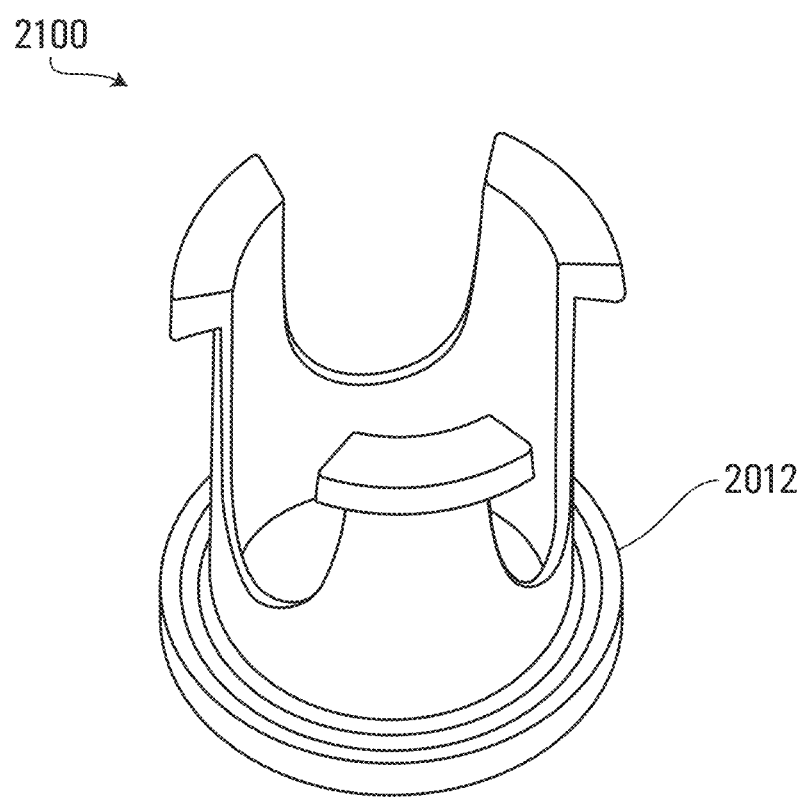
FIG. 22 shows a top isometric view of adaptor with a rubberized exterior peripheral band 2012, in accordance with an implementation of the present invention.
Figure 23A:
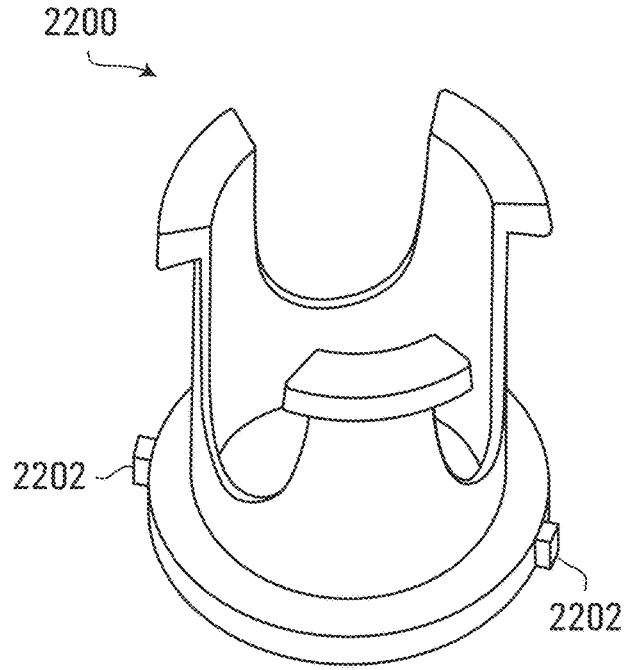
FIG. 23A shows a top isometric view of adaptor with a retention element on the base of the adaptor, in accordance with an implementation of the present invention.
Figure 23B:
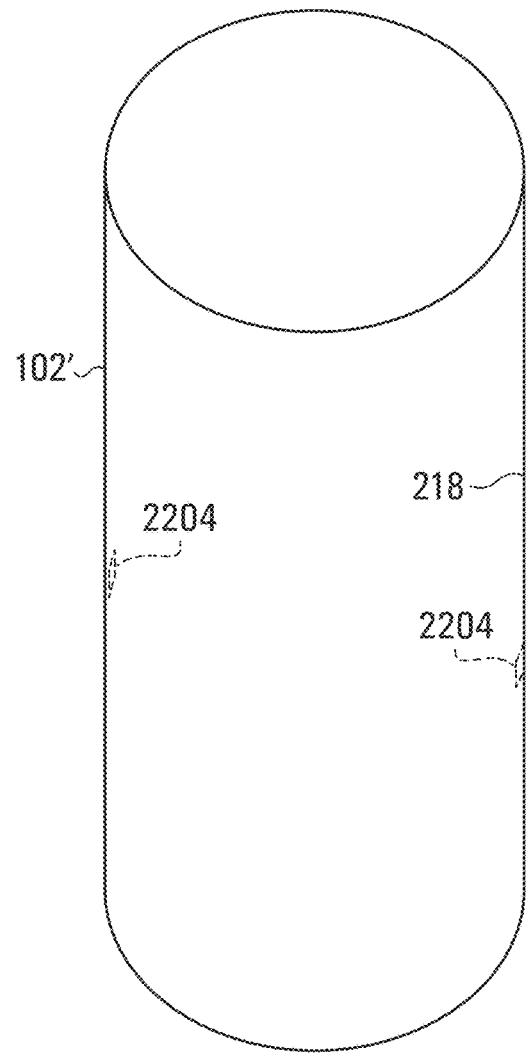
FIG. 23B shows a cross-sectional view of a jar having a retention element on the inside surface thereof corresponding to the retention element on the adaptor of FIG. 23A, in accordance with an implementation of the present invention.

Firstly, FIG. 22 shows an adapter 2100 fitted with a rubberized exterior peripheral band 2012. In another example, as shown in FIG. 23, the inner surface 218 of the jar 102 may be provided with an engaging element 2202 and an adapter 2200 may be provided with a complementary engaging element 2204 that engages with the engaging element 2202. For example, one of the engaging elements 2202, 2204 may be a slot, while the other one of the engaging elements 2202, 2204 may be a protrusion or pin. Of course, many other forms of complementary engaging elements may be devised that inhibit rotational motion of the adapter 2200 and/or the containing system within the jar 102.

Figure 24:
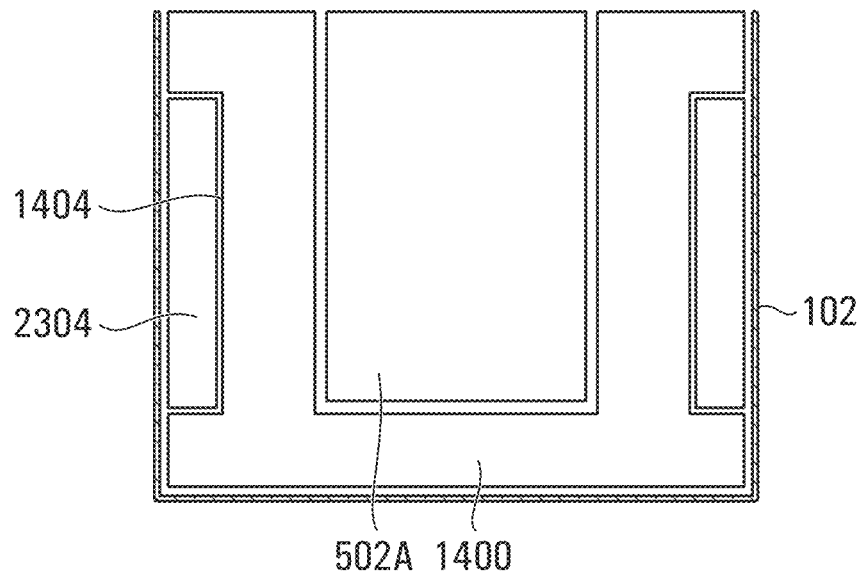
FIG. 24 shows a cross-sectional view of adaptor of FIG. 18A receiving the container and located inside jar, which has a heat conductive material located in between the prong and the inside surface of the jar, in accordance with an implementation of the present invention.

Those skilled in the art will recognize that further improvements may be made to enhance performance during the herein described bladeless dispensing pattern process. For example, in the event that the user wishes to mix a composition that gives off heat, such heat may damage the API of the composition above a certain temperature, known as the degradation temperature threshold. With additional reference to FIG. 24, it is within the scope of the present invention to delay reaching this temperature by providing a heat conductive material 2304 between the adapter 1400 (or 1700) and the inner surface 218 of the jar 102. The heat conductive material 2304 may serve to dissipate heat better than simply the air that would ordinarily occupy this space. In some cases, a thermally conductive foil, foam or gel may be provided, as are made available by Fischer Elektronik GmbH, Lüdenschied, Germany.

Figure 25:
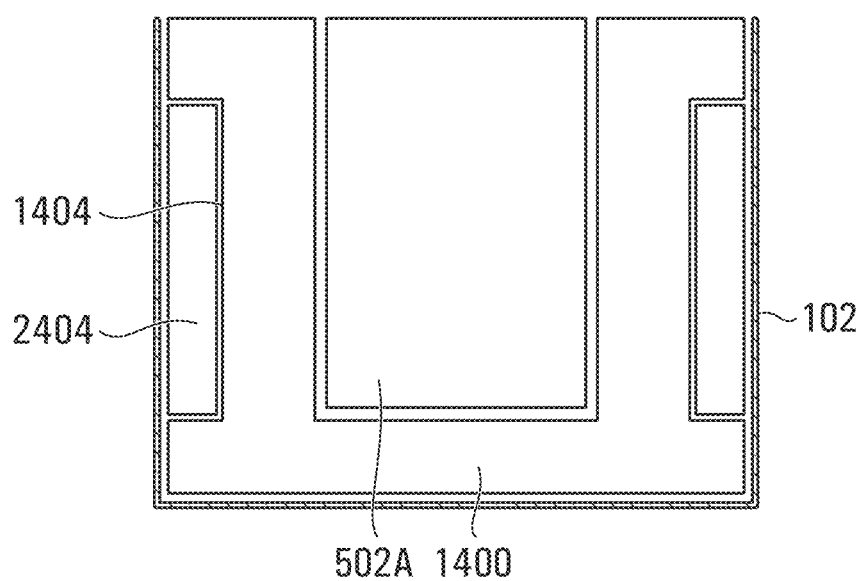
FIG. 25 shows a cross-sectional view of adaptor of FIG. 18A receiving the container and located inside a jar, which has a thermally insulating material located in between the prong and the inside surface of the jar, in accordance with an implementation of the present invention.

In another embodiment, rather than a thermally conductive material, it may be desirable to place a thermally insulating material 2404 between the adapter 1400 and the inner surface 218 of the jar 102, as shown in FIG. 25. The insulating material 2404 may serve as a barrier to heat leaving the container 502A, which will result in an increase in the temperature within the container 502A. As a result, it may be possible to melt the compound that is undergoing the herein described bladeless dispensing pattern process within the container 502A, thereby leading to a state change of the composition through novel use of the apparatus 100. Moreover, the use of the heat insulating material 2404 may accelerate the melting process, i.e., shortening the time it takes to melt the composition, thus leading to a more efficient usage of the apparatus 100.

Figure 26:
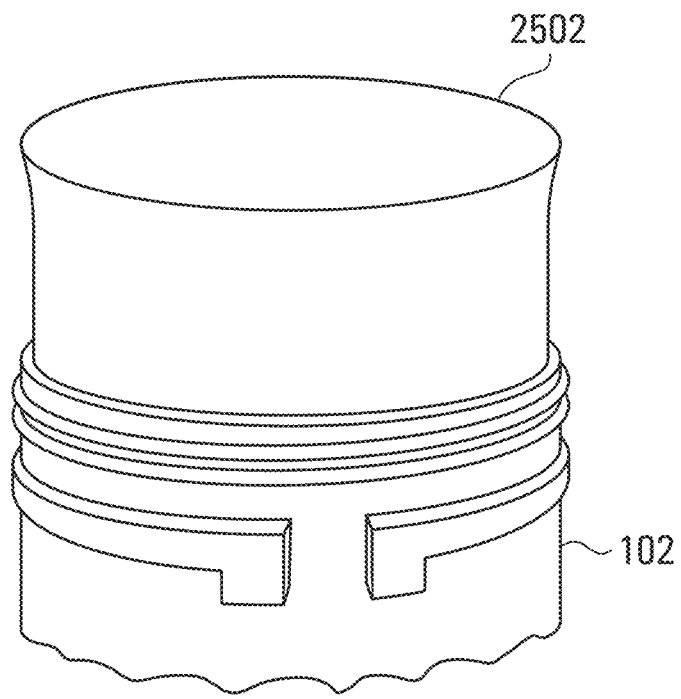
FIG. 26 shows a side elevation of insert that may be removably positioned within the jar, in accordance with an implementation of the present invention.
Figure 27:
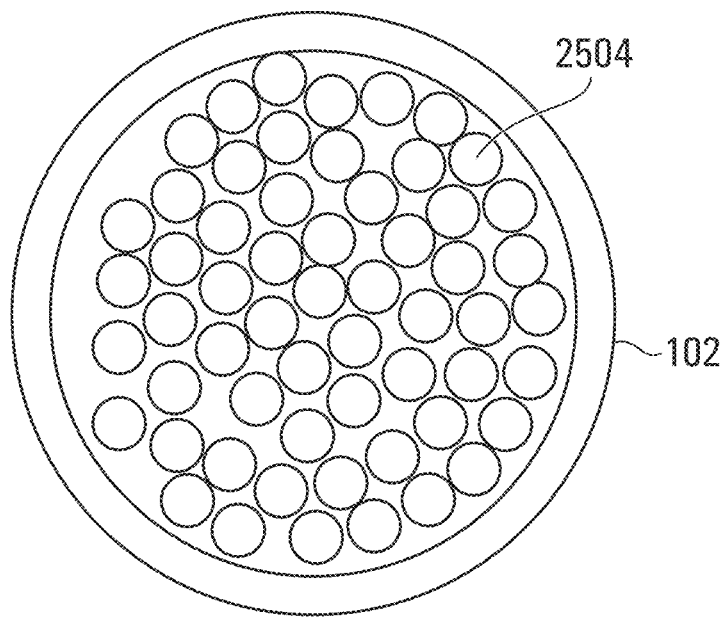
FIG. 27 shows a top view of a jar containing grinding media, in accordance with an implementation of the present invention.

With reference to FIG. 26, there is shown an insert 2502 that may be removably positioned within the jar 102. The insert 2502 has the form of a metallic cup with a bottom, but in other embodiments it may be a bottomless sleeve. The insert 2502 may be made of hardened steel, stainless steel, tungsten carbide, agate, sintered aluminium oxide, silicon nitride or zirconium oxide, for example. Also provided are grinding media 2504 such as balls or pellets made of similar materials, as shown in FIG. 27. In an embodiment, the insert 2502 is friction fitted to the inner surface 218 of the jar 102 and may have a thickness of between 10 and 100 mils, although other thicknesses are possible. In another embodiment, the insert 2502 may have a smaller volume and may be held in place within the jar by an adapter, which may be similar to the previously described adapters. As a result, it may be possible to grind ingredients of the compounding composition through novel use of the apparatus 100.

Definitions

Compounding activities, in the context of the present specification, also applies to combining, mixing or altering ingredients for a cosmetic composition which may include active over the counter (OTC) ingredients or prescription pharmaceutical ingredients. Within the context of the present specification, OTC and prescription ingredients are encompassed by the expression "active pharmaceuticals ingredients" (i.e., "API").

Examples of active pharmaceuticals ingredients (APIs) include, but are not limited to, antibiotics, analgesics, vaccines, anticonvulsants; antidiabetic agents, antifungal agents, antineoplastic agents, antiparkinsonian agents, antirheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroid, anti-hyperthyroid, anti-asthmatics and vertigo agents.

In certain embodiments, the API is a poorly water-soluble drug or a drug with a high melting point.

The API may be found in the form of one or more pharmaceutically acceptable salts, esters, derivatives, analogs, prodrugs, and solvates thereof. As used herein, a "pharmaceutically acceptable salt" is understood to mean a compound formed by the interaction of an acid and a base, the hydrogen atoms of the acid being replaced by the positive ion of the base. Non-limiting examples of pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate. Another method for defining the ionic salts may be as an acidic functional group, such as a carboxylic acid functional group, and a pharmaceutically acceptable inorganic or organic base. Non-limiting examples of bases include, but are not limited to, hydroxides of alkali metals such as sodium, potassium and lithium; hydroxides of calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

The APIs may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot.

For the purpose of the present disclosure, the pharmaceutically acceptable excipient, diluent or carrier may be a solid, semi-solid (more or less viscous fluid) or fluid (for example a cream or an emulsion). The person of skill will appreciate that pharmaceutically acceptable excipients, diluents or carriers are known in the art and may include, but without being limited thereto, anti-adherents such as magnesium stearate; binders, such as saccharides and their derivatives (sucrose, lactose, starches, cellulose or modified cellulose, sugar alcohols such as xylitol, sorbitol or maltitol), proteins such as gelatins, synthetic polymers such as polyvinylpyrrolidone (PVP) or polyethylene glycol (PEG); coloring dyes or fragrance; glidants such as fumed silica, talc, and magnesium carbonate; hydrophilic or hydrophobic lubricants such as talc or silica, and fats, e.g. vegetable stearin, magnesium stearate or stearic acid; preservatives such as antioxidant vitamins or synthetic preservatives like parabens; sorbents or other desiccant; vehicles that serve as a medium for conveying the active ingredient such as petrolatum, gum base gelatin, dimethyl sulfoxide and mineral oil or commercial products such as VersaPro™ Gel, HRT™ Cream, OleaBase™ Plasticized, PLO Gel Mediflo™, Oral Mix™ or VersaPro™ cream, all from Medisca Pharmaceutique (Canada).

For the purpose of the present disclosure, the compounding compositions of the present description may be adapted for oral, rectal, vaginal, topical, urethral, ocular, or transdermal administration.

EXAMPLES

Details of specific practical implementation of the present disclosure will be further described in the following examples.

Example 1

In the following experiment, a compounding composition of 150 ml including 10% progesterone dispersed in an excipient was prepared according to the herein described superimposed revolution and rotation movements. The characteristics of the resulting composition were assessed.

In a dispersing container, 15 g of USP micronized progesterone (NDC: 0043-08, Lot: 56345/B) was levigated with 12.5 mL of ethoxy diglycol by hand. The container was then filled with 122.75 mL of pharmaceutically acceptable excipient VersaPro™ Cream (NDC: 2529-01, Lot: 56035D), and placed in a planetary mixer (Mazerustar KK-250S). The parameters for operating the superimposed revolution and rotation movements were set, including revolution, rotation and time variables. The resulting dispersed 10% progesterone composition was separated in the container into three layers, namely top (T), middle (M) and bottom (B) layers.

The progesterone concentration of each layer was determined using high performance liquid chromatography (HPLC). The person of skill will be able to determine the HPLC assay parameters without undue effort as HPLC is a known technique. The standard deviation (SD) between the progesterone concentrations of the three layers for each prepared formulation was determined. The design of experiment (DOE) was setup as a 23 full factorial design. Explanatory operating parameters included: revolution (x1), rotation (x2) and time (x3). The response variable (y1) was defined as the standard deviation (SD) between the concentrations of progesterone from three separated layers of the prepared composition in the dispersing container. Coding of these variables with respect to mixer settings are shown in Table 1.

TABLE 1

Coding of Explanatory Variables

| | KK-250S Mixer Setting | | | |
|---|---|---|---|---|
| Explanatory Variables | Low Value (−1) | Centre Point Value (0) | High Value (+1) | Coding Equation |
| Revolution, x1 | 1 | 5 | 9 | $\dfrac{x1 - 5}{4}$ |
| Rotation, x2 | 1 | 5 | 9 | $\dfrac{x2 - 5}{4}$ |
| Time, x3 | 1 (10 s) | 7 (70 s) | 15 (150 s) | $\dfrac{x3 - 8}{7}$ |

Eight experimental runs were executed at boundary conditions and three were done at centre point values as set forth in Table 2

TABLE 2

Trial parameters

| Randomized Trial Runs | | | | Mixer Setting | | | Formulation | | | Mass of Samples [g] | | |
|---|---|---|---|---|---|---|---|---|---|---|---|---|
| x1 | x2 | x3 | Trial Run # | x1 | x2 | x3 | Progesterone [g] | Ethoxy Diglycol [g] | VersaPro [g] | Top | Middle | Bottom |
| 1 | 1 | 1 | 1 | 9 | 9 | 15 | 15.035 | 12.912 | 122.574 | 48.918 | 48.311 | 41.019 |
| 0 | 0 | 0 | 2 | 5 | 5 | 7 | 15.069 | 12.956 | 122.492 | 44.109 | 45.606 | 49.642 |
| −1 | −1 | −1 | 3 | 1 | 1 | 1 | 15.037 | 12.895 | 122.009 | 49.097 | 45.395 | 52.768 |
| −1 | 1 | 1 | 4 | 1 | 9 | 15 | 15.053 | 13.052 | 122.652 | 44.340 | 46.901 | 55.213 |
| −1 | −1 | 1 | 5 | 1 | 1 | 15 | 15.048 | 12.849 | 122.816 | 50.134 | 46.522 | 51.165 |
| 1 | 1 | −1 | 6 | 9 | 9 | 1 | 15.083 | 12.826 | 122.695 | 50.382 | 50.591 | 45.714 |
| 0 | 0 | 0 | 7 | 5 | 5 | 7 | 15.030 | 12.744 | 122.454 | 49.940 | 45.959 | 5.454 |
| 1 | −1 | −1 | 8 | 9 | 1 | 1 | 15.012 | 12.778 | 122.784 | 48.311 | 44.961 | 54.641 |
| 1 | −1 | 1 | 9 | 9 | 1 | 15 | 15.024 | 12.811 | 122.705 | 48.878 | 49.262 | 48.490 |
| −1 | 1 | −1 | 10 | 1 | 9 | 1 | 15.054 | 12.725 | 122.615 | 49.342 | 49.447 | 49.141 |

Trials were randomized and the results are found in Table 3:

TABLE 3

Percent Progesterone and Standard Deviation Values for Each Formulation

| Sample # | Percent Progesterone (w/w) | Top, Middle, Bottom layers | Average Concentration (w/w) | Standard Deviation (SD) | Relative Standard Deviation (RSD) (%) |
|---|---|---|---|---|---|
| 1 | 9.0 | T | 9.3 | 0.351 | 3.77 |
| 2 | 9.3 | M | | | |
| 3 | 9.7 | B | | | |
| 4 | 9.7 | T | 9.7 | 0.300 | 3.09 |
| 5 | 9.4 | M | | | |
| 6 | 10.0 | B | | | |
| 7 | 1.2 | T | 5.9 | 4.392 | 74 |
| 8 | 6.6 | M | | | |
| 9 | 9.9 | B | | | |
| 10 | 8.2 | T | 9.5 | 2.166 | 22 |
| 11 | 8.3 | M | | | |
| 12 | 12.0 | B | | | |
| 13 | 3.3 | T | 9.4 | 10.078 | 107 |
| 14 | 3.8 | M | | | |
| 15 | 21.0 | B | | | |
| 16 | 9.7 | T | 9.5 | 0.346 | 3.64 |
| 17 | 9.1 | M | | | |
| 18 | 9.7 | B | | | |
| 19 | 9.8 | T | 9.6 | 0.208 | 2.17 |
| 20 | 9.7 | M | | | |
| 21 | 9.4 | B | | | |
| 22 | 1.1 | T | 7.8 | 8.997 | 115 |
| 23 | 4.2 | M | | | |
| 24 | 18.0 | B | | | |
| 25 | 7.1 | T | 8.8 | 3.659 | 41 |
| 26 | 6.3 | M | | | |
| 27 | 13.0 | B | | | |
| 28 | 4.2 | T | 9.1 | 8.545 | 93 |
| 29 | 4.2 | M | | | |
| 30 | 19.0 | B | | | |

The mixing process can be modeled by the following predictive cubic regression:

$$SD \text{ Percent Progesterone} = \\ 3.886 - 1.478\left(\frac{x_1-5}{4}\right) - 1.965\left(\frac{x_2-5}{4}\right) - 0.620\left(\frac{x_3-8}{7}\right) - \\ 1.025\left(\frac{x_1-5}{4}\right)\left(\frac{x_2-5}{4}\right) - 0.580\left(\frac{x_1-5}{4}\right)\left(\frac{x_3-8}{7}\right) - \\ 0.840\left(\frac{x_2-5}{4}\right)\left(\frac{x_3-8}{7}\right) + 2.176\left(\frac{x_1-5}{4}\right)\left(\frac{x_2-5}{4}\right)\left(\frac{x_3-8}{7}\right)$$

equa. (1)

In the equation (1), $x_1$ is the revolution setting, $x_2$ is the rotation setting and $x_3$ is the time setting.

Figure 28:
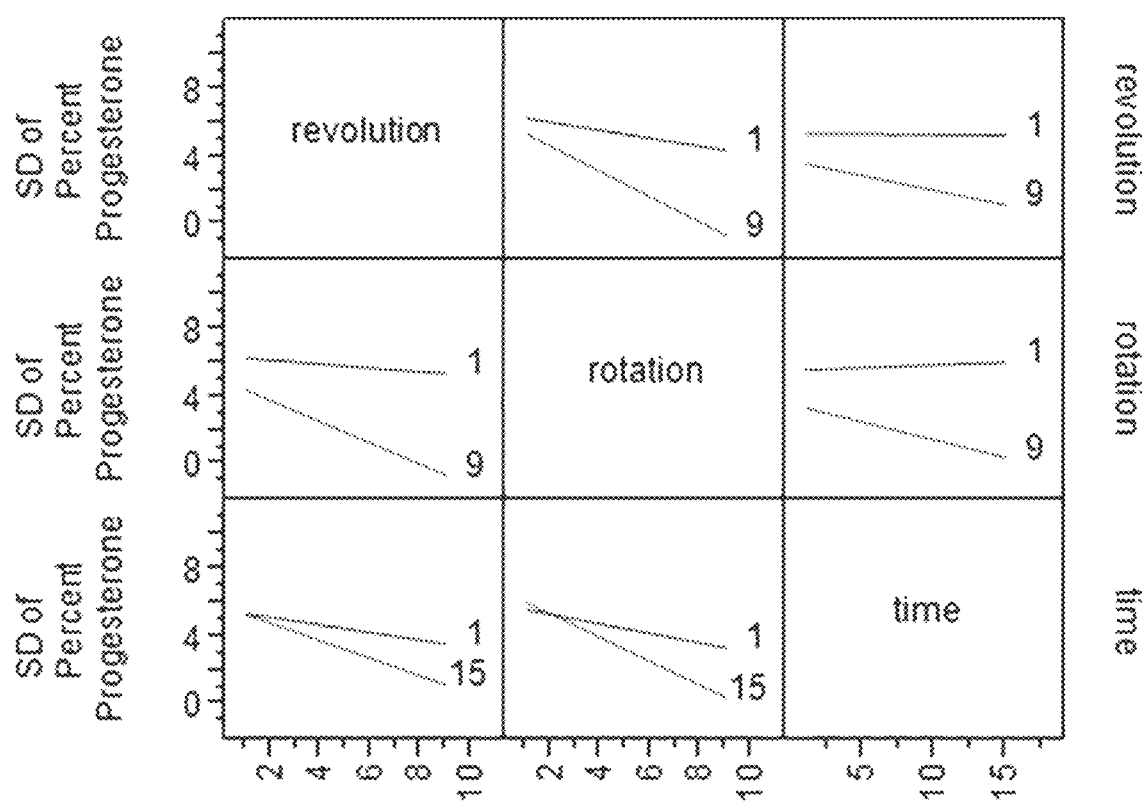
FIG. 28 represents non-limiting graphs showing the interaction profiles of combined effects on SD percent of progesterone in a composition prepared using superimposed revolution and rotation movements based on parameters varying revolution, rotation and time, in accordance with an implementation of the present invention.

The combined effect of revolution, rotation and time was found to have the greatest effect, followed by rotation and revolution. The time setting $x_3$ by itself, was not statistically significant. The interaction effects were found to be relatively influential, particularly the combination effect of all three parameters. The interaction effects can be seen in FIG. 28.

Figure 29:
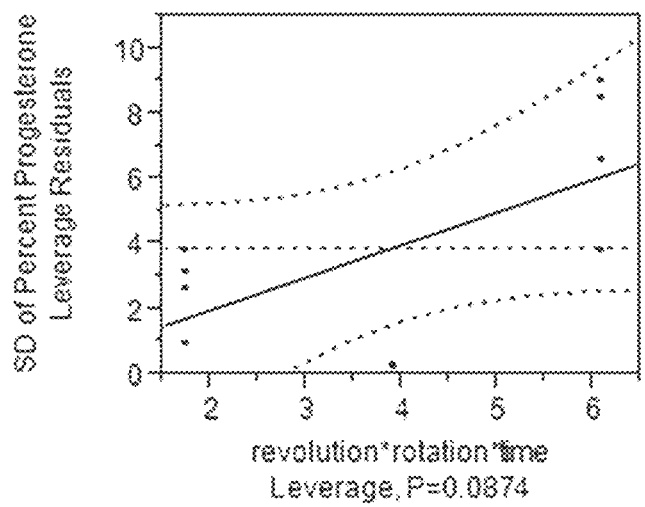
FIG. 29 represents non-limiting graphs showing leverage plots of parameters with significant effects with respect to SD of percent progesterone in a composition prepared using superimposed revolution and rotation movements based on parameters varying revolution, rotation and time, in accordance with an implementation of the present invention.
Figure 29:
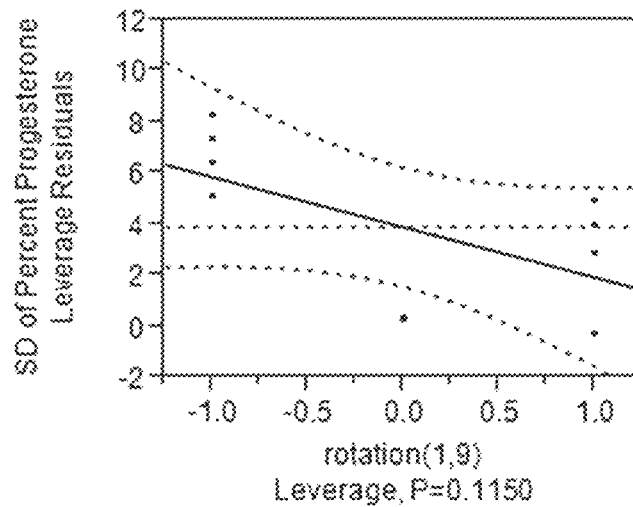
Figure 29:
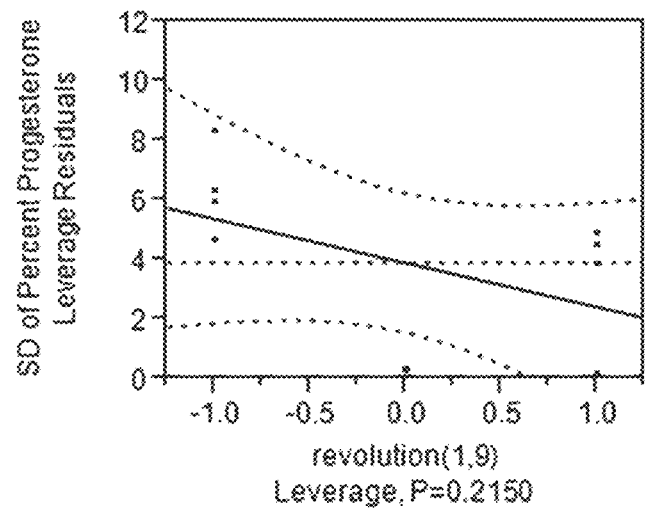

The model was reduced through an iterative method in order to better observe the parameter and interaction effects on a more statistically significant level. The codependency of the revolution, rotation and time was observed to have the strongest effect on the SD of progesterone concentration, followed by rotation and revolution. As expected, faster rotation and revolution speeds, decreased the SD of percent progesterone. These relationships are illustrated in FIG. 29.

The reduced model can be represented by the following reduced equation:

$$SD \text{ Percent Progesterone} = 3.904 - 1.478\left(\frac{x_1-5}{4}\right) - \\ 1.965\left(\frac{x_2-5}{4}\right) + 2.176\left(\frac{x_1-5}{4}\right)\left(\frac{x_2-5}{4}\right)\left(\frac{x_3-8}{7}\right)$$

equa. (2)

In equation 2, $x_1$ is the revolution setting, $x_2$ is the rotation setting and $x_3$ is the time setting.

Figure 30:
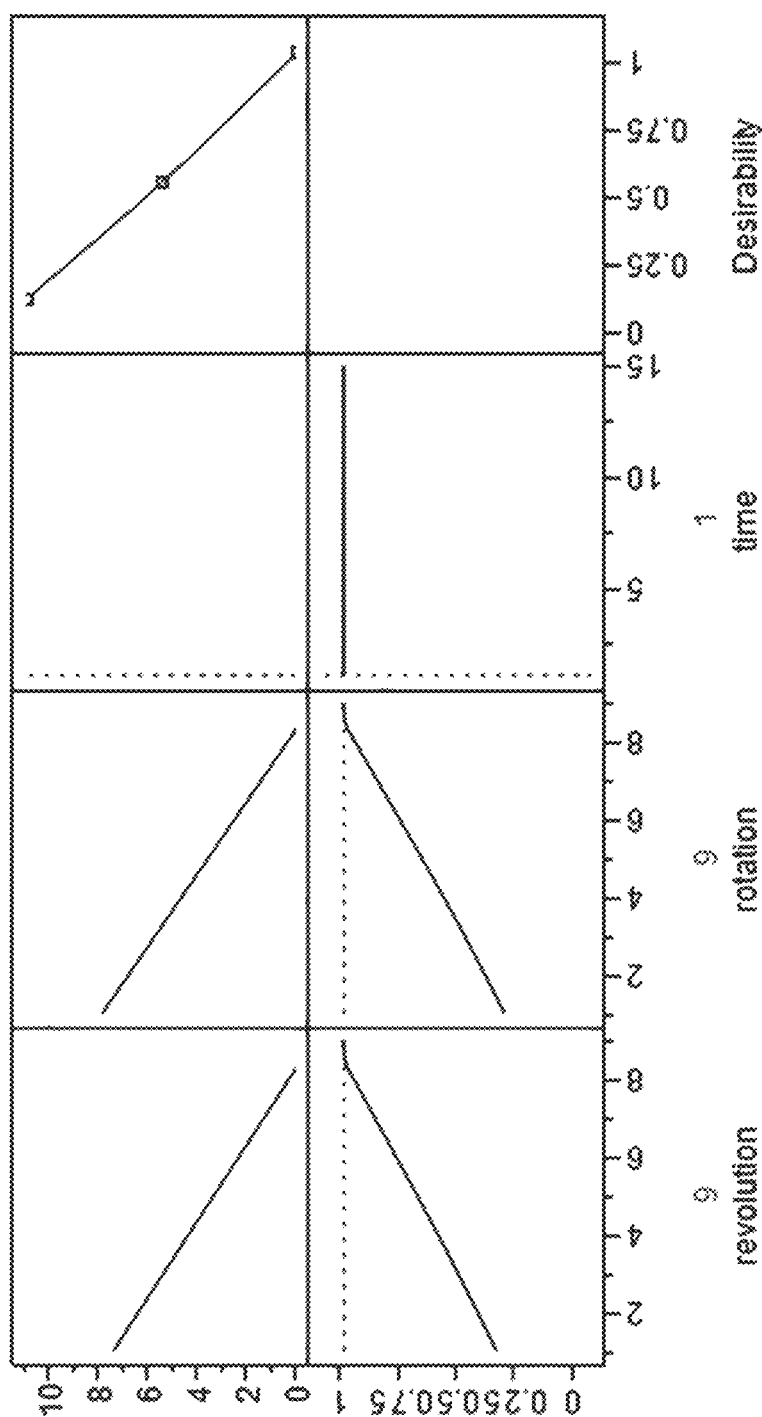
FIG. 30 represents non-limiting graphs showing implementation of a desirability algorithm for optimization of dispersing (mixing) of the progesterone composition of FIG. 28 and FIG. 29, where the desirability is set such that SD of percentage progesterone is zero and time setting is minimized to the lowest value (i.e., 10 seconds), in accordance with an implementation of the present invention.

Based on the cubic regression model (equation 1), a desirability algorithm was derived for optimization of the dispersing process. For optimal conditions, desirability was set such that SD of percent progesterone was zero and the time setting was minimized to the lowest value (i.e., 10 seconds). It was found that ideal conditions could be met given the following mixer settings: revolution=9, rotation=9 and time=1. This optimization is shown in FIG. 30.

Example 2

In this example, the superimposed revolution and rotation movements were performed in a planetary mixer (Mazerustar kk-300ss) in presence of grinding media. The following assays surprisingly demonstrated that the herein described superimposed revolution and rotation movements can be used to grind particles in presence of grinding media to obtain a desirable particle size distribution, while maintaining the temperature of the materials being grinded at a safe level below typical degradation temperature of thermally labile API.

Briefly, the container was filled with grinding media and sodium chloride for a total volume of 32 ml, and the superimposed revolution and rotation movements were performed at 1000 rpm (revolution) and 400 rpm (rotation) for 60 seconds with either sphere grinding media of 8 mm (58 beads) or cylinder grinding media of 10 mm (37 beads). A control grinding experiment was performed using mortar and pestle of sodium chloride.

Figure 31:
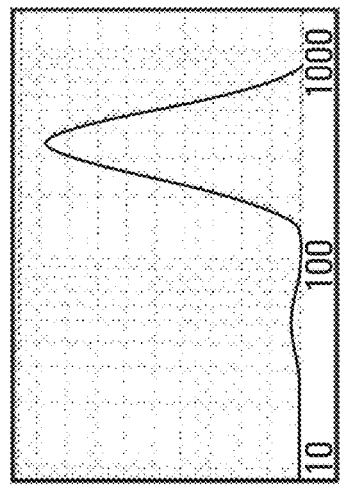
FIG. 31 represents non-limiting graphs showing initial particle size distribution (PSD) of sodium chloride (A) and the PSD after being processed according to prior art mortar and pestle dispersing (mixing) process (B), when processed using superimposed revolution and rotation movements in presence of grinding media spheres of 8 mm (C) or cylinders (D), in accordance with an implementation of the present invention.
Figure 31:
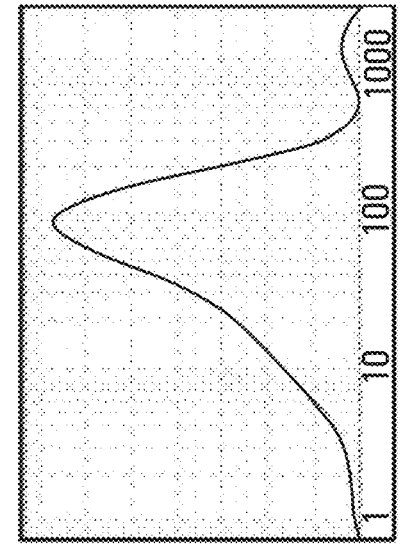
Figure 31:
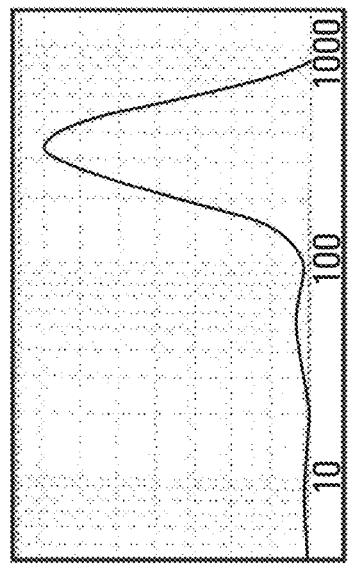
Figure 31:
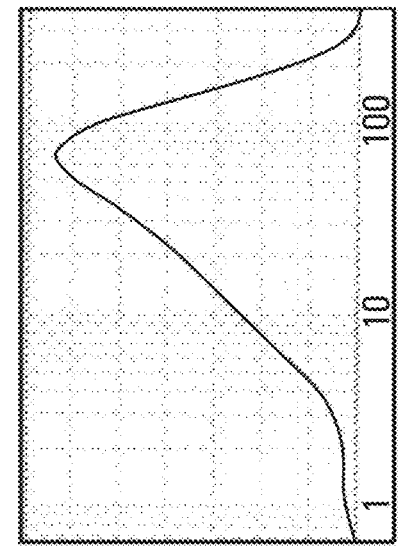

A first assay was performed with 20 g of sodium chloride (NDC 0629-08; lot number 602576/B, melting temperature of 801° C.). FIG. 31A shows that the sodium chloride prior to processing had the following particle size distribution (PSD) in µm: $D_{10}$ of 225.563, $D_{50}$ of 354.819 and $D_{90}$ of 539.090. FIG. 31B shows that the control experiment of mortar and pestle for 60 seconds demonstrated virtually no change in the PSD, with the following values in µm: $D_{10}$ of 171.989, $D_{50}$ of 328.938 and $D_{90}$ of 548.544. FIG. 31C shows that in contrast, grinding with spheres of 8 mm significantly shifted the PSD to the following lower values in µm: $D_{10}$ of 8.476, $D_{50}$ of 43.919 and $D_{90}$ of 126.183, while maintaining the temperature of the mixture at a safe level below typical degradation temperature of thermally labile API. Similarly, FIG. 31D shows that grinding with cylinders also significantly shifted the PSD to the following lower values in µm: $D_{10}$ of 11.835, $D_{50}$ of 64.803 and $D_{90}$ of 181.616, while maintaining the temperature of the mixture at a safe level below typical degradation temperature of thermally labile API. The results are also reported in the following Table 4:

TABLE 4

| | Grinding of sodium chloride | | | |
|---|---|---|---|---|
| | Control | Mortar and Pestle | Grinding Media (spheres) | Grinding Media (cylinders) |
| Surface Weighted Mean (µm) | 297.087 | 194.680 | 18.511 | 25.690 |
| Volume Weighted Mean (µm) | 367.953 | 343.262 | 57.384 | 99.796 |
| $D_{10}$ (µm) | 225.563 | 171.989 | 8.476 | 11.835 |
| $D_{50}$ (µm) | 354.819 | 328.938 | 43.919 | 64.803 |
| $D_{90}$ (µm) | 539.090 | 548.544 | 126.183 | 181.616 |
| Temp. before/after (° C.) | 24.7/NA | 24.5/24.1 | 24.7/39.8 | 25.9/36.9 |
| Weight before/after (g) | 5.016/NA | 20.012/19.989 | 20.027/19.887 | 20.025/19.908 |

Similar results were obtained when milling 30 g of sodium chloride using a mix of bead sizes, namely 80 beads were 8 mm and 25 beads were 6 mm, for a total weight of 310 g. Qualitative assessment of grinding efficacy was also performed in the planetary mixer using as starting material, granular sodium chloride at 10 g, 20 g or 30 g with 45 beads (spherical) of 8 mm filling the bottom layer of the container, for 60 sec at 1000 rpm. The results are that the various weights of materials were effectively grinded with these parameters.

Figure 32:
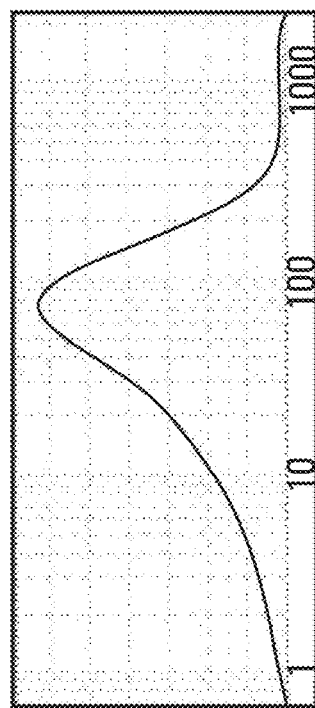
FIG. 32 represents non-limiting graphs showing initial particle size distribution (PSD) of Gabapentin (A) and the PSD after being processed according to prior art mortar and pestle dispersing (mixing) process (B), when processed using superimposed revolution and rotation movements in presence of grinding media spheres of 8 mm (C) or cylinders (D), in accordance with an implementation of the present invention.
Figure 32:
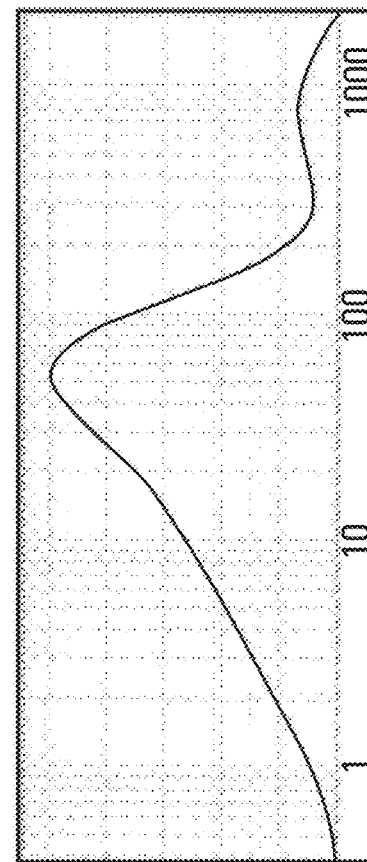
Figure 32:
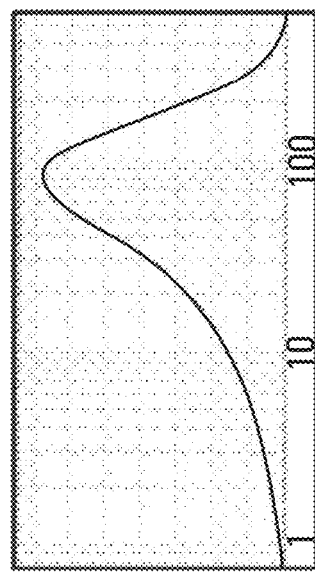
Figure 32:
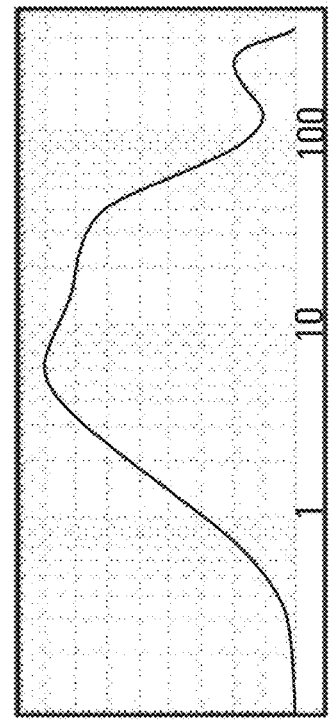

A second assay was performed with Gabapentin (NDC 2461-05; lot number 607832/B; melting temperature of 162° C.). FIG. 32A shows that the API prior to milling had the following particle size distribution (PSD) in μm: $D_{10}$ of 9.688, $D_{50}$ of 59.399 and $D_{90}$ of 164.334. FIG. 32B shows that the control experiment of mortar and pestle for 60 seconds demonstrated virtually no change in the PSD, with the following values in μm: $D_{10}$ of 8.033, $D_{50}$ of 53.500 and $D_{90}$ of 163.239. FIG. 32C shows that in contrast, grinding with spheres for 60 seconds at 1000 rpm (revolution) and 400 rpm (rotation) significantly shifted the PSD to the following lower values in μm: $D_{10}$ of 1.524, $D_{50}$ of 9.170 and $D_{90}$ of 58.913, while maintaining the temperature of the mixture at a safe level below the degradation temperature of the API. Similarly, FIG. 32D shows that grinding with cylinders for 60 seconds at 1000 rpm also significantly shifted the PSD to the following lower values in μm: $D_{10}$ of 3.878, $D_{50}$ of 33.616 and $D_{90}$ of 150.820, while maintaining the temperature of the mixture at a safe level below the degradation temperature of the API.

The results are also reported in the following Table 4A:

TABLE 4A

Grinding of Gabapentin

|  | Control | Mortar and Pestle | Grinding Media (spheres) | Grinding Media (cylinders) |
| --- | --- | --- | --- | --- |
| Surface Weighted Mean (μm) | 21.005 | 18.094 | 3.826 | 10.126 |
| Volume Weighted Mean (μm) | 76.316 | 81.389 | 25.998 | 91.378 |
| $D_{10}$ (μm) | 9.688 | 8.033 | 1.524 | 3.878 |
| $D_{50}$ (μm) | 59.399 | 53.500 | 9.170 | 33.616 |
| $D_{90}$ (μm) | 164.334 | 163.239 | 58.913 | 150.820 |
| Temp. Before/After (° C.) | 24.2/NA | 23.8/25.1 | 24.1/37.4 | 24.6/29.8 |
| Weight Before/After (g) | 2.508/NA | 10.003/9.797 | 10.011/9.292 | 10.019/9.599 |

Similar results were obtained when milling 15 g of Gabapentin using a mix of bead sizes, namely 80 beads were 8 mm and 42 beads were 6 mm, for a total weight of 310 g.

Other experiments were also made with the following starting material and grinding media using higher settings, namely a revolution speed of 2000 rpm and a rotation speed of 800 rpm:

TABLE 4B

Grinding of various API

| starting material and melting temp. (° C.) | grinding media | Temperature Before/After (° C.) | Observation |
| --- | --- | --- | --- |
| Menthol, 5 g (31) | 20 balls, 5 mm, spherical | 24.3/31.5 (30 sec) 24.3/32.5 (60 sec) | begins to clump (30 sec) melting (60 sec) |
| Sodium Chloride, 5 g (801) | 20 balls, 5 mm, spherical | 24.5/32.9 (30 sec) 24.5/48.3 (60 sec) | No visible reduction in particle size. |
| Sodium Chloride, 5 g (801) | 20 balls, 5 mm, cylindrical | 24.5/45.1 (30 sec) 24.5/58.5 (60 sec) | No visible reduction in particle size. |
| Gabapentin, 3 g (162) | 20 balls, 5 mm, cylindrical | 24.2/36.7 (30 sec) 24.2/46.8 (60 sec) | begins to clump (30 sec) very large clumps (60 sec) |
| Gabapentin, 2 g (162) | 25 balls, 10 mm, cylindrical | 24.2/39.1 (30 sec) | 1500 rpm/600 rpm; Container is hot to the touch. Powder has not clumped together. |

Other experiments were also made with 2 g of sodium chloride as starting material and grinding media using various settings to more easily visually detect particle size reduction:

TABLE 4C

Grinding of sodium chloride at various milling parameters

| grinding media | Temperature Before/After (° C.) | Observation |
|---|---|---|
| 45 balls, 8 mm, spherical | 23.4/28.7 (30 sec) 24.7/35.8 (60 sec) | 1000 rpm/400 rpm (rev./rot); Visual reduction in particle size without clumping. |
| 45 balls, 8 mm, spherical | 23.8/42.5 (30 sec) | 1500 rpm/600 rpm (rev./rot); Visual reduction in particle size without clumping. |
| 25 balls, 10 mm, cylindrical | 24.1/30.6 (30 sec) 24.2/39.5 (60 sec) | 1000 rpm/400 rpm (rev./rot); Visual reduction in particle size without clumping. |

Other experiments were also made with Gabapentin 2 g as starting material and grinding media using lower settings, namely a revolution speed of 1000 rpm and a rotation speed of 400 rpm:

TABLE 4D

Grinding of Gabapentin

| grinding media | Temperature Before/After (° C.) | Observation |
|---|---|---|
| 45 balls, 8 mm, spherical | 24.2/30.8 (30 sec) 25.7/35.7 (60 sec) | Visual reduction in particle size without clumping. |
| 25 balls, 10 mm, cylindrical | 24.4/25.6 (30 sec) 23.6/25.5 (60 sec) | Visually the powder does not look as micronized compared to tests with spheres. |

These last results suggest that processing time parameters of 30 and 60 seconds keep temperature below 40° C., which is below the typical degradation temperature for a thermally labile API.

Example 3

In this example, the following compounded pharmaceutical compositions were prepared using the herein described superimposed revolution and rotation movements using a planetary mixer (Mazerustar kk-300ss) with the following dispersion parameters: processing time of 30 sec or 60 sec (either continuously or in two intervals of 30 seconds each), and dispersion speeds of 2000 rpm revolution and 800 rpm rotation. In some cases, a dye was added to the ingredients showing that the herein described superimposed revolution and rotation movements can be used to also disperse colorant within a compounded pharmaceutical composition.

TABLE 5

Ointment pharmaceutical composition
2% Mucirocin Ointment

| Ingredient (NDC, Lot) | Mupirocin (2545-03, 602996/B), Mineral Oil (0949-08, 38546/1), Medisca OleaBase Plasticized (2575-05, 601610/B) |
|---|---|

TABLE 5-continued

Ointment pharmaceutical composition
2% Mucirocin Ointment

| API Melting Temperature (° C.) | Mupirocin (77-78) |
|---|---|
| Specific Gravity of Base | OleaBase Plasticized (0.85) |

TABLE 6

Hormone replacement therapy (HRT) pharmaceutical composition (emulsion)
0.5% Estriol Vaginal Cream (Emulsion, 30 ml)

| Ingredient (NDC, Lot) | Estriol (0732-03, 51222/C), Propylene Glycol (0510-08, 45008/B), VersaPro Cream (2529-08, 124989/B) |
|---|---|
| API Melting Temperature (° C.) | Estriol (288) |
| Specific Gravity of Base | VersaPro Cream (0.97) |
| Temperature before/after (° C.) | 23.6/25.4 (30 sec.) 25.2/26.2 (30 sec., rest, 30 sec.) 25.8/28.0 (60 sec) |

TABLE 7

Hormone replacement therapy pharmaceutical composition (cream base)
Estradiol 0.5 mg/ml, Estriol 2 mg/ml, Progesterone 150 mg/ml Cream Base

| Ingredient (NDC, Lot) | Estradiol Estriol (0732-03, 51222/C), Progesterone (0043-08, 56345/B), Propylene Glycol (0510-08, 45008/B), HRT Cream (0701-08, 46213/K/B) |
|---|---|
| API Melting Temperature (° C.) | Estriol (288) Estradiol (178) Progesterone (129) |
| Specific Gravity of Base | VersaPro Cream (0.97) |
| Temperature before/after (° C.) | 23.5/29.4 (30 sec.) 29.1/29.7 (30 sec., rest, 30 sec.) 29.1/31.0 (60 sec.) |

TABLE 8

Hormone replacement therapy pharmaceutical composition (cream base)
Estradiol 0.5 mg/ml, Estriol 2 mg/ml,
Progesterone 150 mg/ml, HRT Cream Base

| Ingredient (NDC, Lot) | Estradiol Estriol (0732-03, 51222/C), Progesterone (0043-08, 56345/B), Propylene Glycol (0510-08, 45008/B), HRT Cream (0701-08, 46213/K/B) |
|---|---|
| API Melting Temperature (° C.) | Estriol (288) Estradiol (178) Progesterone (129) |
| Specific Gravity of Base | HRT Cream (0.98) |
| Viscosity of Base | HRT Cream (370 000 cP) |
| Temperature before/after (° C.) | 23.5/29.4 (30 sec.) 29.1/29.7 (30 sec., rest, 30 sec.) 29.1/31.0 (60 sec.) |

TABLE 9

Gel composition
Ibuprofen 5%, Menthol 3% Topical Gel (Suspension, 50 g)

| Ingredient (NDC, Lot) | Ibuprofen (0299-05, 57128/A), Menthol (0521-05, 41612/B), Propylene Glycol (0510-08, 45008/B), VersaPro Gel (2636-05, 45712/P) |
|---|---|
| API Melting Temperature (° C.) | Ibuprofen (76), Menthol (41-44) |

TABLE 9-continued

Gel composition
Ibuprofen 5%, Menthol 3% Topical Gel (Suspension, 50 g)

| | |
|---|---|
| Specific Gravity of Base | VersaPro Gel (1.00) |
| Viscosity of Base | VersaPro Gel (1,000,000 cP) |
| Temperature before/after (° C.) | 23.0/27.3 (30 sec.) |
| | 22.9/26.0 (30 sec., rest, 30 sec.) |
| | 23.1/29.3 (60 sec.) |

TABLE 10

Gel composition
Ibuprofen 5%, Menthol 3%, Medisca VersaPro Gel Base

| | |
|---|---|
| Ingredient (NDC, Lot) | Ibuprofen (0299-05, 57128/A), Menthol (0521-05, 41612/B), Propylene Glycol (0510-08, 45008/B), VersaPro Gel (2636-05, 45712/P) |
| API Melting Temperature (° C.) | Ibuprofen (76), Menthol (41-44) |
| Specific Gravity of Base | VersaPro Gel (0.984) |
| Viscosity of Base | VersaPro Gel (1,000,000 cP) |
| Temperature before/after (° C.) | 23.2/24.8 (30 sec.) |
| | 24.8/25.7 (30 sec., rest, 30 sec.) |
| | 25.6/28.4 (60 sec.) |

TABLE 11

Pain pharmaceutical composition
Gabapentin 6%, Ketoprofen 5%, Diclofenac 3%, Pentylene Glycol 3%, Ethoxy Diglycol 3%, Medisca VersaPro Cream Base.

| | |
|---|---|
| Ingredient (NDC, Lot) | Gabapentin (2461-05, 57807/1), Ketoprofen (0078-05, 56561 /B), Diclofenac (2552-08, 44843/B), Pentylene Glycol (2752-08, 50713/A), Ethoxy Diglycol (1903-05, 54500/B), VersaPro Cream (2529-08, 124989/B) Red dye |
| API Melting Temperature (° C.) | Gabapentin (162-166) Ketoprofen (94) Diclofenac (283-285) |
| Specific Gravity of Base | VersaPro Cream (0.99) |
| Temperature before/after (° C.) | 23.3/24.9 (30 sec.) |
| | 24.7/25.5 (30 sec., rest, 30 sec.) |
| | 25.4/26.6 (60 sec.) |

In the particular pain pharmaceutical composition described in Table 11, the red dye was added on top of the ingredients. Following the dispersion of the ingredients, the resulting mixture had a substantially homogeneous pink color as early as 30 sec.

TABLE 12

Amlodipine Suspension
Amlodipine 1 mg/mL, Medisca Oral Mix

| | |
|---|---|
| Ingredient (NDC, Lot) | Amlodipine (2734-blk, 49214, 04/2018), Medisca Oral Mix (2512-08,1102/A, 09/2015) Red dye |
| API Melting Temperature (° C.) | Amlodipine (178-179) |
| Specific Gravity of Base | Oral Mix (1.1202) |
| Viscosity of Base | Oral Mix (300 cP) |
| Temperature before/after (° C.) | 15.8/16.0 (30 sec.) |
| | 16.0/16.2 (30 sec., rest, 30 sec.) |
| | 16.2/17.0 (60 sec.) |

In this particular example of a pharmaceutical suspension being dispersed in presence of a red dye, the dye was placed on top of the ingredients. Following the dispersion of the ingredients, the resulting mixture had a substantially homogeneous pink color as early as 30 sec.

Example 4

In this example, the following compounded pharmaceutical compositions were prepared using the herein described superimposed revolution and rotation movements in a planetary mixer (Mazerustar kk-300ss). The dispersing time and the dispersing speed parameters were modified, and a dispersing assessment was made, as indicated in the following tables. Note that the rotation speed (rpm) was kept at a value of 40% of the revolution speed (rpm).

TABLE 13

Cellulose, NF (Microcrystalline)

| | | |
|---|---|---|
| Ingredient (NDC, Lot) | Cellulose, NF (0567-08, 27688/B) | |
| Weight (g) | 50 | 25 |
| Temperature before/ after (° C.) when room temperature at 24° C. | 29.3 (1000 rpm/120 sec) 35.3 (1500 rpm/120 sec) 31.4 (1500 rpm/60 sec) | 33.0 (1500 rpm/60 sec) 30.4 (1500 rpm/30 sec) |
| Mixing assessment | 1000 rpm/120 sec    + 1500 rpm/120 sec    + | 1500 rpm/60 sec   ++ 1500 rpm/30 sec   ++ |

TABLE 14

Lactose, NF (Monohydrate) at variable dispersing time

| Ingredient (NDC, Lot) | | Lactose, NF (Monohydrate) (0315-08, 600938/Cand 603118/B) | |
|---|---|---|---|
| Weight (g) | | 50 | |
| Revolution (rpm) | Dispersing time (sec) | Temperature after (° C.) when room temperatureat 24° C. | Mixing assessment |
| 1000 | 150 | 29.7 | ++ |
| 1000 | 120 | 29.4 | ++ |
| 1000 | 90 | 28.0 | ++ |
| 1000 | 60 | 28.0 | ++ |
| 500 | 30 | 25.2 | + |
| 1000 | 30 | 26.7 | ++ |
| 1500 | 30 | 30.9 | ++ |
| 2000 | 30 | 40.5 | ++ |

TABLE 15

Lactose, NF (Monohydrate) at 180 sec dispersing time

| Ingredient (NDC, Lot) | | Lactose, NF (Monohydrate) (0315-08, 600938/C and 603118/B) Red dye | |
|---|---|---|---|
| Dispersing time (sec) | | 180 | |
| Weight (g) | Revolution (rpm) | Temperature after (° C.) when room temperature at 24° C. | Mixing assessment |
| 25 | 500 | 24.6 | ++ |
| | 1000 | 29.6 | ++ |
| | 1500 | 38.1 | ++ |
| | 2000 | 51.5 | |
| 50 | 500 | 26.7 | ++ |
| | 1000 | 32.1 | ++ |
| | 1500 | 43.8 | ++ |
| | 2000 | 63.2 | |

TABLE 15-continued

| Lactose, NF (Monohydrate) at 180 sec dispersing time | | | |
|---|---|---|---|
| 60 | 500 | * | ++ |
|  | 1000 | 31.1 |  |
|  | 1500 | 44.0 |  |
|  | 2000 | ** |  |
| 75 | 500 | * | ++ |
|  | 1000 | 27.9 | ++ |
|  | 1500 | 37.2 | ++ |
|  | 2000 | 55.5 |  |

In the above results, * means that the G forces were observed as being insufficient to achieve a mix whereas ** means that the temperature exceeded the pre-determined threshold temperature of 45° C. for thermally labile API. In this example, a red dye was used to qualitatively assess the dispersion.

TABLE 16

| Capsublend at 60 sec dispersing time | |
|---|---|
| Ingredient (NDC, Lot) | Capsublend-P (2594-08, 58203/C) Capsublend-S (2593-05, 51997/B and 38893/B) Red dye |
| Dispersing time (sec) | 60 |

| Weight (g) | Revolution (rpm) | Rotation (rpm) | Temperature after (° C.) when room temperature at 24° C. | Mixing assessment |
|---|---|---|---|---|
| 25 | 400 | 160 | 25.0 | — |
|  | 1000 | 400 | 27.5 | — |
|  | 1500 | 600 | 31.1 | — |
|  | 2000 | 800 | 37.5 | ++ |
| 50 | 400 | 160 | 25.1 | — |
|  | 1000 | 400 | 27.9 | — |
|  | 1500 | 600 | 32.4 | — |
|  | 2000 | 800 | 41.9 | ++ |

Example 5

In this example, the following compounded pharmaceutical compositions including 3 different APIs were prepared using the herein described superimposed revolution and rotation movements, or using an Unguator™ as control comparative blade mixing device (Gako International), with the following ingredients:

TABLE 17

| Ingredients | | | | |
|---|---|---|---|---|
|  | % | g/ml | NDC | Lot |
| Diclofenac Sodium | 3.0 | 7.5, 7.95, 7.8 | 2705-05 | 44843/B |
| Gabapentin | 6.0 | 15, 15.9, 15.6 |  | 603948/A |
| Ketoprofen | 5.0 | 12.5, 13.25, 13 |  | 602182/F |
| Pentylene Glycol | 3.0 | 7.5, 6.5, 6.25 | 2752-08 | 507131/A |
| Ethoxy Diglycol | 3.0 | 7.5, 6.5, 6.25 |  | 54500/B |
| VersaPro Cream Base | QS to 250 g | 188.5, 265, 260 |  | 605062/A |

The superimposed revolution and rotation movements parameters were: 2000 rpm for 30 sec (samples 1-3). The parameters for the Unguator™ control comparative blade mixing device (samples 4-5) were: speed 5 for 120 sec (sandwich protocol). Each of the resulting composition was then separated in top, middle and bottom layers and the concentration of each API in each layer was measured with HPLC. The average concentration ([ ]), the standard deviation (SD) and the relative standard deviation (% RSD) were calculated for each API. The results are shown in the following Table:

TABLE 17A

| Results for a composition including 3 API | | | | | | | | | |
|---|---|---|---|---|---|---|---|---|---|
|  | Diclofenac 3% | | | Gabapentin 6% | | | Ketoprofen 5% | | |
| Assay | [ ] | SD | % RSD | [ ] | SD | % RSD | [ ] | SD | % RSD |
| 1 | 2.8 | 0.000 | 0.0% | 5.9 | 0.047 | 0.8% | 4.9 | 0.125 | 2.5% |
| 2 | 2.8 | 0.047 | 1.7% | 5.8 | 0.000 | 0.0% | 4.9 | 0.082 | 1.7% |
| 3 | 2.7 | 0.000 | 0.0% | 5.7 | 0.000 | 0.0% | 4.8 | 0.047 | 1.0% |
| 4 | 2.8 | 0.125 | 4.4% | 5.6 | 0.262 | 4.7% | 4.9 | 0.283 | 5.8% |
| 5 | 2.7 | 0.094 | 3.5% | 5.4 | 0.262 | 4.8% | 4.7 | 0.216 | 4.6% |
| 6 | 2.8 | 0.082 | 2.9% | 5.5 | 0.170 | 3.1% | 4.8 | 0.094 | 2.0% |

These results show that the average % RSD is significantly lower when using the superimposed revolution and rotation movements relative to the Unguator™ control comparative blade mixing device. The inventors were also able to consistently (in over 80% of the cases) obtain for a given API less than 3% RSD, suggesting a significant homogeneity in the compositions made as well as more reproducible results (i.e., less variations from one composition to another). In contrast, the Unguator™ control comparative blade mixing device consistently (in over 80% of the cases) showed higher and variable % RSD for a given API, suggesting less homogeneous compositions and less reproducible results.

Example 6

In this example, the following compounded pharmaceutical compositions including 4 different APIs were prepared using the herein described superimposed revolution and rotation movements, with the following ingredients:

TABLE 18

| Ingredients | | | | |
|---|---|---|---|---|
| Ingredients | % | g/ml | NDC | Lot |
| Baclofen, USP | 2.0 | 4.0 | 0388-04 | 112624/E |
| Bupivacaine HCl, USP | 2.5 | 5.0 | 0524-04 | 122720/I |
| Cyclobenzaprine HCl, USP | 6.0 | 12.0 | 0395-05 | 115114/E |
| Diclofenac Sodium, USP | 10.0 | 20.0 | 2705-05 | 118032/I |
| Ethoxy Diglycol | 3.5 | 7.0 | 1903-05 | 119825/D |
| Pentylene Glycol | 3.5 | 7.0 | 2752-08 | 122018/B |
| VersaPro Cream Base | 72.5 | 145.0 | 2529-08 | 121176/D |

The superimposed revolution and rotation movements parameters were: 2000 rpm for 30 sec (samples 4-6). The parameters for the Unguator™ control comparative blade mixing device (samples 1-3) were: speed 5 for 120 sec (sandwich protocol). Each of the resulting composition was then separated in top, middle and bottom layers and the concentration of each API in each layer was measured with HPLC. The average concentration ([ ]), the standard deviation (SD) and the relative standard deviation (% RSD) were calculated for each API. The results are shown in the following Table:

TABLE 19

Results for a composition including 4 API

| | Baclofen, 2% | | | Bupivicaine, 2.5% | | | Cyclobenzaprine, 6% | | | Diclofenac, 10% | | |
|---|---|---|---|---|---|---|---|---|---|---|---|---|
| Assay | [ ] | SD | % RSD | [ ] | SD | % RSD | [ ] | SD | % RSD | [ ] | SD | % RSD |
| 1 | 2.0 | 0.265 | 13% | 2.1 | 0.265 | 13% | 5.4 | 0.586 | 11% | 9.5 | 1.079 | 11% |
| 2 | 2.0 | 0.058 | 3% | 2.1 | 0.100 | 5% | 5.3 | 0.208 | 4% | 9.3 | 0.361 | 4% |
| 3 | 1.9 | 0.306 | 16% | 2.0 | 0.306 | 15% | 5.1 | 0.794 | 16% | 9.1 | 1.401 | 15% |
| 4 | 2.1 | 0.058 | 3% | 2.2 | 0.058 | 3% | 5.6 | 0.208 | 4% | 9.9 | 0.321 | 3% |
| 5 | 2.1 | 0.100 | 5% | 2.2 | 0.115 | 5% | 5.5 | 0.306 | 6% | 9.6 | 0.586 | 6% |
| 6 | 1.9 | 0.000 | 0% | 2.1 | 0.000 | 0% | 5.2 | 0.153 | 3% | 9.1 | 0.153 | 2% |

These results show that the average % RSD is significantly lower when using the superimposed revolution and rotation movements relative to the Unguator™ control comparative blade mixing device. The inventors were also able to consistently (in over 80% of the cases) obtain for a given API less than 3% RSD, suggesting a significant homogeneity in the compositions made as well as more reproducible results (i.e., less variations from one composition to another). In contrast, the Unguator™ control comparative blade mixing device consistently (in over 80% of the cases) showed higher and variable % RSD for a given API, suggesting less homogeneous compositions and less reproducible results.

Example 7

In this example, a jar container having a certain internal ratio was used to disperse ingredients using the herein described superimposed revolution and rotation movements. The jar is equipped with an adaptor to fit the jar container into a receiving basket of a planetary mixer. The ingredients used a pharmaceutically acceptable carrier, excipient or diluent, Versapro Cream Base and a red dye, as a tracer. The amount of Versapro added into the container was sufficient to reach the top of the viewing window on the jar container (MD line of containers, from Medisca Pharmaceutique). Note that the rotation speed (rpm) was kept at a value of 40% of the revolution speed (rpm).

TABLE 20

Results for Versapro Cream in MD jar container

| Volume of Versapro Cream Base | Revolution (rpm) | Temperature (° C.), Time | Observation |
|---|---|---|---|
| 30 ml | 400 | 23.3 (30 sec) | Dye reached halfway down (30 sec) |
| | | 23.7 (60 sec) | Dye moved 5 mm further (60 sec) |
| | | 24.0 (90 sec) | Dye moved 2 mm further (90 sec) |
| | | 24.3 (120 sec) | Dye 2 mm from bottom. (120 sec) |
| | 1000 | 24.7 (30 sec) | Dye reached the bottom, homogeneous mix |
| | | 25.2 (120 sec) | (30 and 120 sec) |
| | 1500 | 25.9 (120 sec) | Dye reached the bottom, homogeneous mix |
| | 2000 | 24.0 (30 sec) | Dye reached the bottom, homogeneous mix |
| | | 26.5 (120 sec) | (30 and 120 sec) |
| 50 ml | 400 | 23.7 (120 sec) | |
| | 1000 | 24.0 (30 sec) | Dye reached the bottom, homogeneous mix |
| | | 25.7 (120 sec) | (30 and 120 sec) |
| | 1500 | 23.9 (30 sec) | Dye reached the bottom, homogeneous mix |
| | | 25.7 (120 sec) | (30 and 120 sec) |
| | 2000 | | Slight leakage past the piston at all tested times, except for 120 sec where it is severe leakage |
| 80 ml | 400 | 23.6 (120 sec) | Dye reached the bottom, homogeneous mix |
| | 1000 | 23.8 (30 sec) | Dye reached the bottom, homogeneous mix |
| | | 24.6 (120 sec) | |
| | 1500 | 23.9 (30 sec) | Dye reached the bottom, homogeneous mix |
| | | 25.8 (120 sec) | |
| | 2000 | 27.2 (120 sec) | Dye reached the bottom, homogeneous mix |

Safe dispersing parameters so as to avoid leakage, thus, appear to be 1500 rpm at 0.5 min, and are applicable to all sizes of the MD line of jar containers.

Example 8

In this example, a 6.5 ml syringe container (Medisca Pharmaceutique) was used to disperse ingredients using the herein described superimposed revolution and rotation movements. The syringe container is equipped with an adaptor to fit the syringe container into a receiving basket of the planetary mixer. The ingredients used were a pharmaceutically acceptable carrier, excipient or diluent, Versapro Cream Base and a red dye, as a tracer. The amount of Versapro added into the syringe container was of 6.5 g. The dispersed cream was then visually assessed for entrapped air bubbles levels and red dye homogeneity dispersion. Note that the rotation speed (rpm) was kept at a value of 40% of the revolution speed (rpm).

TABLE 21

Results for Versapro Cream in syringe container

| Revolution (rpm) | Time (sec) | Observation |
|---|---|---|
| 500 | 120 | Dye failed to travel down. No noticeable change in air bubble size or shape. |
| 1000 | 120 | Dye failed to travel down. Air bubbles size has decreased but still large number of bubbles visible (mostly non-uniform in size and shape). |
| 1500 | 30 | Dye moved down 2 cm. Air bubbles size has decreased and shape of air bubbles is more uniform. |
|  | 60 | Dye moved down a further 0.5 cm. Layers of colour near the center suggesting heterogeneous mixing. |
|  | 90 | Dye moved down a further 0.5 cm. Layers of colour near the center suggesting heterogeneous mixing. |
|  | 120 | Dye stopped at center cartridge. Heterogeneous mix |
| 2000 | 30 | Dye moved down effectively (2.7 cm). Fewer air bubbles, size has also decreased. Less bubble towards the top. |
|  | 60 | Dye moved down an additional 1-1.5 cm. Mixing flow visible. Layers of distinct shades of pink indicate non-uniform mixing near the center. Slightly more uniform bubble size and shape. No significant change in number of bubbles. Temperature: 28.5° C. |
|  | 90 | Dye moved down (1 cm above the bottom of the cartridge). Mixing flow visible. Top layer (darker pink) has increased, more uniform in the middle compared to before, however, layers still visible. No significant Change in size, shape or number of bubbles. Temperature: 29.7 C. ° |
|  | 120 | Dye has reached bottom of cartridge completely. Mixing flow visible. Layers are less prevalent, color is more uniform throughout. Noticeable change in number of bubbles. Size has slightly decreased. Temp: 31.2 C. ° |

Similar results were obtained when dispersing in a syringe container of 5.0 ml (Medisca Pharmaceutique, Montreal, Canada).

Example 9

In this example, various pharmaceutically acceptable excipients, carriers or diluents in solid or semi-solid form (i.e., more or less viscous, so long as it cannot be poured like a liquid) were submitted to the herein described superimposed revolution and rotation movements in an attempt to obtain a reversible melt. The dispersing parameters used were 2000 rpm revolution and 800 rpm rotation.

TABLE 22

Melting of excipient, carrier or diluent

| Excipient, carrier or diluent | Observation |
|---|---|
| VersaPro ™ Cream | 300 sec dispersing resulted in a temperature of 31.6° C., appears as a cream |
| OleaBase ™ Plastisized Ointment Base | 240 sec dispersing resulted in a temperature of 38.2° C. 300 sec dispersing resulted in a temperature of 34.2° C., the base became very soft and liquid. There is a major change in consistency and texture. |
| PLO Gel Mediflo ™ 30 | 210 sec dispersing resulted in a temperature of 39.1° C., the gel appears like a cream, not a pourable liquid |
| PolyPeg Suppository Base | 300 sec dispersing resulted in a temperature of 51.1° C., the base appears like a cream, not a pourable liquid |
| SPG Supposi-Base ™ | 300 sec dispersing resulted in a temperature of 34.1° C., the base appears like a cream, not a pourable liquid |
| Gum Base Gelatin | 180 sec dispersing resulted in a temperature of 55.1° C., the initial cube shaped gelatin forms melt into a pourable liquid. |

The experiment was repeated in different planetary mixer devices, as per the following paragraphs.

TABLE 22.1

Mazerustar KK-300SS comparison of gelatin gum base chunk size

|  | Test 10 | Test 16 |
|---|---|---|
| Lot Number | 617221/A | 617221/A |
| Mass (gram) | 50.02 | 50.07 |
| RPM | 2000 | 2000 |
| G Force | 284 | 284 |

TABLE 22.1-continued

| Mazerustar KK-300SS comparison of gelatin gum base chunk size | | |
|---|---|---|
| | Test 10 | Test 16 |
| Time (seconds) | 180 | 180 |
| Temperature Before (° C.) | 23.8 | 25.5 |
| Temperature After (° C.) | 59.6 | 57.7 |
| ΔT (° C.) | 35.8 | 32.2 |
| Observation | fully melted | not fully melted as little blocks cut stuck to the top |

Figure 33:
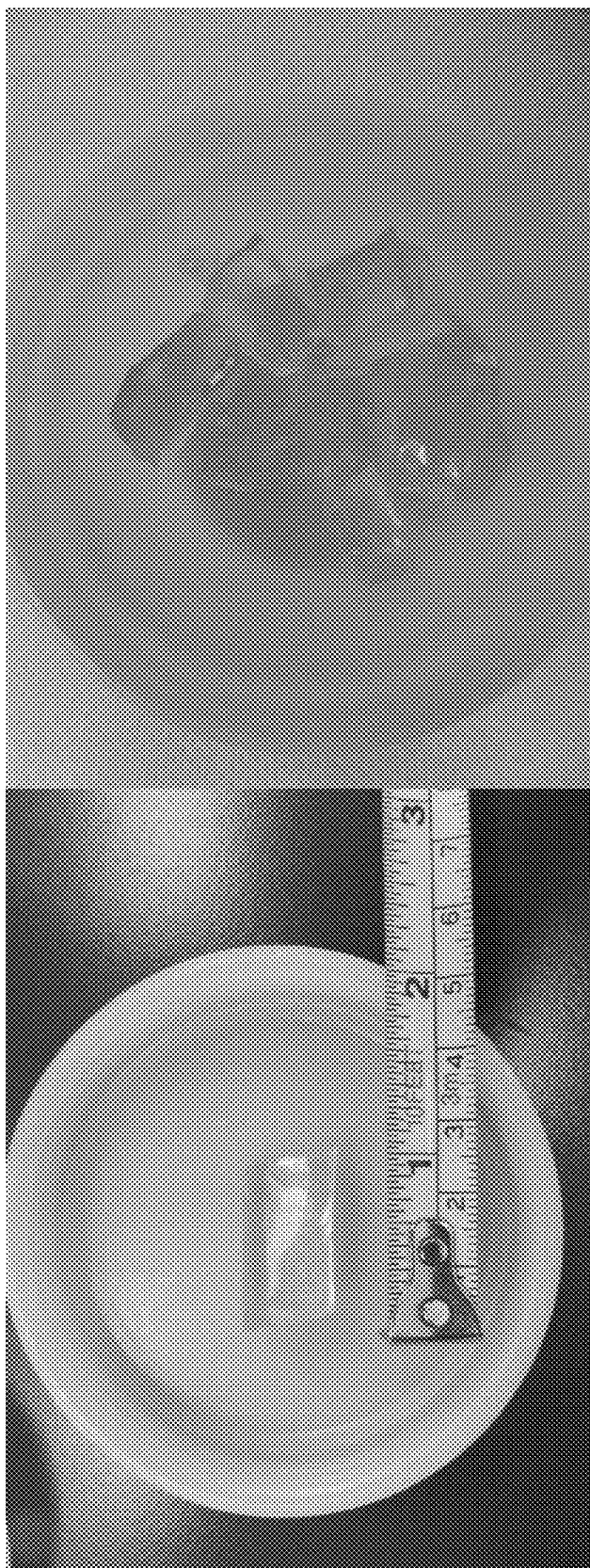
FIG. 33 shows a typical gum base gelatin particle unaltered from the manufacturers' container (left) and a plurality of these particles contained in the dispersion container (right). The block has a maximal extent size of about 1 inch, in accordance with an implementation of the present invention.

FIG. 33 shows a typical gum base gelatin particle unaltered from the manufacturers' container (left) and a plurality of these particles contained in the dispersion jar (right). The block has a maximal extent size of about 1 inch.

Figure 34:
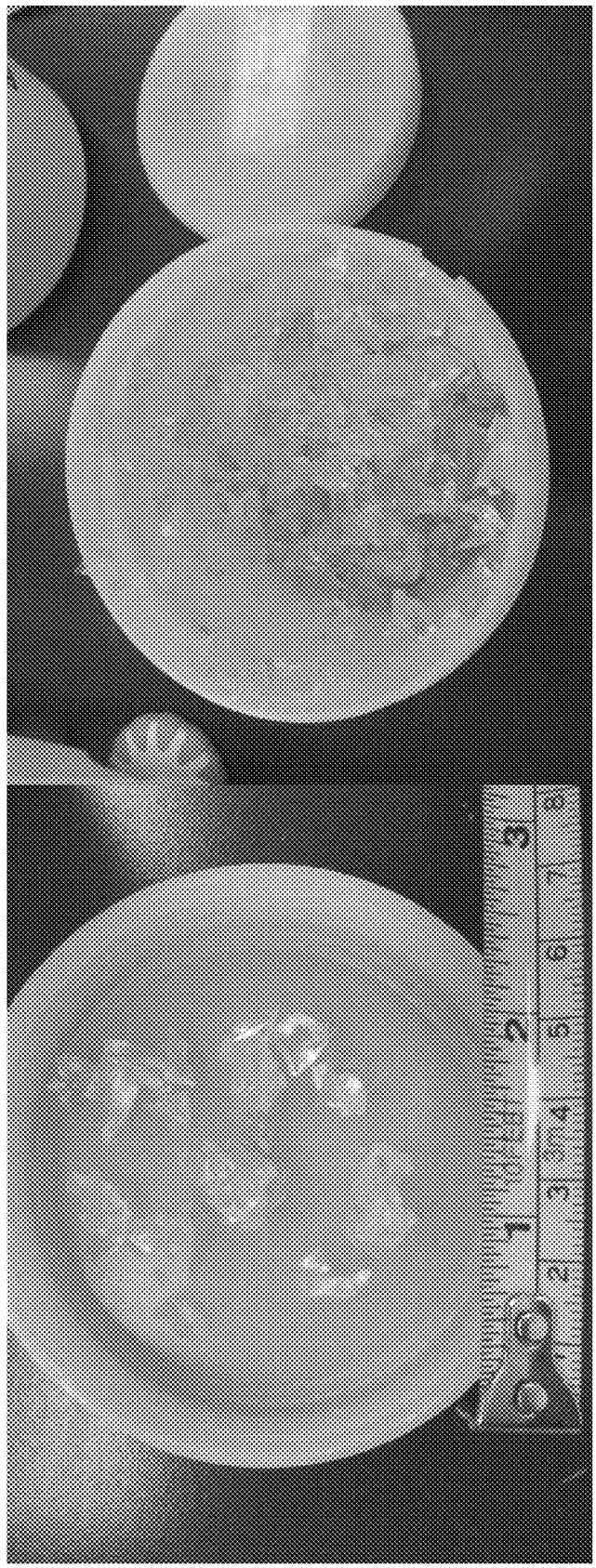
FIG. 34 shows gum base gelatin particles which have been cut down from the initial size present in the manufacturers' container (left) and a plurality of these particles contained in the dispersion container (right). The cut down particles have a size of less than about 0.5 inch, in accordance with an implementation of the present invention.
Figure 35A:
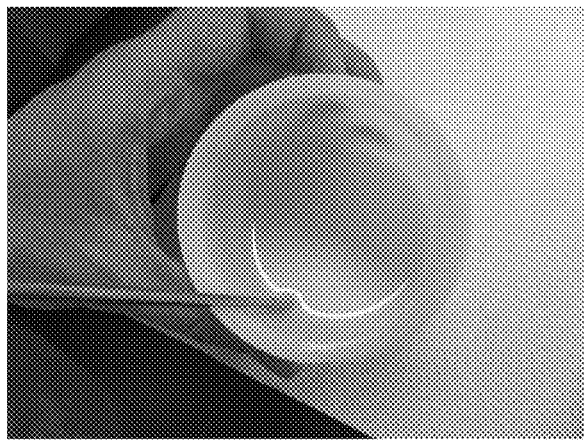
FIG. 35A-35E shows examples of gum base in the dispersion container that completely melted (35A), partially melted (35B, 35C and 35D), and did not melt (35E), in accordance with an implementation of the present invention.
Figure 35B:
Figure 35C:
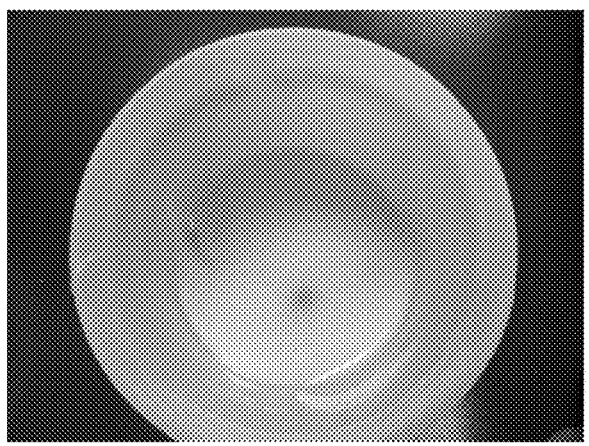
Figure 35D:
Figure 35E:
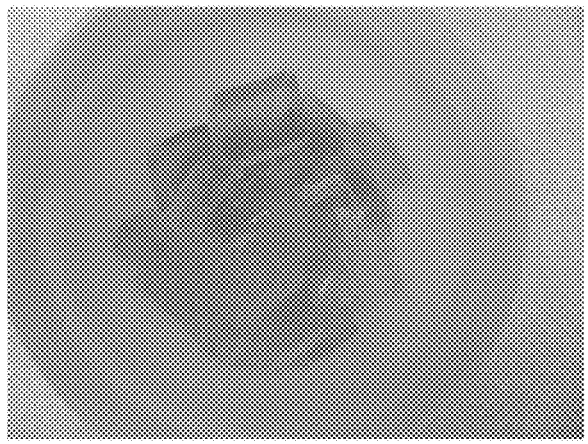

FIG. 34 shows gum base gelatin particles which have been cut down from the initial size present in the manufacturers' container (left) and a plurality of these particles contained in the dispersion jar (right). The cut down particles have a size of less than about 0.5 inch.

A two (2) decimal place balance was used to weigh the gelatin gum base. During the weighing operations, a plastic jar was placed on the balance and tared. During the first experiment run, 50 grams was processed unaltered. During the second experiment run, the 50 grams of gelatin gum base was minced into smaller pieces. The initial temperature was recorded using a digital thermometer with stainless steel probe by inserting the tip inside of the gum base gelatin before being inserted inside the planetary mixer. The final temperature was measured once the dispersion process was completed, by inserting and swirling the stainless steel probe in the gelatin in order to avoid coagulation as much as possible.

The herein described superimposed revolution and rotation movements was used to melt the gelatin gum base and the process parameters/results obtained were compared to those performed/obtained when using a hot plate. The melted gelatin gum base was assessed by measuring the temperature before and after the melting process by using a digital thermometer with a stainless-steel probe. FIG. 35A-35E shows examples of gum base that completely melted (35A), partially melted (35B, 35C and 35D), and did not melt (35E).

TABLE 22.2

| Mazerustar KK-300SS-25 gram, 180 seconds, variable G Force | | | |
|---|---|---|---|
| | Test 3 | Test 2 | Test 4 |
| Lot Number | 617221/A | 617221/A | 617221/A |
| Mass (gram) | 25.00 | 25.20 | 25.03 |
| RPM | 1600 | 1800 | 2000 |
| G Force | 182 | 230 | 284 |
| Time (seconds) | 180 | 180 | 180 |
| Temperature Before (° C.) | 24.3 | 24.3 | 24.3 |
| Temperature After (° C.) | 50.5 | 49.1 | 51.6 |
| ΔT (° C.) | 26.2 | 24.8 | 27.3 |
| Observation | partially melted | completely melted | completely melted |

TABLE 22.3

| Mazerustar KK-300SS-50 gram, 180 seconds, variable G Force | | | |
|---|---|---|---|
| | Test 7 | Test 9 | Test 10 |
| Lot Number | 617221/A | 617221/A | 617221/A |
| Mass (gram) | 50.04 | 50.01 | 50.02 |
| RPM | 1600 | 1800 | 2000 |
| G Force | 182 | 230 | 284 |
| Time (seconds) | 180 | 180 | 180 |
| Temperature Before (° C.) | 24.3 | 24.0 | 23.8 |
| Temperature After (° C.) | 50.7 | 56.1 | 59.6 |
| ΔT (° C.) | 26.4 | 32.1 | 35.8 |
| Observation | partially melted | completely melted | completely melted |

TABLE 22.4

| Mazerustar KK-300SS-75 gram, 180 seconds, variable G Force | | | |
|---|---|---|---|
| | Test 8 | Test 11 | Test 12 |
| Lot Number | 617221/A | 617221/A | 617221/A |
| Mass (gram) | 75.03 | 75.03 | 75.03 |
| RPM | 1600 | 1800 | 2000 |
| G Force | 182 | 230 | 284 |
| Time (seconds) | 180 | 180 | 180 |
| Temperature Before (° C.) | 23.6 | 23.4 | 23.3 |
| Temperature After (° C.) | 30.6 | 30.3 | 56.4 |
| ΔT (° C.) | 7.0 | 6.9 | 33.1 |
| Observation | not melted | not melted | completely melted |

TABLE 22.5

| Mazerustar KK-300SS-75 gram, constant G Force, variable time | | | |
|---|---|---|---|
| | Test 12 | Test 18 | Test 17 |
| Lot Number | 617221/A | 617221/A | 617221/A |
| Mass (gram) | 75.03 | 75.01 | 75.00 |
| RPM | 2000 | 2000 | 2000 |
| G Force | 284 | 284 | 284 |
| Time (seconds) | 180 | 300 | 450 |
| Temperature Before (° C.) | 23.3 | 25 | 23.7 |
| Temperature After (° C.) | 56.4 | 60.9 | 61.9 |
| ΔT (° C.) | 33.1 | 35.9 | 38.2 |
| Observation | completely melted | completely melted | completely melted |

TABLE 22.6

| Mazerustar KK-300SS-Constant G Force, 180 seconds, variable mass | | | |
|---|---|---|---|
| | Test 4 | Test 10 | Test 12 |
| Lot Number | 617221/A | 617221/A | 617221/A |
| Mass (gram) | 25.03 | 50.02 | 75.03 |
| RPM | 2000 | 2000 | 2000 |
| G Force | 284 | 284 | 284 |
| Time (seconds) | 180 | 180 | 180 |
| Temperature Before (° C.) | 24.3 | 23.8 | 23.3 |
| Temperature After (° C.) | 51.6 | 59.6 | 56.4 |
| ΔT (° C.) | 27.3 | 35.8 | 33.1 |
| Observation | completely melted | completely melted | completely melted |

TABLE 22.7

Mazerustar KK-300SS-Constant G Force, 300 seconds, variable mass

|  | Test 20 | Test 19 | Test 18 | Test 13 |
|---|---|---|---|---|
| Lot Number | 617221/A | 617221/A | 617221/A | 617221/A |
| Mass (gram) | 25.04 | 50.03 | 75.01 | 100.03 |
| RPM | 2000 | 2000 | 2000 | 2000 |
| G Force | 284 | 284 | 284 | 284 |
| Time (seconds) | 300 | 300 | 300 | 300 |
| Temp. Before (° C.) | 24.3 | 24.1 | 25 | 23.4 |
| Temp. After (° C.) | 54.2 | 60.4 | 60.9 | 60.1 |
| ΔT (° C.) | 29.9 | 36.3 | 35.9 | 36.7 |
| Observation | completely melted | completely melted | completely melted | completely melted |

TABLE 22.8

Mazerustar KK-400-75 gram, Constant time, variable G Force

|  | Test 14 | Test 13 | Test 12 |
|---|---|---|---|
| Lot Number | 617221/A | 617221/A | 617221/A |
| Mass (gram) | 75.02 | 75.02 | 75.03 |
| Revolution Setting # | 7 | 8 | 9 |
| Rotation Setting # | 7 | 8 | 9 |
| RPM | 1058 | 1218 | 1340 |
| G Force | 170 | 226 | 273 |
| Time (seconds) | 450 | 450 | 450 |
| Temperature Before (° C.) | 24.5 | 24.5 | 24.3 |
| Temperature After (° C.) | 34.5 | 63.8 | 66.3 |
| ΔT (° C.) | 10.0 | 39.3 | 42.0 |
| Observation | not melted | completely melted | completely melted |

TABLE 22.9

Mazerustar KK-400-25 gram, Constant G Force, variable time

|  | Test 18 | Test 3 | Test 5 | Test 1 |
|---|---|---|---|---|
| Lot Number | 617221/A | 617221/A | 617221/A | 617221/A |
| Mass (gram) | 25.00 | 25.00 | 25.05 | 25.00 |
| Revolution Setting # | 9 | 9 | 9 | 9 |
| Rotation Setting # | 9 | 9 | 9 | 9 |
| RPM | 1340 | 1340 | 1340 | 1340 |
| G Force | 273 | 273 | 273 | 273 |
| Time (seconds) | 180 | 300 | 450 | 600 |
| Temp. Before (° C.) | 23.5 | 24.4 | 24.7 | 24.3 |
| Temp. After (° C.) | 32.2 | 32.6 | 56.3 | 61.8 |
| ΔT (° C.) | 8.7 | 8.2 | 31.6 | 37.5 |
| Observation | not melted | not melted | completely melted | completely melted |

TABLE 22.10

Mazerustar KK-400-50 gram, Constant G Force, variable time

|  | Test 19 | Test 2 | Test 8 | Test 11 |
|---|---|---|---|---|
| Lot Number | 617221/A | 617221/A | 617221/A | 617221/A |
| Mass (gram) | 50.06 | 50.00 | 50.04 | 50.01 |
| Revolution Setting # | 9 | 9 | 9 | 9 |
| Rotation Setting # | 9 | 9 | 9 | 9 |
| RPM | 1340 | 1340 | 1340 | 1340 |
| G Force | 273 | 273 | 273 | 273 |
| Time (seconds) | 180 | 300 | 450 | 600 |
| Temp. Before (° C.) | 24.0 | 24.3 | 23.9 | 24.5 |
| Temp. After (° C.) | 39.9 | 44.8 | 64.2 | 67.5 |
| ΔT (° C.) | 15.9 | 20.5 | 40.3 | 43.0 |
| Observation | partially melted | partially melted | completely melted | completely melted |

TABLE 22.11

Mazerustar KK-400-75 gram, Constant G Force, variable time

|  | Test 10 | Test 6 | Test 12 | Test 15 |
|---|---|---|---|---|
| Lot Number | 617221/A | 617221/A | 617221/A | 617221/A |
| Mass (gram) | 75.06 | 75.01 | 75.03 | 75.02 |
| Revol. Setting # | 9 | 9 | 9 | 9 |
| Rotation Setting # | 9 | 9 | 9 | 9 |
| RPM | 1340 | 1340 | 1340 | 1340 |
| G Force | 273 | 273 | 273 | 273 |
| Time (seconds) | 180 | 300 | 450 | 600 |
| Temp. Before (° C.) | 23.6 | 25.2 | 24.3 | 24.4 |
| Temp. After (° C.) | 33.5 | 65.6 | 66.3 | 69.5 |
| ΔT (° C.) | 9.9 | 40.4 | 42.0 | 45.1 |
| Observation | not melted | completely melted | completely melted | completely melted |

TABLE 22.12

Mazerustar KK-400-100 gram, Constant G Force, variable time

|  | Test 22 | Test 16 | Test 20 |
|---|---|---|---|
| Lot Number | 617221/A | 617221/A | 617221/A |
| Mass (gram) | 100.09 | 100.02 | 100.00 |
| Revolution Setting # | 9 | 9 | 9 |
| Rotation Setting # | 9 | 9 | 9 |
| RPM | 1340 | 1340 | 1340 |
| G Force | 273 | 273 | 273 |
| Time (seconds) | 300 | 450 | 600 |
| Temperature Before (° C.) | 23.4 | 25.0 | 23.6 |
| Temperature After (° C.) | 65.0 | 69.6 | 68.7 |
| ΔT (° C.) | 41.6 | 44.6 | 45.1 |
| Observation | completely melted | completely melted | completely melted |

TABLE 22.13

Mazerustar KK-400-Constant G Force, 180 seconds, variable mass

|  | Test 18 | Test 19 | Test 10 |
|---|---|---|---|
| Lot Number | 617221/A | 617221/A | 617221/A |
| Mass (gram) | 25.00 | 50.06 | 75.06 |
| Revolution Setting # | 9 | 9 | 9 |
| Rotation Setting # | 9 | 9 | 9 |
| RPM | 1340 | 1340 | 1340 |
| G Force | 273 | 273 | 273 |
| Time (seconds) | 180 | 180 | 180 |

TABLE 22.13-continued

Mazerustar KK-400-Constant G Force, 180 seconds, variable mass

|  | Test 18 | Test 19 | Test 10 |
|---|---|---|---|
| Temperature Before (° C.) | 23.5 | 24.0 | 23.6 |
| Temperature After (° C.) | 32.2 | 39.9 | 33.5 |
| ΔT (° C.) | 8.7 | 15.9 | 9.9 |
| Observation | not melted | partially melted | not melted |

TABLE 22.14

Mazerustar KK-400-Constant G Force, 300 seconds, variable mass

|  | Test 3 | Test 2 | Test 6 | Test 22 |
|---|---|---|---|---|
| Lot Number | 617221/A | 617221/A | 617221/A | 617221/A |
| Mass (gram) | 25.00 | 50.00 | 75.01 | 100.09 |
| Revolution Setting # | 9 | 9 | 9 | 9 |
| Rotation Setting # | 9 | 9 | 9 | 9 |
| RPM | 1340 | 1340 | 1340 | 1340 |
| G Force | 273 | 273 | 273 | 273 |
| Time (seconds) | 300 | 300 | 300 | 300 |
| Temp. Before (° C.) | 24.4 | 24.3 | 25.2 | 23.4 |
| Temp. After (° C.) | 32.6 | 44.8 | 65.6 | 65 |
| ΔT (° C.) | 8.2 | 20.5 | 40.4 | 41.6 |
| Observation | not melted | partially melted | completely melted | completely melted |

TABLE 22.15

Mazerustar KK-400-Constant G Force, 450 seconds, variable mass

|  | Test 5 | Test 8 | Test 12 | Test 16 |
|---|---|---|---|---|
| Lot Number | 617221/A | 617221/A | 617221/A | 617221/A |
| Mass (gram) | 25.05 | 50.04 | 75.03 | 100.02 |
| Revolution Setting # | 9 | 9 | 9 | 9 |
| Rotation Setting # | 9 | 9 | 9 | 9 |
| RPM | 1340 | 1340 | 1340 | 1340 |
| G Force | 273 | 273 | 273 | 273 |
| Time (seconds) | 450 | 450 | 450 | 450 |
| Temp. Before (° C.) | 24.7 | 23.9 | 24.3 | 25.0 |
| Temp. After (° C.) | 56.3 | 64.2 | 66.3 | 69.6 |
| ΔT (° C.) | 31.6 | 40.3 | 42 | 44.6 |
| Observation | completely melted | completely melted | completely melted | completely melted |

TABLE 22.16

Mazerustar KK-400-Constant G Force, 600 seconds, variable mass

|  | Test 1 | Test 11 | Test 15 | Test 20 | Test 17 |
|---|---|---|---|---|---|
| Lot Number | 617221/A | 617221/A | 617221/A | 617221/A | 617221/A |
| Mass (gram) | 25.00 | 50.01 | 75.02 | 100.00 | 151.03 |
| Revolution Setting # | 9 | 9 | 9 | 9 | 9 |
| Rotation Setting # | 9 | 9 | 9 | 9 | 9 |
| RPM | 1340 | 1340 | 1340 | 1340 | 1340 |
| G Force | 273 | 273 | 273 | 273 | 273 |
| Time (seconds) | 600 | 600 | 600 | 600 | 600 |
| Temperature Before (° C.) | 24.3 | 24.5 | 24.4 | 23.6 | 23.4 |
| Temperature After (° C.) | 61.8 | 67.5 | 69.5 | 68.7 | 67.5 |
| ΔT (° C.) | 37.5 | 43 | 45.1 | 45.1 | 44.1 |
| Observation | completely melted | completely melted | completely melted | completely melted | completely melted |

TABLE 22.17

Mazerustar KK-1000-200 grams, 450 seconds, variable G Force

|  | Test 7 | Test 6 | Test 2 |
|---|---|---|---|
| Lot Number | 608721/A & 605082/A | 608721/A | 617221/A |
| Mass (gram) | 200.01 | 200.02 | 200.07 |
| Revolution Setting # | 7 | 8 | 9 |
| Rotation Setting # | 7 | 8 | 9 |
| RPM | 770 | 860 | 950 |
| G Force | 149 | 186 | 227 |
| Time (seconds) | 450 | 450 | 450 |
| Temperature Before (° C.) | 23.2 | 22.8 | 24.9 |
| Temperature After (° C.) | 57.5 | 60.6 | 68 |
| ΔT (° C.) | 34.3 | 37.8 | 43.1 |
| Observation | completely melted | completely melted | completely melted |

TABLE 22.18

Mazerustar KK-1000-200 grams, Constant G Force, variable time

|  | Test 9 | Test 4 | Test 2 | Test 5 |
|---|---|---|---|---|
| Lot Number | 605082/A | 617221/A | 617221/A | 617221/A |
| Mass (gram) | 200.15 | 200.20 | 200.07 | 200.05 |
| Revolution Setting # | 9 | 9 | 9 | 9 |
| Rotation Setting # | 9 | 9 | 9 | 9 |
| RPM | 950 | 950 | 950 | 950 |
| G Force | 227 | 227 | 227 | 227 |
| Time (seconds) | 180 | 300 | 450 | 600 |
| Temperature Before (° C.) | 23.0 | 24.5 | 24.9 | 24.9 |
| Temperature After (° C.) | 63.6 | 63.8 | 68.0 | 72.8 |
| ΔT (° C.) | 40.6 | 39.3 | 43.1 | 47.9 |
| Observation | completely melted | completely melted | completely melted | completely melted |

TABLE 22.19

Mazerustar KK-1000-Constant G Force, 450 seconds, variable mass

|  | Test 1 | Test 2 | Test 3 | Test 8 |
|---|---|---|---|---|
| Lot Number | 617221/A | 617221/A | 617221/A | 608721/A |
| Mass (gram) | 100.05 | 200.07 | 300.09 | 525.53 |

TABLE 22.19-continued

Mazerustar KK-1000-Constant G Force, 450 seconds, variable mass

|  | Test 1 | Test 2 | Test 3 | Test 8 |
|---|---|---|---|---|
| Revolution Setting # | 9 | 9 | 9 | 9 |
| Rotation Setting # | 9 | 9 | 9 | 9 |
| RPM | 950 | 950 | 950 | 950 |
| G Force | 227 | 227 | 227 | 227 |
| Time (seconds) | 450 | 450 | 450 | 450 |
| Temperature Before (° C.) | 24.9 | 24.9 | 24.7 | 23.4 |
| Temperature After (° C.) | 33.0 | 68.0 | 71.2 | 67.7 |
| ΔT (° C.) | 8.1 | 43.1 | 46.5 | 44.3 |
| Observation | not melted | completely melted | completely melted | completely melted |

Hot Plate

TABLE 22.20

Hot Plate

|  | Test 1 | Test 2 | Test 3 |
|---|---|---|---|
| Lot Number | 10810/B | 10810/B | 608721/A |
| Mass (gram) | 50.325 | 70.273 | 100.090 |
| Time (seconds) | 559 | 790 | 1059 |
| Temperature Before (° C.) | 24.5 | 24.5 | 24.5 |
| Temperature After (° C.) | 59.1 | 59.6 | 58.4 |
| ΔT (° C.) | 34.6 | 35.1 | 33.9 |
| Observation | completely melted | completely melted | completely melted |

Material and Methods
Hot Plate

A water bath was set with a water temperature of 65° C. A hot plate Thermos Scientific Cimarec™ model SP131325 was used. A beaker of size Pyrex™ number 1003 with capacity 1000 ml, 4 in diameter and 6 in in height, was used to contain the water. A beaker of size Veegee™ Glassco number 20229 with capacity 600 ml, 3.5 in diameter and 5 in in height, was used to contain the gelatin. The gelatin gum base was placed in the melting beaker and the timer was started. The water temperature of 65° C. was maintained while briefly mixing every 3 minutes. Time was recorded once all gelatin cubes had melted. Final temperature of melted gelatin gum base was recorded. This experimental assessment was reproduced for 50, 75 and 100 grams.

Mazerustar KK-300SS, KK-400 and KK-1000

A two (2) decimal place balance was used to weight the gelatin gum base. During the weighing operations, a plastic jar was placed on the balance and tared. Various amounts of gelatin gum base were tested due to the varying capacities of the different planetary mixers, the weights of 25, 50, 75, 100, 120, 150, 200, 300 and 500 grams were selected. The temperature was recorded using a digital thermometer with stainless steel probe by inserting the tip inside of the gelatin gum base. The final temperature was measured by repeating the process and swirling the stainless steel probe as to avoid coagulation as much as possible.

Mazerustar KK-300SS

Parameters of 180 seconds time period in combination with 25, 50 and 75 grams were used for increasing G Force and RPM. For the Mazerustar KK-300SS: 182 G Force corresponds to 1600 RPM; 230 G Force corresponds to 1800 RPM; and 284 G Force corresponds to 2000 RPM.

Parameters of G Force of 284 (2000 RPM) in combination with 75 grams were used for increasing the time of melting in the Mazerustar. For the Mazerustar KK-300SS times of 180, 300 and 450 seconds were used.

Parameters of G force of 284 (2000 RPM) in combination with 180 seconds were used for increasing the mass of melting in the Mazerustar. For the Mazerustar KK-300SS mass of 25, 50 and 75 grams were used.

Parameters of G Force of 284 (2000 RPM) in combination with 300 seconds were used for increasing the mass of melting in the Mazerustar. For the Mazerustar KK-300SS mass of 25, 50, 75 and 100 grams were used.

Mazerustar KK-400

Parameters of 450 seconds time period in combination with 75 grams were used for increasing G Force and RPM. For the Mazerustar KK-400: 170 G Force corresponds to 1058 RPM; 226 G Force corresponds to 1218 RPM; and 273 G Force corresponds to 1340 RPM.

Parameters of G Force of 273 (1340 RPM) in combination with 25, 50 and 75 grams were used for increasing the time of melting in the Mazerustar. For the Mazerustar KK-400 times of 180, 300, 450 and 600 seconds were used.

Parameters of G Force of 273 (1340 RPM) in combination with 100 grams were used for increasing the time of melting in the Mazerustar. For the Mazerustar KK-400 times of 300, 450 and 600 seconds were used.

Parameters of G force of 273 (1340 RPM) in combination with 180 seconds were used for increasing the mass of melting in the Mazerustar. For the Mazerustar KK-400 mass of 25, 50 and 75 grams were used.

Parameters of G force of 284 (2000 RPM) in combination with 300 and 450 seconds were used for increasing the mass of melting in the Mazerustar. For the Mazerustar KK-400 mass of 25, 50, 75 and 100 grams were used.

Parameters of G force of 284 (2000 RPM) in combination with 600 seconds were used for increasing the mass of melting in the Mazerustar. For the Mazerustar KK-400 mass of 25, 50, 75, 100 and 150 grams were used.

Mazerustar KK-1000

Parameters of 450 seconds time period in combination with 200 grams were used for increasing G Force and RPM. For the Mazerustar KK-1000: 149 G Force corresponds to 770 RPM; 186 G Force corresponds to 860 RPM; and 227 G Force corresponds to 950 RPM.

Parameters of G Force of 227 (950 RPM) in combination with 200 grams were used for increasing the time of melting in the Mazerustar. For the Mazerustar KK-1000 times of 180, 300, 450 and 600 seconds were used.

Parameters of G force of 227 (950 RPM) in combination with 450 seconds were used for increasing the mass of melting in the Mazerustar. For the Mazerustar KK-1000 mass of 100, 200, 300 and 500 grams were used.

Results and Discussion

Figure 36:
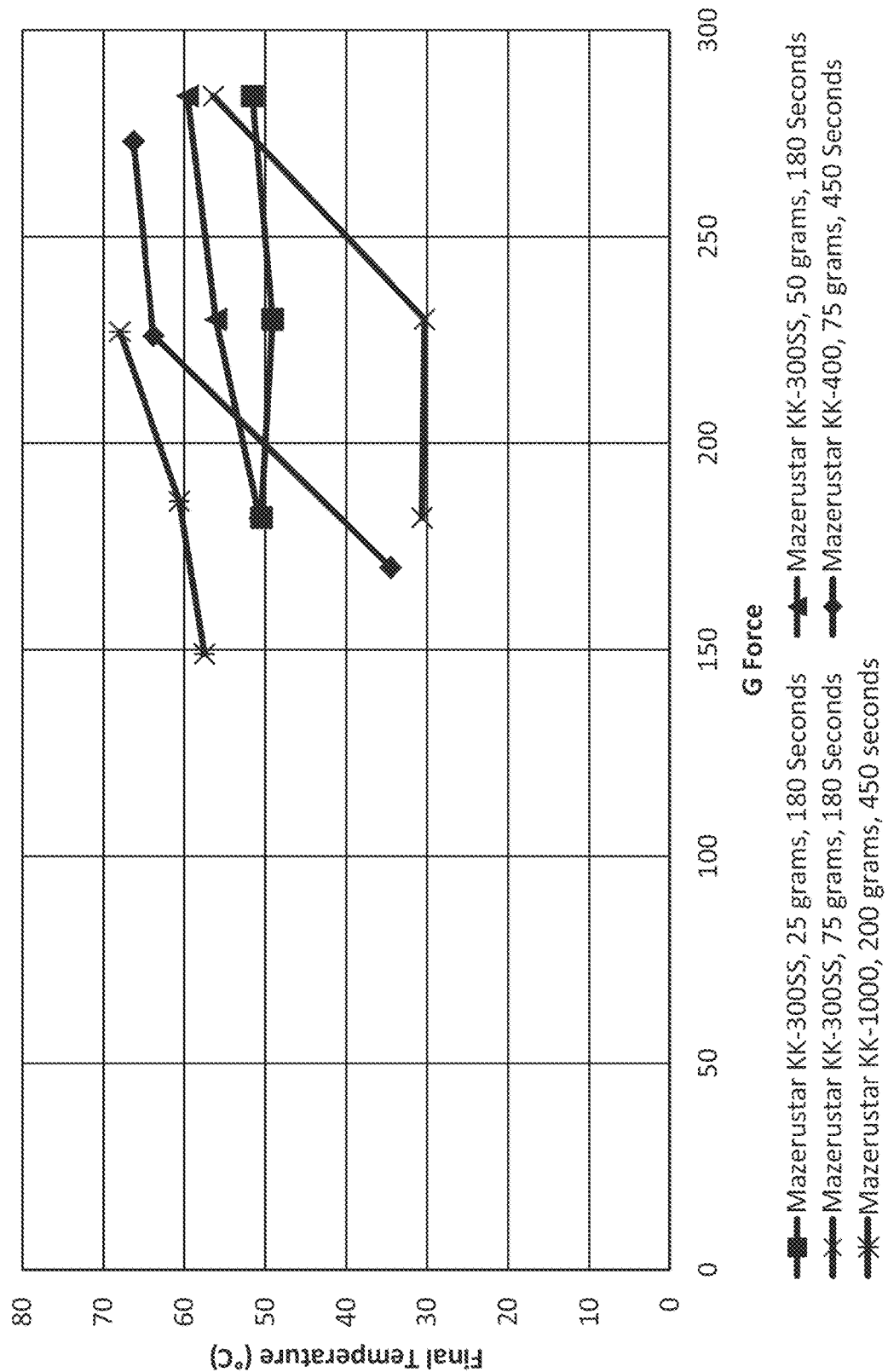
FIG. 36 represents a non-limiting graph showing melting of gum base gelatin when processed using superimposed revolution and rotation movements based on parameters of constant time and increasing G Force, in accordance with an implementation of the present invention.
Figure 37:
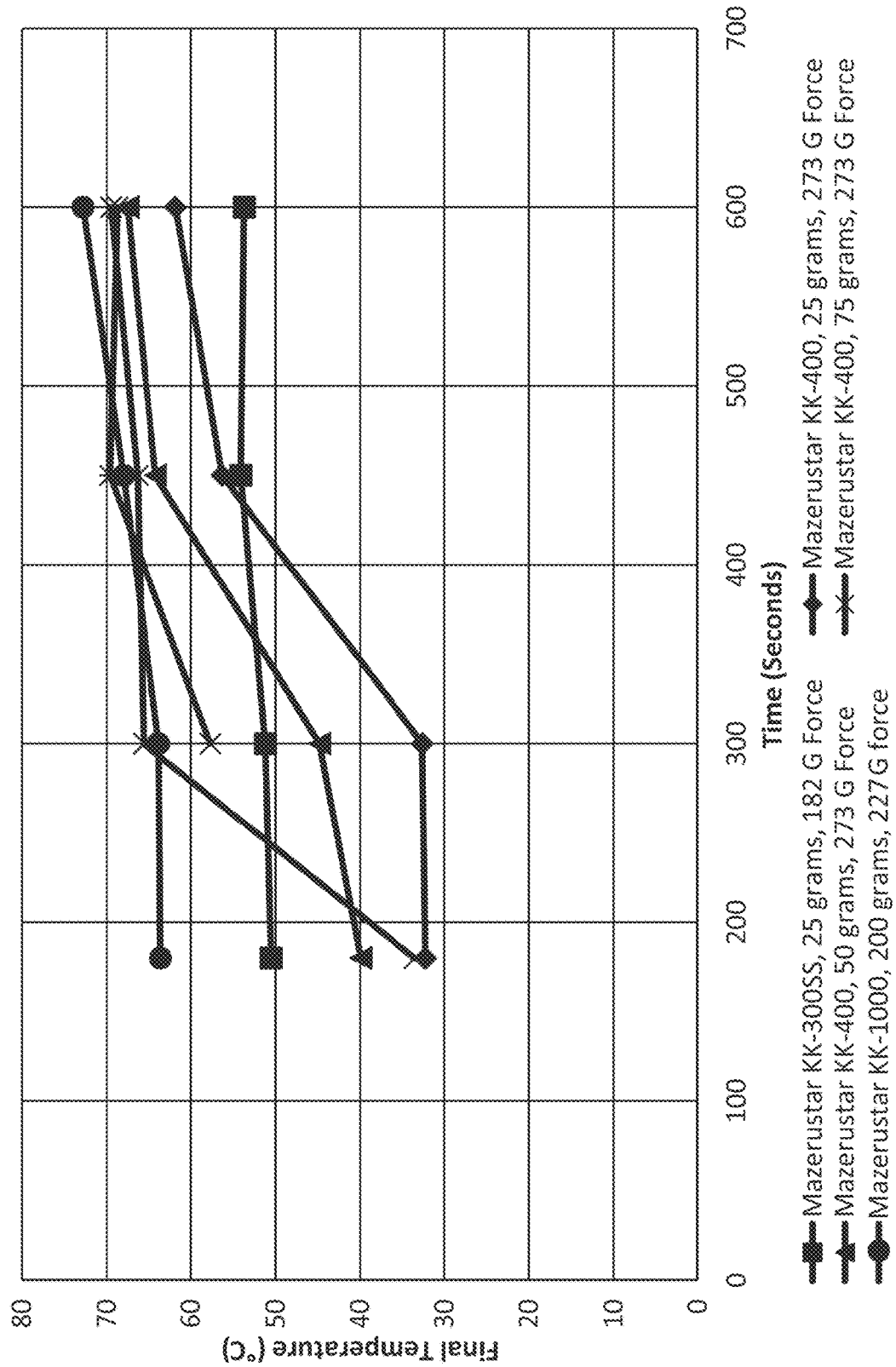
FIG. 37 represents a non-limiting graph showing melting of gum base gelatin when processed using superimposed revolution and rotation movements based on parameters of constant G force and increasing time, in accordance with an implementation of the present invention.
Figure 38:
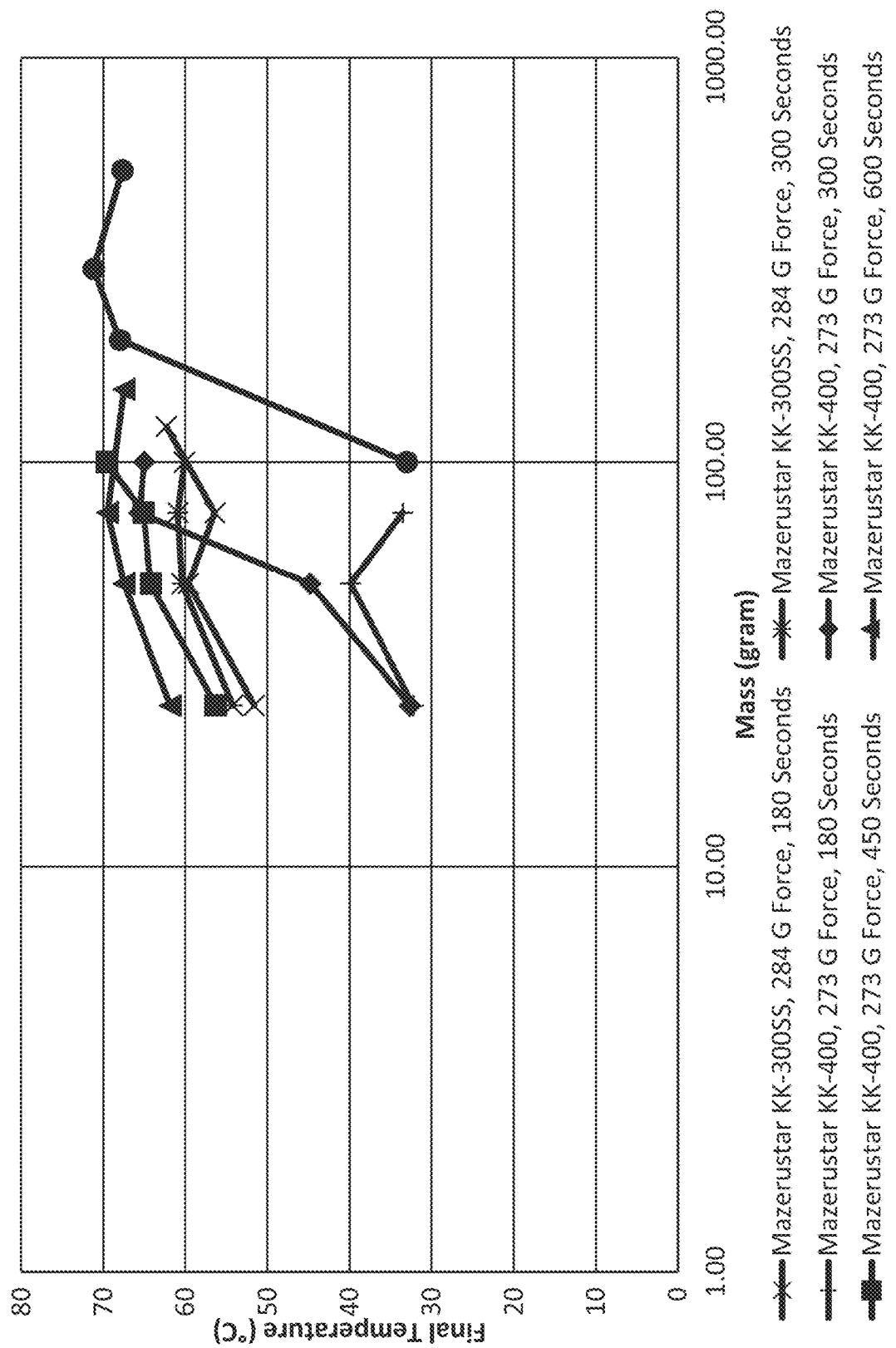
FIG. 38 represents a non-limiting graph showing melting of gum base gelatin when processed using superimposed revolution and rotation movements based on parameters of constant G force and time, while increasing the mass, in accordance with an implementation of the present invention.
Figure 39:
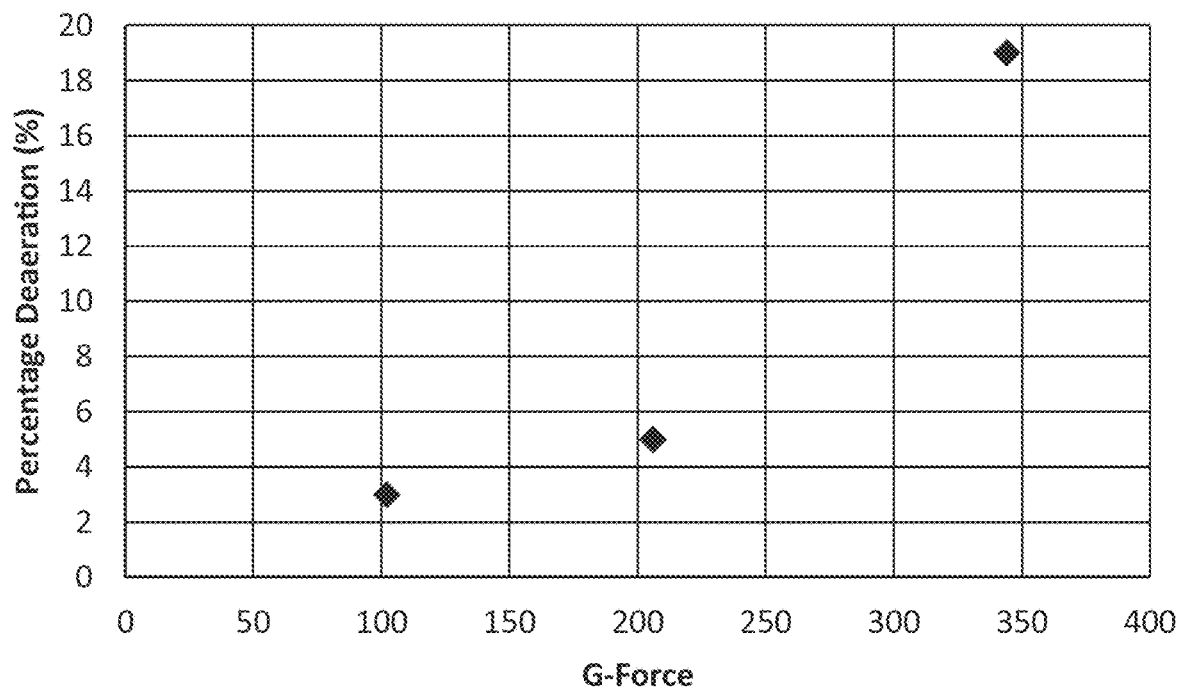
FIG. 39 represents a non-limiting graph showing percentage de-aeration of a personalized composition when processed using superimposed revolution and rotation movements based on parameters of constant time and variable G force, in accordance with an implementation of the present invention.
Figure 40:
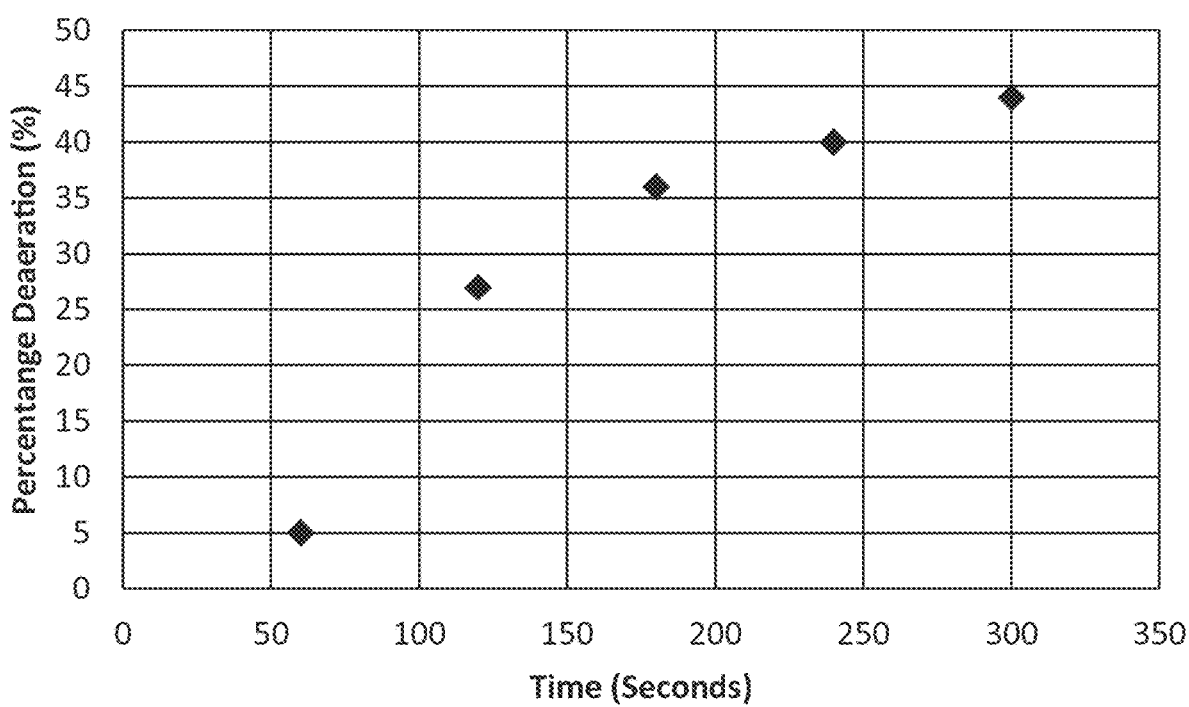
FIG. 40 represents a non-limiting graph showing percentage de-aeration of a personalized composition when processed using superimposed revolution and rotation movements based on parameters of constant G force and variable time, in accordance with an implementation of the present invention.
Figure 41:
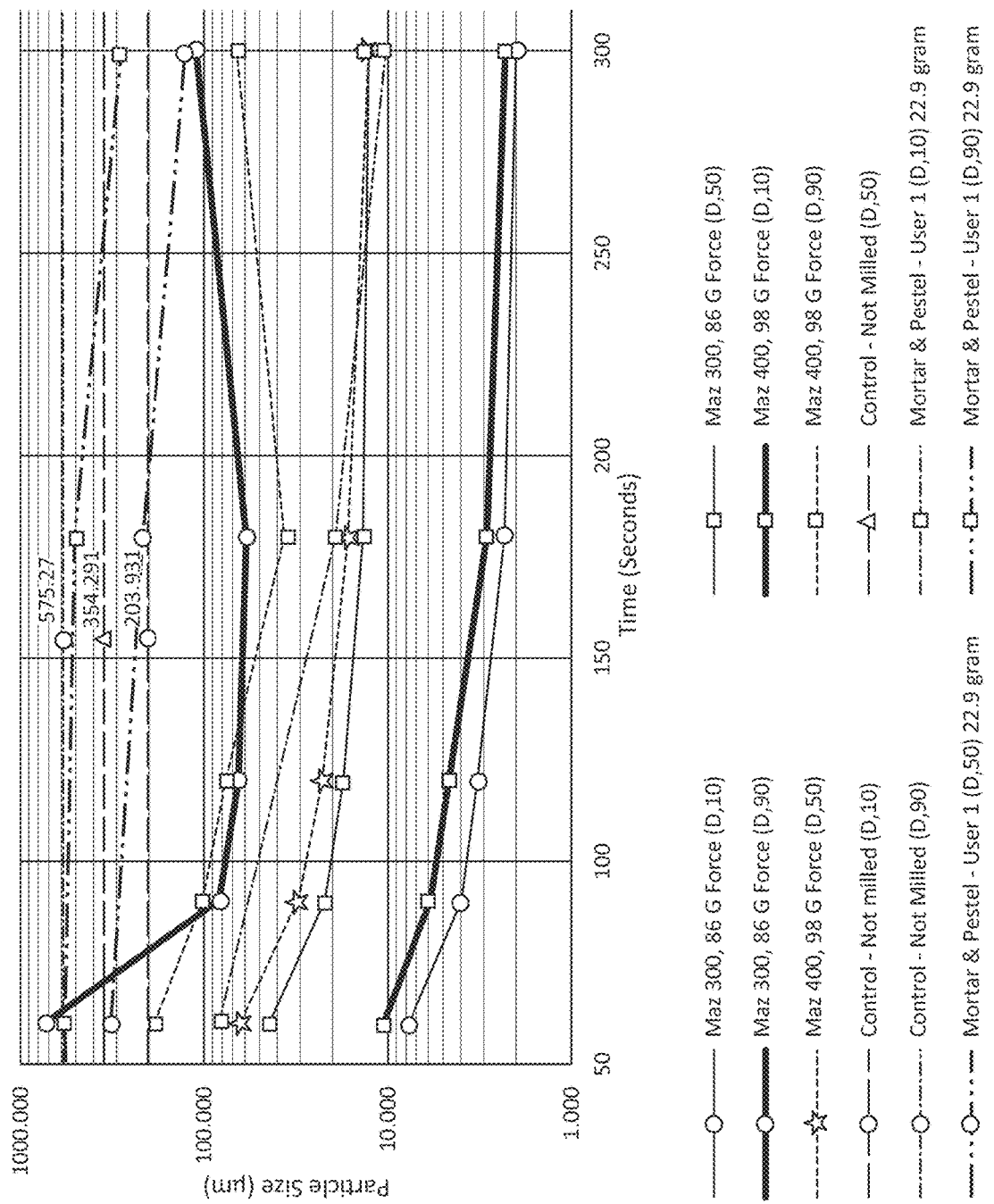
FIG. 41 represents a non-limiting graph showing particle size (µm) with respect to D10, D50 and D90 of 23 gram of NaCl when processed using superimposed revolution and rotation movements based on parameters of constant G Force in presence of grinding media or when processed with control mortar and pestle, in accordance with an implementation of the present invention.
Figure 42:
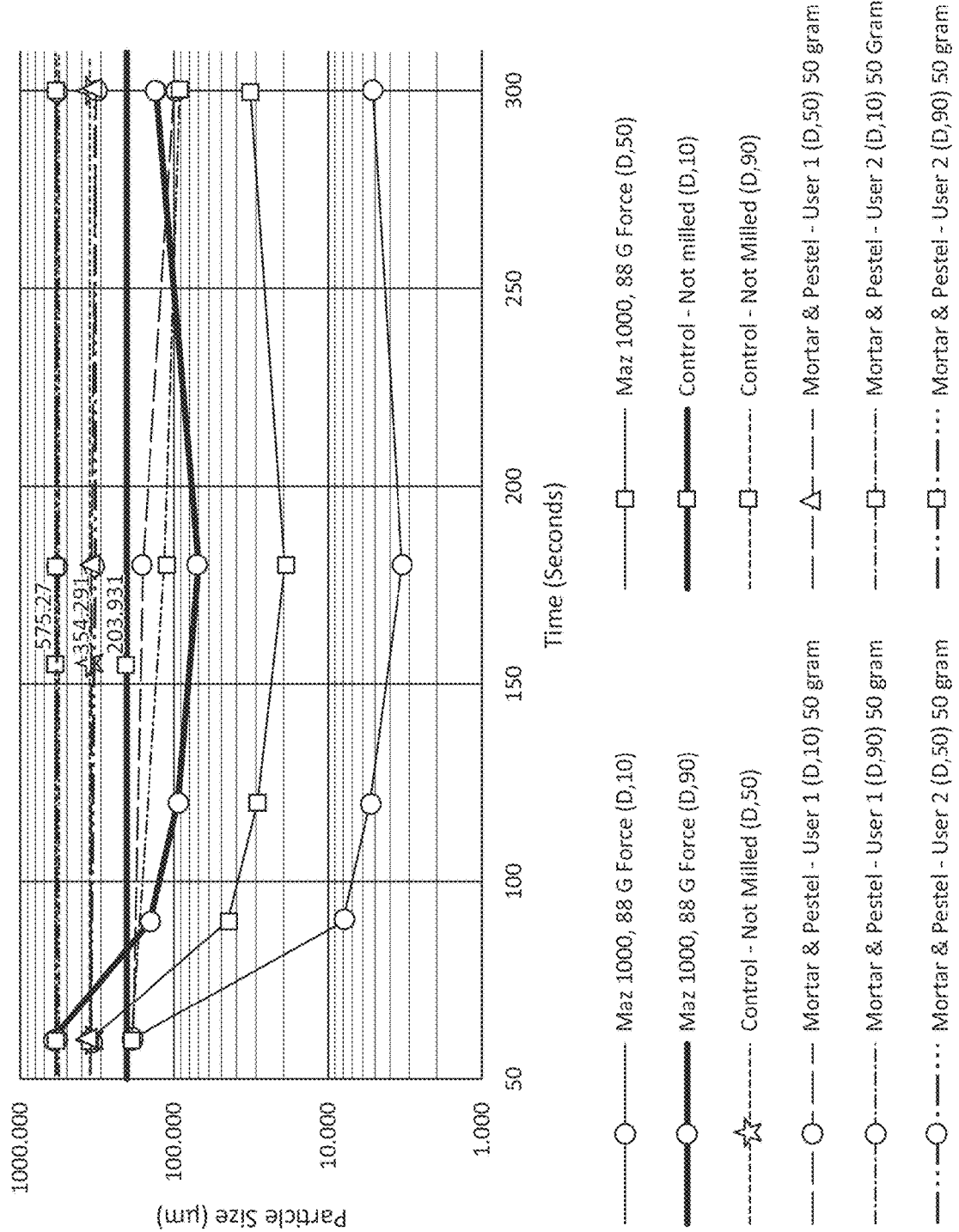
FIG. 42 represents a non-limiting graph showing particle size (µm) with respect to D10, D50 and D90 of 50 gram of NaCl when processed using superimposed revolution and rotation movements based on parameters of constant G Force in presence of grinding media or when processed with control mortar and pestle, in accordance with an implementation of the present invention.
Figure 43:
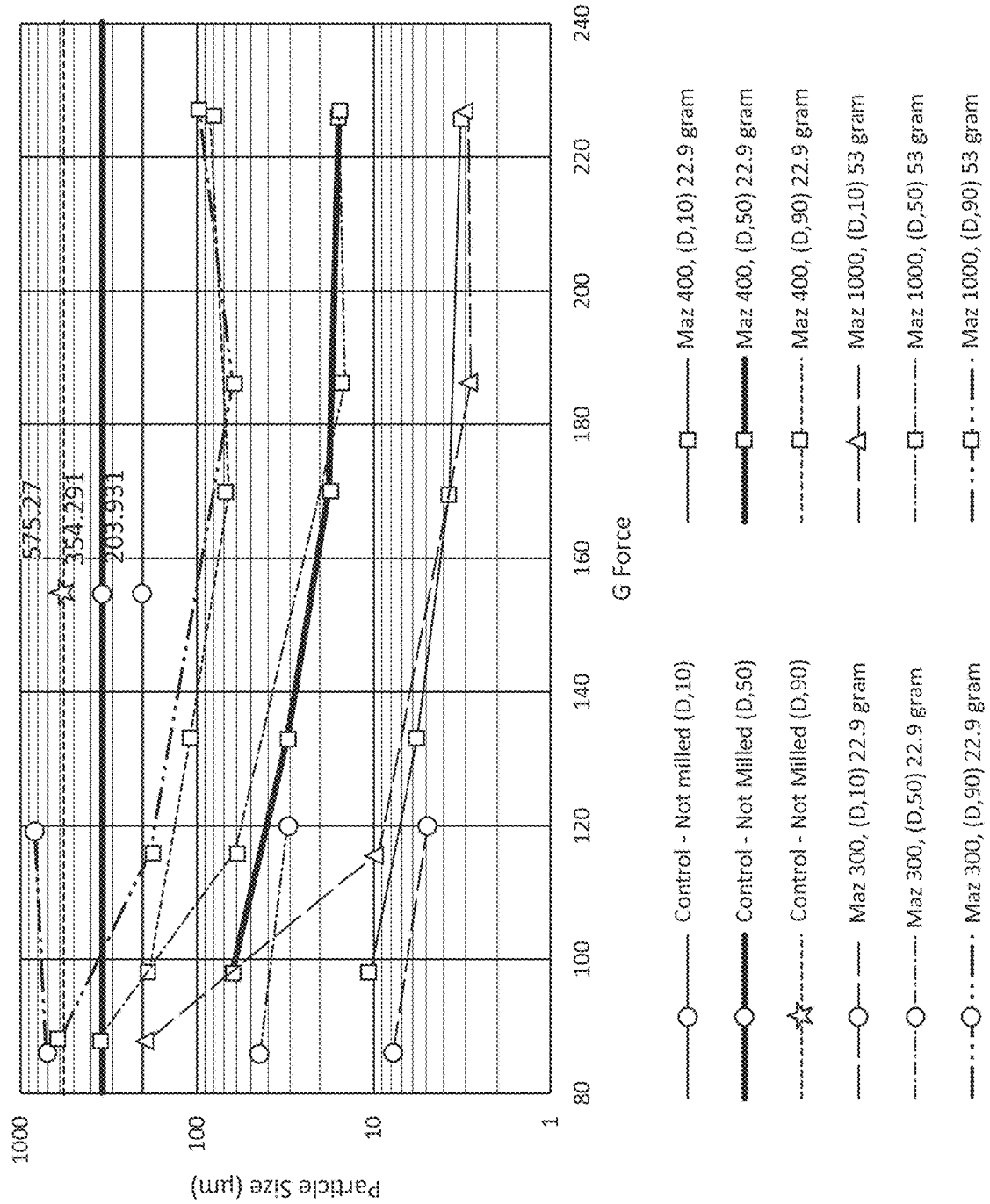
FIG. 43 represents a non-limiting graph showing particle size (µm) with respect to D10, D50 and D90 of 22.9 gram of NaCl when processed using superimposed revolution and rotation movements based on parameters of 60 seconds in presence of grinding media or when processed with control mortar and pestle, in accordance with an implementation of the present invention.
Figure 44:
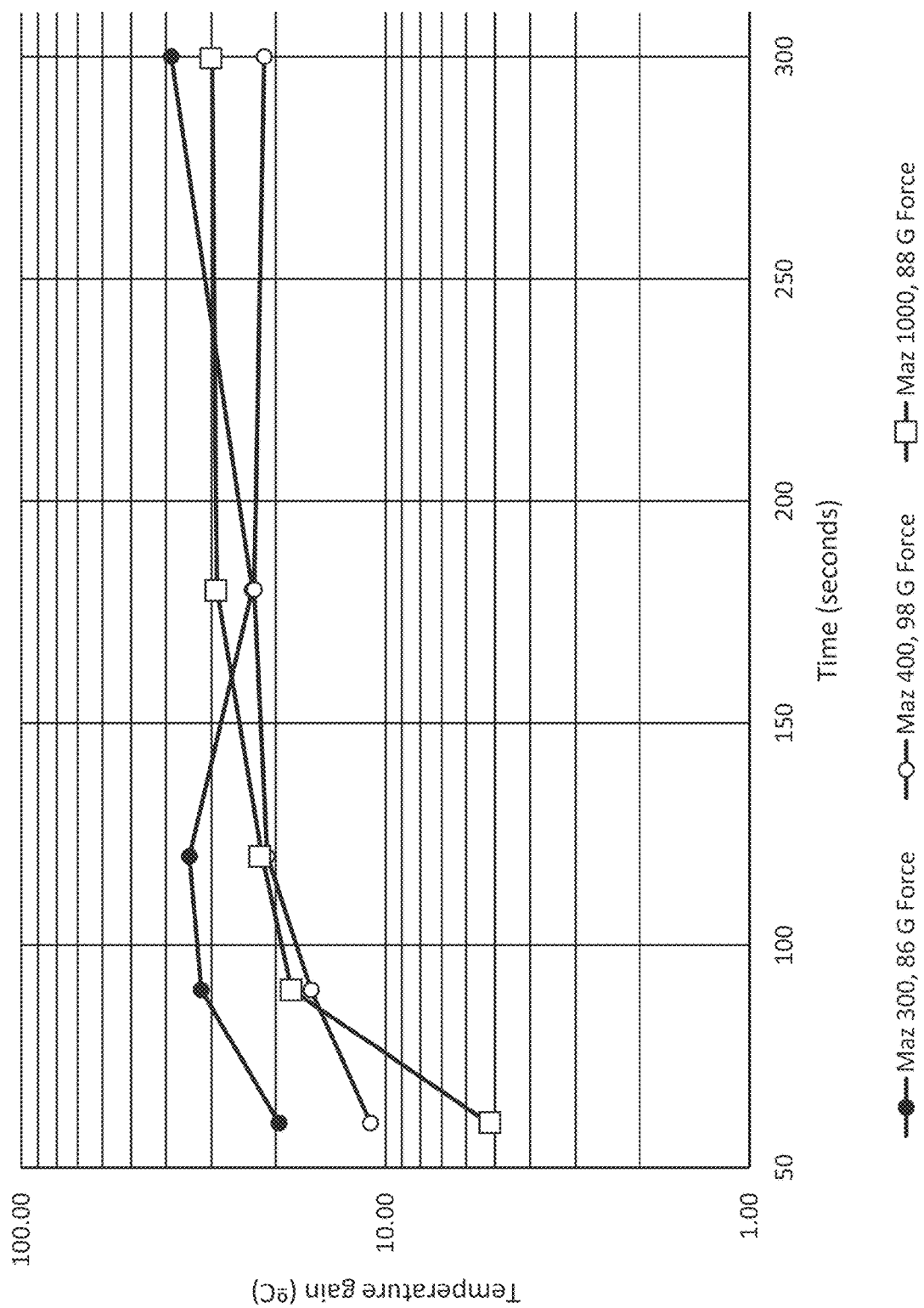
FIG. 44 represents a non-limiting graph showing temperature increase (gain in degrees Celsius) when processing NaCl when processed using superimposed revolution and rotation movements based on parameters of constant G force and increasing time period in presence of grinding media, in accordance with an implementation of the present invention.
Figure 45:
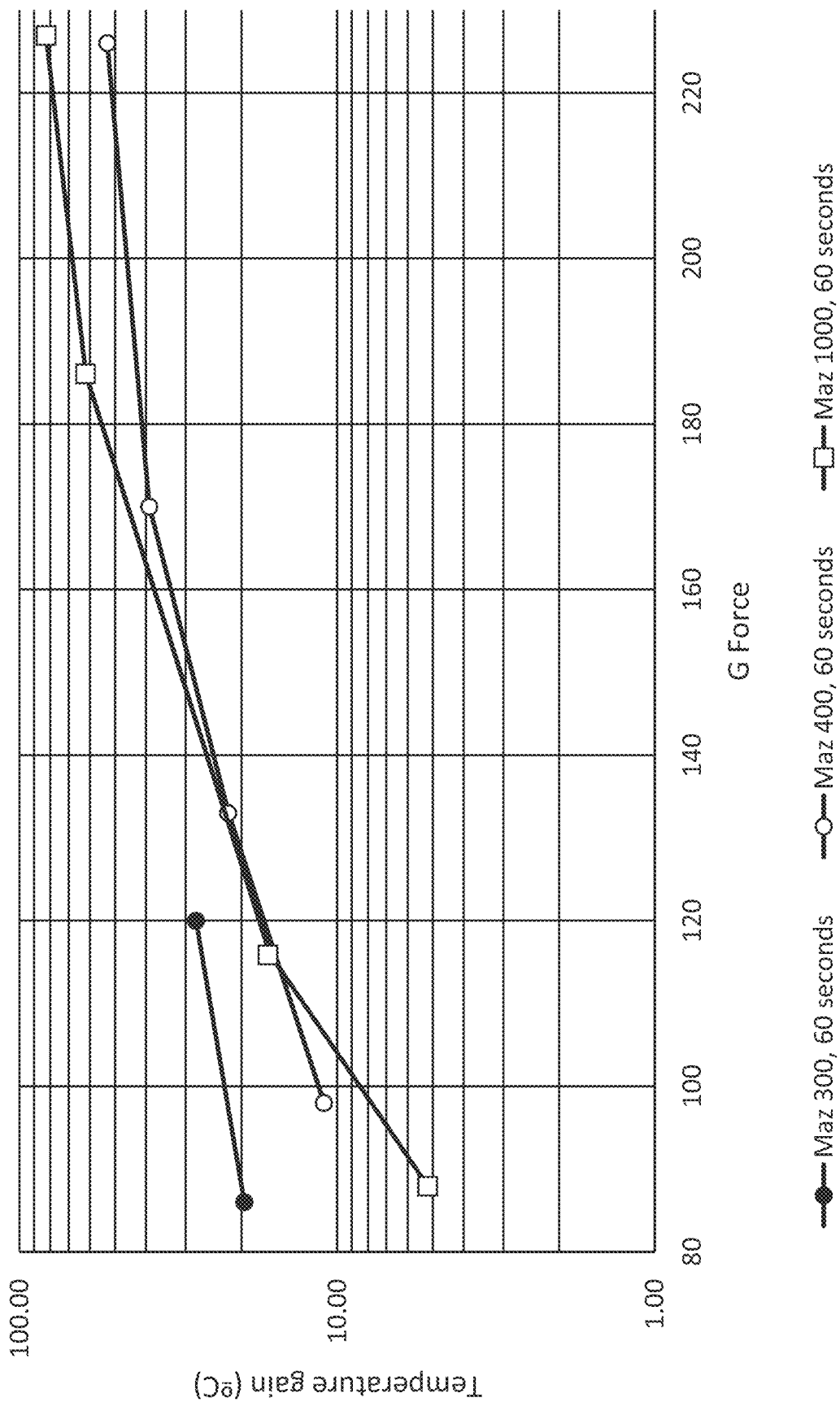
FIG. 45 represents a non-limiting graph showing temperature increase (gain in degrees Celsius) when processing NaCl when processed using superimposed revolution and rotation movements based on parameters of constant time period and increasing G force in presence of grinding media, in accordance with an implementation of the present invention.

The following can be deduced from the results reported in tables 20 and 20.1 to 20.20 as well as in FIGS. 36-38.

The gelatin particles melted as the planetary motion induced friction between the particles and the inside surfaces of the jar. By nature, gelatin gum base has an adhesive surface. The gelatin gum base chunk volume and mass increased proportionally. However, the surface area adhering to the plastic of the same chunk of gelatin gum base also increased but at a lower rate than the mass. The smaller the mass of the gelatin chunk, the more difficulty the planetary mixer had of dislodging the mass of gelatin stuck on the wall and, thus, not being able to melt.

The results show that that there was a direct correlation between melting and the planetary mixer's G Force/RPM speed, time and mass of gum base gelatin. The final temperature of the melted substance increased as the G Force/

RPM speed increased and the time increased. The final temperature of the melted substance followed a quadratic function, where a minimal and a maximal mass can be used to melt the gelatin gum base.

Example 10

In this example, an Unguator cartridge was used to disperse ingredients the herein described superimposed revolution and rotation movements. The cartridge is fitted with an adaptor to fit the Unguator cartridge into a receiving basket of the planetary mixer. The ingredients used were a pharmaceutically acceptable carrier, excipient or diluent, Versapro Cream Base and a red dye, as a tracer. The amount of Versapro added into the Unguator cartridge was the nominal value recommended by the Unguator manufacturer. The dispersed cream was then visually assessed for red dye homogeneity dispersion. Note that the rotation speed (rpm) was kept at a value of 40% of the revolution speed (rpm).

TABLE 23

| Versapro in Unguator cartridge | | | |
|---|---|---|---|
| Volume of Unguator cartridge | revolution (rpm) | Temperature (° C.), Time | Observation |
| 15 ml | 400 | 25.1 (120 sec) | Not completely homogeneous mix, very light color in the middle. |
|  | 1000 | 23.7 (30 sec) 25.7 (120 sec) | Dye reached the bottom, homogeneous mix (30 and 120 sec) |
|  | 1500 | 24.1 (30 sec) 26.2 (120 sec) | Dye reached the bottom, homogeneous mix (30 and 120 sec) |
|  | 2000 |  | No leakage beyond the piston. However, jar came loose from the lid and cream spilled out. |
| 20 ml | 400 | 24.1 (120 sec) | Not completely homogeneous, lighter color in the middle (30 sec). Dye reached the bottom, homogeneous mix and uniform color. (120 sec) |
|  | 1000 | 25.8 (30 sec) 25.8 (120 sec) | Dye reached the bottom, homogeneous mix and uniform color (30 sec and 120 sec) |
|  | 1500 | 25.8 (30 sec) 26.3 (120 sec) | Dye reached the bottom, homogeneous mix and uniform color (30 sec and 120 sec) |
|  | 2000 |  | No leakage beyond the piston. However, jar came loose and detached from the lid and cream spilled out. |
| 30 ml | 400 |  | Dye did not reach the bottom, not a homogeneous mix. (30 sec and 120 sec) |
|  | 1000 | 23.2 (30 sec) 24.6 (120 sec) | Dye reached the bottom, homogeneous mix (30 sec and 120 sec) |
|  | 1500 | 23.1 (30 sec) | Dye reached the bottom, homogeneous mix (30 sec) No leakage beyond the piston. However, jar came loose and detached from the lid and cream spilled out. (60 sec) |
|  | 2000 | — | — |
| 50 ml | 400 | 23.9 (120 sec) | Dye did not reach the bottom, not a homogeneous mix (30 sec) Dye reached the bottom, homogeneous mix and uniform color. (120 sec) |
|  | 1000 | 23.1 (30 sec) 25.1 (120 sec) | Dye reached the bottom, homogeneous mix (30 sec and 120 sec) |
|  | 1500 |  | No leakage beyond the piston. However, jar came loose and detached from the lid and cream spilled out. (30 sec) |
| 100 ml | 400 | 23.1 (120 sec) | Dye did not reach the bottom, not a homogeneous mix (30 sec) Dye reached the bottom, homogeneous mix and uniform color. (120 sec) |
|  | 1000 | 24.2 (30 sec) 24.2 (120 sec) | Dye reached the bottom, homogeneous mix (30 sec) |
|  | 1500 | 23.2 (30 sec) | Dye reached the bottom, homogeneous mix and uniform color. However, jar had become slightly loose from the lid. (30 sec) No leakage beyond the piston. However, jar came loose and detached from the lid and cream spilled out. (60 sec) |

Safe dispersing parameters so as to avoid leakage, thus, appear to be 1000 rpm at 0.5 min, and are applicable to all sizes of the Unguator cartridge line of containers with the herein described adapters.

Example 11

In this example, grinding of variable amounts of ingredient particles was performed the herein described superimposed revolution and rotation movements in a planetary mixer (Mazerustar kk-300ss, kk-400 or kk-1000) in presence of grinding media. The container was filled with grinding media and the ingredient particles. The dispersing time and the dispersing speed parameters were modified, and a dispersing assessment was made, as indicated in the following tables.

It is to be noted that this tables make reference to particle size distribution values such as $D_{10}$, $D_{50}$ and $D_{90}$. These are known manners to represent particle size distribution. For example, $D_{90}$ signifies the point in the size distribution, up to and including which, 90% of the total volume of material in the sample is 'contained'. For example, if the $D_{90}$ is 844 nm, this means that 90% of the sample has a size of 844 nm or smaller.

TABLE 24

Standard NaCl particle size (LOT number 613788, NDC 0629)

| | |
|---|---|
| Surface Weighted Mean (μm) | 248.715 |
| Volume Weighted Mean (μm) | 371.042 |
| $D_{10}$ (μm) | 203.931 |
| $D_{50}$ (μm) | 354.291 |
| $D_{90}$ (μm) | 575.27 |

TABLE 25

Mazerustar KK-300SS-Constant time, variable G Force

| | Test 1 | Test 2 | Test 3 | Test 4 |
|---|---|---|---|---|
| NaCl (grams) | 22.90 | 22.90 | 22.90 | 22.90 |
| RPM | 1100 | 1300 | 1600 | 1800 |
| G Force | 86 | 120 | 182 | 230 |
| Time (seconds) | 60 | 60 | 60 | 60 |
| Surface Weighted Mean (μm) | 17.011 | 10.850 | N/A | N/A |
| Volume Weighted Mean (μm) | 171.164 | 178.076 | N/A | N/A |
| $D_{10}$ (μm) | 7.593 | 5.077 | N/A | N/A |
| $D_{50}$ (μm) | 44.899 | 31.239 | N/A | N/A |
| $D_{90}$ (μm) | 725.785 | 826.723 | N/A | N/A |
| Temperature Before (° C.) | 23.7 | 24.2 | N/A | N/A |
| Temperature After (° C.) | 43.3 | 52.0 | N/A | N/A |

TABLE 26

Mazerustar KK-300SS-Variable time, constant G Force

| | Test 1 | Test 6 | Test 7 | Test 8 | Test 9 |
|---|---|---|---|---|---|
| NaCl (grams) | 22.90 | 22.90 | 22.90 | 22.90 | 22.90 |
| RPM | 1100 | 1100 | 1100 | 1100 | 1100 |
| G Force | 86 | 86 | 86 | 86 | 86 |
| Time (seconds) | 60 | 90 | 120 | 180 | 300 |
| Surface Weighted Mean (μm) | 17.011 | 7.933 | 6.284 | 4.956 | 4.56 |
| Volume Weighted Mean (μm) | 171.164 | 41.888 | 32.521 | 32.939 | 42.691 |
| $D_{10}$ (μm) | 7.593 | 3.992 | 3.190 | 2.292 | 2.012 |
| $D_{50}$ (μm) | 44.899 | 21.823 | 17.793 | 14.002 | 12.835 |
| $D_{90}$ (μm) | 725.785 | 81.408 | 66.279 | 59.787 | 109.449 |

TABLE 26-continued

Mazerustar KK-300SS-Variable time, constant G Force

| | Test 1 | Test 6 | Test 7 | Test 8 | Test 9 |
|---|---|---|---|---|---|
| Temperature Before (° C.) | 23.7 | 22.1 | 24.3 | 23.5 | 26.0 |
| Temperature After (° C.) | 43.3 | 54.1 | 58.8 | 46.7 | 64.7 |

TABLE 27

Mazerustar KK-400-Constant time, variable G Force

| | Test 1 | Test 2 | Test 3 | Test 4 |
|---|---|---|---|---|
| NaCl (grams) | 22.90 | 22.90 | 22.90 | 22.90 |
| Revolution Setting # | 5 | 6 | 7 | 8 |
| Rotation Setting # | 5 | 6 | 7 | 8 |
| RPM | 804 | 935 | 1058 | 1218 |
| G Force | 98 | 133 | 170 | 226 |
| Time (seconds) | 60 | 60 | 60 | 60 |
| Surface Weighted Mean (μm) | 23.095 | 11.283 | 6.553 | 5.915 |
| Volume Weighted Mean (μm) | 81.929 | 57.473 | 32.390 | 36.968 |
| $D_{10}$ (μm) | 10.468 | 5.624 | 3.592 | 3.083 |
| $D_{50}$ (μm) | 64.028 | 31.677 | 17.864 | 15.731 |
| $D_{90}$ (μm) | 181.26 | 107.833 | 68.490 | 83.828 |
| Temperature Before (° C.) | 23.1 | 25.3 | 24.7 | 25.5 |
| Temperature After (° C.) | 34.1 | 47.3 | 63.7 | 78.4 |

TABLE 28

Mazerustar 400-Variable time, constant G Force

| | Test 1 | Test 6 | Test 7 | Test 8 | Test 9 |
|---|---|---|---|---|---|
| NaCl (grams) | 22.90 | 22.90 | 22.90 | 22.90 | 22.90 |
| Revolution Setting # | 5 | 5 | 5 | 5 | 5 |
| Rotation Setting # | 5 | 5 | 5 | 5 | 5 |
| RPM | 804 | 804 | 804 | 804 | 804 |
| G Force | 98 | 98 | 98 | 98 | 98 |
| Time (seconds) | 60 | 90 | 120 | 180 | 300 |
| Surface Weighted Mean (μm) | 23.095 | 11.527 | 8.580 | 5.84 | 4.82 |
| Volume Weighted Mean (μm) | 81.929 | 44.4229 | 33.358 | 35.459 | 33.206 |
| $D_{10}$ (μm) | 10.468 | 5.889 | 4.613 | 2.864 | 2.278 |
| $D_{50}$ (μm) | 64.028 | 31.852 | 22.848 | 16.457 | 13.084 |
| $D_{90}$ (μm) | 181.26 | 101.156 | 76.524 | 35.459 | 66.116 |
| Temperature Before (° C.) | 23.1 | 26.6 | 24.9 | 26.9 | 26.3 |
| Temperature After (° C.) | 34.1 | 42.6 | 46.0 | 49.8 | 47.8 |

Methods
Reference Point

The Sodium Chloride (NaCl) powder was taken from the original packaged container (LOT number: 613788) with a stainless steel laboratory spatula and placed in an inert plastic container. The powder (NaCl) was transferred to the laser diffraction particle sizer MasterSizer 2000®. The data was collected and the distribution was noted at $D_{10}$, $D_{50}$ and $D_{90}$. These measurements consist of the reference points for the following milling experimental assay.

Mortar and Pestle

A two (2) decimal place balance was used to weight the Sodium Chloride (NaCl) powder (LOT #613788). During the weighing operations, a weigh boat was placed on the balance and tared, two different amounts of powder (NaCl) were tested, i.e., 23 grams and 50 grams. Due to the volume capacity difference of the planetary mixers tested, the weights of 23 grams and 50 grams were selected. The results gathered from the 23 grams trituration steps were used to compare with the KK-300SS and KK-400. The results gathered from the 50 grams trituration steps were used to compare with the KK-1000. Once the desired mass of powder was weighed, the powder (NaCl) was then transferred from the weigh boat to a mortar and pestle. The triturating process began once the timer started. During testing, times of 60, 180 and 300 seconds were used. Also, two (2) different individuals performed the trituration process. Once the time of a trituration run had elapsed, the milled powder (NaCl) was transferred from the mortar to an inert plastic container. A random sample of 3 grams from the powder was placed in the laser diffraction particle sizer MasterSizer 2000®. The data was collected and the distribution was noted at $D_{10}$, $D_{50}$ and $D_{90}$. These measurements consisted of the reference points for the following milling experimental assay.

Mazerustar KK-300SS, KK-400 and KK-1000

A two (2) decimal place balance was used to weigh the Sodium Chloride (NaCl) powder (LOT #613788). During the weighing operations, a stainless steel liner was placed on the balance and tared. Two different amounts of powder (NaCl), 22.90 grams and 53.00 grams, which each occupied ¼ of the volume of their respective liners, were tested. The 22.90 grams experiments were tested on the Mazerustar KK-300SS and KK-400 units. The 53.00 grams experiments were tested on the Mazerustar KK-1000 unit. Once the desired mass of powder was weighed, the spherical grinding media of 8 mm diameter was added to the stainless steel container. For this experiment a total grinding media mass of 106.4 grams was used for the experiments with 22.90 grams of powder, and a total grinding media mass of 245.79 grams was used for the experiments with 53.00 grams of powder.

Mazerustar KK-300SS

Times of 60 seconds were used for increasing G Force and RPM. For the Mazerustar KK-300SS: 86 G Force corresponds to 1100 RPM; 120 G Force corresponds to 1300 RPM; 182 G Force corresponds to 1600 RPM; 230 G Force corresponds to 1800 RPM.

Parameters of G Force of 86 (1100 RPM) were used for increasing the time of milling in the Mazerustar. For the Mazerustar KK-300SS times of 60, 90, 120, 180 and 300 seconds were used.

Mazerustar KK-400

Parameters of 60 seconds were used for increasing G Force and RPM. For the Mazerustar KK-400: 98 G Force corresponds to 804 RPM; 133 G Force corresponds to 935 RPM; 170 G Force corresponds to 1058 RPM; and 226 G Force corresponds to 1218 RPM.

Parameters of G Force of 98 (804 RPM) were used for increasing the time of milling in the planetary mixer. For the Mazerustar KK-400 times of 60, 90, 120, 180 and 300 seconds were used.

Mazerustar KK-1000

Parameters of 60 seconds were used for increasing G Force and RPM. For the Mazerustar KK-1000: 88 G Force corresponds to 590 RPM; 116 G Force corresponds to 680 RPM; 186 G Force corresponds to 960 RPM; 227 G Force corresponds to 960 RPM.

Parameters of G Force of 88 (590 RPM) were used for increasing the time of milling in the planetary mixer. For the Mazerustar KK-1000 times of 60, 90, 120, 180 and 300 seconds were used.

Once the time had elapsed, the milled powder was placed in an inert plastic container. A random sample of 3 grams from the powder was placed in the laser diffraction particle sizer MasterSizer 2000®. The data was collected and the distribution was noted at $D_{10}$, $D_{50}$ and $D_{90}$. These measurements were the reference points for the following milling experimental assay.

Clean up for the planetary mixer and for the mortar and pestle took comparatively the same period of time.

Observations

Constant G Force with Increased Time Duration

One can observe that compounding pharmaceutical ingredients using the herein described superimposed revolution and rotation movements in the presence of grinding media with a planetary mixer is very efficient compared to the conventional method of the mortar and pestle.

The longer the duration, the finer the particles became. After 60 seconds, the planetary mixer could bring the ($D_{10}$) within 10 μm. The mortar and pestle could barely reach ($D_{10}$) of 10 μm after 300 seconds. It is important to note the overall particle size for the ($D_{50}$) and ($D_{90}$). The planetary mixer could reduce the particle size within 60 seconds for the overall particle size for the ($D_{50}$) and ($D_{90}$). After processing with the planetary mixer for a duration exceeding 180 seconds, the powder reached a state whereby the fineness of the powder exhibited hygroscopic properties of clumping, creating larger particle size.

Constant Time Duration with Increased G Force

One can observe that milling at higher G Force for the same duration diminished the particle size in the planetary mixer. G Forces higher than 170 demonstrated that particle size variance was very similar.

Temperature Gain for 60 Seconds at Different G Force

Increasing the G Force while maintaining a constant time milling time of 60 seconds generated more friction between the stainless steel liner and the zirconium coated balls, which in turn created a larger temperature gain. This temperature gain stabilised once the 180 G Force mark was passed.

Temperature Gain for Constant G Force at Different Time Duration

The temperature gain increased as the processing time increases. The temperature gain stabilised quickly for any value after the 90-second marks.

TABLE 29

Mazerustar KK-1000-Constant time, variable G Force

| | Test 1 | Test 2 | Test 3 | Test 4 |
|---|---|---|---|---|
| NaCl (grams) | 53.00 | 53.00 | 53.00 | 53.00 |
| Revolution Setting # | 5 | 6 | 8 | 9 |
| Rotation Setting # | 5 | 6 | 8 | 9 |
| RPM | 590 | 680 | 860 | 960 |
| G Force | 88 | 116 | 186 | 227 |
| Time (seconds) | 60 | 60 | 60 | 60 |
| Surface Weighted Mean (μm) | 190.024 | 20.891 | 5.586 | 5.964 |
| Volume Weighted Mean (μm) | 375.514 | 80.659 | 28.893 | 40.497 |
| $D_{10}$ (μm) | 184.331 | 9.437 | 2.845 | 2.900 |
| $D_{50}$ (μm) | 361.686 | 60.390 | 15.174 | 15.937 |
| $D_{90}$ (μm) | 602.621 | 182.817 | 63.131 | 97.955 |
| Temperature Before (° C.) | 22.7 | 25.6 | 23.7 | 24.8 |
| Temperature After (° C.) | 27.9 | 41.9 | 85.5 | 107.4 |

TABLE 30

Mazerustar 1000-Variable time, constant G Force

| | Test 1 | Test 6 | Test 7 | Test 8 | Test 9 |
|---|---|---|---|---|---|
| NaCl (grams) | 53.00 | 53.00 | 53.00 | 53.00 | 53.00 |
| Rev # | 5 | 5 | 5 | 5 | 5 |
| Rot # | 5 | 5 | 5 | 5 | 5 |
| RPM | 590 | 590 | 590 | 590 | 590 |

TABLE 30-continued

Mazerustar 1000-Variable time, constant G Force

|  | Test 1 | Test 6 | Test 7 | Test 8 | Test 9 |
|---|---|---|---|---|---|
| G Force | 88 | 88 | 88 | 88 | 88 |
| Time (seconds) | 60 | 90 | 120 | 180 | 300 |
| Surface Weighted Mean (μm) | 190.024 | 17.128 | 10.585 | 6.498 | 10.365 |
| Vol. Weighted Mean (μm) | 375.514 | 69.509 | 40.890 | 33.689 | 96.187 |
| $D_{10}$ (μm) | 184.331 | 7.750 | 5.386 | 3.295 | 5.12 |
| $D_{50}$ (μm) | 361.686 | 45.419 | 28.919 | 19.327 | 32.163 |
| $D_{90}$ (μm) | 602.621 | 141.883 | 93.219 | 68.821 | 127.26 |
| Temperature Before (° C.) | 22.7 | 24.8 | 26.4 | 24.9 | 24.9 |
| Temperature After (° C.) | 27.9 | 42.9 | 48.2 | 53.9 | 54.8 |

TABLE 31

Mortar & Pestle-Variable time & weight

| User | Test 1 User 1 | Test 2 User 1 | Test 3 User 1 | Test 4 User 2 | Test 5 User 2 | Test 6 User 2 |
|---|---|---|---|---|---|---|
| NaCl (grams) | 22.90 | 22.90 | 22.90 | 22.90 | 22.90 | 22.90 |
| Time (seconds) | 60 | 180 | 300 | 60 | 180 | 300 |
| $D_{10}$ (μm) | 79.86 | 19.108 | 10.27 | 128.563 | 26.732 | 8.070 |
| $D_{50}$ (μm) | 322.183 | 218.789 | 127.252 | 329.516 | 253.368 | 103.698 |
| $D_{90}$ (μm) | 564.429 | 459.647 | 326.609 | 567.004 | 493.422 | 287.631 |
| Temp. Before (° C.) | 25.6 | 26.3 | 26.8 | N/A | N/A | N/A |
| Temp. After (° C.) | 26.3 | 26.8 | 27.0 | N/A | N/A | N/A |

TABLE 32

Mortar & Pestle-Variable time & weight

| User | Test 7 User 1 | Test 8 User 1 | Test 9 User 1 | Test 10 User 2 | Test 11 User 2 | Test 12 User 2 |
|---|---|---|---|---|---|---|
| NaCl (grams) | 50.00 | 50.00 | 50.00 | 50.00 | 50.00 | 50.00 |
| Time (seconds) | 60 | 180 | 300 | 60 | 180 | 300 |
| $D_{10}$ (μm) | 187.352 | 157.311 | 99.553 | 184.351 | 114.791 | 89.662 |
| $D_{50}$ (μm) | 358.969 | 346.437 | 327.158 | 348.63 | 331.814 | 322.701 |
| $D_{90}$ (μm) | 593.531 | 586.343 | 567.563 | 584.389 | 575.718 | 561.756 |
| Temperature Before (° C.) | 25.1 | 24.7 | 25.4 | N/A | N/A | N/A |
| Temperature After (° C.) | 24.7 | 25.4 | 25.4 | N/A | N/A | N/A |

Example 12

In the following experiment, a compounding composition including 3 API was dispersed in an excipient was prepared according to the herein described superimposed revolution and rotation movements, or using an Electric Mortar and Pestle (EMP) Mixer as control comparative mixing device. The characteristics of the resulting composition were assessed. Notably, this experiment demonstrated that the superimposed revolution and rotation movements can be implemented independently of the processing capacity or planetary mixer model used.

Homogeneity was assessed by measuring the API potency with high performance liquid chromatography (HPLC) at three layers of a given mixing vessel (top, middle and bottom layers). The API potency was reported in the form of a weight/weight concentration on triplicate batches. In other words, the formulation for a given container and volume size was repeated three (3) times in order to obtain statistically significant data.

The assays were performed with different planetary mixer models, namely the Mazerustar KK-300SS, KK-400W, and KK-1000W and an EMP Mixer.

Samples were prepared using six (6) different mixer/volume configurations with a formula of Baclofen 2%, Cyclobenzaprine 6% and Diclofenac 10% in VersaPro™ Cream. Briefly, the baclofen and cyclobenzaprine hydrochloride were weighted into separate glass mortar and pestles. The baclofen and cyclobenzaprine hydrochloride were triturated until a fine powder with no grittiness was formed. In a glass mortar and pestle the desired quantity of baclofen, cyclobenzaprine hydrochloride and diclofenac sodium were combined. Desired amounts of ethoxy diglycol and pentylene glycol were incorporated into the powder blend until the powder blend was levigated and a smooth paste was achieved.

The dispersing container (Mazerustar or EMP jar) was filled with the desired amount of Versapro Cream and placed into the respective device (planetary Mazerustar or EMP). The parameters for operating the devices were set, including revolution, rotation and time variables for the planetary mixers.

The resulting 3 API formulation composition were separated in the container into three layers, namely top (T), middle (M) and bottom (B) layers.

TABLE 33

List of Ingredients for 3-API Formulation

| Ingredient | 1 KK-300SS (200 g) | 2 KK-400W (300 g) | 3 KK-1000W (750 g) | | 4 EMP (200 g) | 5 EMP (300 g) | 6 EMP (750 g) | NDC | Lot |
|---|---|---|---|---|---|---|---|---|---|
| | grams or mL | | | | | | | | |
| Baclofen USP | 4 | 6 | 15 | Baclofen USP | 4 | 6 | 15 | Baclofen USP | |
| Cyclobenzaprine Hydrochloride USP | 12 | 18 | 45 | Cyclobenzaprine Hydrochloride USP | 12 | 18 | 45 | Cyclobenzaprine Hydrochloride USP | |
| Diclofenac Sodium USP (Micronized) | 20 | 30 | 75 | Diclofenac Sodium USP (Micronized) | 20 | 30 | 75 | Diclofenac Sodium USP (Micronized) | |
| Ethoxy Diglycol | 9 | 13.5 | 36 | Ethoxy Diglycol | 9 | 13.5 | 36 | Ethoxy Diglycol | |
| Pentylene Glycol | 8 | 12 | 30 | Pentylene Glycol | 8 | 12 | 30 | Pentylene Glycol | |
| VersaPro Cream Base | 147 | 220.5 | 549 | VersaPro Cream Base | 147 | 220.5 | 549 | VersaPro Cream Base | |

The superimposed revolution and rotation movement parameters in the planetary mixer were (samples 1-3):

1. Mazerustar KK-300SS: 2000 RPM (revolution)/800 RPM (rotation) for 30 sec (standard jar) [which provides a G force of 284 g]
2. Mazerustar KK-400W: 1340 RPM (revolution)/1340 RPM (rotation) for 70 sec [which provides a G force of 273 g]
3. Mazerustar KK-1000W: 960 RPM (revolution)/950 RPM (rotation) for 130 sec [which provides a G force of 227 g]

The EMP parameters were (samples 4-6):

4. EMP 200 mL Jar: Lift Engine Step 01, Mix Engine Step 06 for 120 sec
5. EMP 300 mL Jar: Lift Engine Step 01, Mix Engine Step 06 for 120 sec
6. EMP 1 L Jar: Lift Engine Step 01, Mix Engine Step 06 for 180 sec Each of the resulting composition was then separated in top, middle and bottom layers and the concentration of each of the 3 API in each layer was measured with HPLC. The average concentration ([ ]), the standard deviation (SD) and the relative standard deviation (% RSD) were calculated for each API. The results are shown in the following Tables:

TABLE 34

Results for a composition including 3 API dispersed in Mazerustar KK-300SS

| Formulation # | Sample # | Layer (top, middle, bottom) | Baclofen (w/w) | Cyclobenzaprine (w/w) | Diclofenac (w/w) |
|---|---|---|---|---|---|
| 1 | 1 | Top | 2.045 | 6.144 | 10.045 |
| | 2 | Middle | 2.019 | 6.070 | 9.925 |
| | 3 | Bottom | 2.070 | 6.175 | 10.114 |
| 2 | 4 | Top | 1.992 | 6.129 | 9.970 |
| | 5 | Middle | 2.085 | 6.251 | 10.156 |
| | 6 | Bottom | 2.032 | 6.270 | 10.191 |
| 3 | 7 | Top | 2.071 | 6.334 | 10.319 |
| | 8 | Middle | 2.070 | 6.311 | 10.265 |
| | 9 | Bottom | 2.116 | 6.421 | 10.456 |

TABLE 35

Results for a composition including 3 API dispersed in Mazerustar KK-400W

| Formulation # | Sample # | Layer (top, middle, bottom) | Baclofen (w/w) | Cyclobenzaprine (w/w) | Diclofenac (w/w) |
|---|---|---|---|---|---|
| 4 | 10 | Top | 2.089 | 6.332 | 10.334 |
| | 11 | Middle | 2.113 | 6.345 | 10.375 |
| | 12 | Bottom | 2.127 | 6.316 | 10.352 |
| 5 | 13 | Top | 2.069 | 6.340 | 10.292 |
| | 14 | Middle | 2.090 | 6.426 | 10.486 |
| | 15 | Bottom | 2.051 | 6.397 | 10.438 |
| 6 | 16 | Top | 2.067 | 6.321 | 10.306 |
| | 17 | Middle | 2.094 | 6.312 | 10.3 |
| | 18 | Bottom | 2.081 | 6.394 | 10.41 |

TABLE 36

Results for a composition including 3 API dispersed in Mazerustar KK-1000W

| Formulation # | Sample # | Layer (top, middle, bottom) | Baclofen (w/w) | Cyclobenzaprine (w/w) | Diclofenac (w/w) |
|---|---|---|---|---|---|
| 7 | 19 | Top | 2.085 | 6.432 | 10.556 |
| | 20 | Middle | 2.068 | 6.435 | 10.535 |
| | 21 | Bottom | 2.039 | 6.295 | 10.32 |
| 8 | 22 | Top | 2.105 | 6.426 | 10.374 |
| | 23 | Middle | 2.106 | 6.427 | 10.389 |
| | 24 | Bottom | 2.086 | 6.46 | 10.418 |
| 9 | 25 | Top | 2.130 | 6.369 | 10.382 |
| | 26 | Middle | 2.108 | 6.224 | 10.179 |
| | 27 | Bottom | 2.107 | 6.294 | 10.28 |

TABLE 37

Results for a composition including 3 API dispersed in EMP 200 mL Jar

| Formulation # | Sample # | Layer (top, middle, bottom) | Baclofen (w/w) | Cyclobenzaprine (w/w) | Diclofenac (w/w) |
|---|---|---|---|---|---|
| 10 | 28 | Top | 2.165 | 6.475 | 10.612 |
| | 29 | Middle | 2.021 | 6.089 | 9.985 |
| | 30 | Bottom | 2.024 | 6.11 | 10.021 |
| 11 | 31 | Top | 2.133 | 6.44 | 10.536 |
| | 32 | Middle | 2.12 | 6.288 | 10.285 |
| | 33 | Bottom | 2.05 | 6.212 | 10.169 |
| 12 | 34 | Top | 2.209 | 6.457 | 10.565 |
| | 35 | Middle | 2.074 | 6.182 | 10.136 |
| | 36 | Bottom | 2.113 | 6.279 | 10.288 |

TABLE 38

Results for a composition including 3 API dispersed in EMP 300 ml Jar

| Formulation # | Sample # | Layer (top, middle, bottom) | Baclofen (w/w) | Cyclobenzaprine (w/w) | Diclofenac (w/w) |
|---|---|---|---|---|---|
| 13 | 37 | Top | 2.235 | 6.674 | 10.935 |
| | 38 | Middle | 2.082 | 6.272 | 10.295 |
| | 39 | Bottom | 2.208 | 6.48 | 10.604 |
| 14 | 40 | Top | 2.185 | 6.557 | 10.752 |
| | 41 | Middle | 2.087 | 6.205 | 10.15 |
| | 42 | Bottom | 1.998 | 6.047 | 9.908 |
| 15 | 43 | Top | 2.23 | 6.743 | 11.035 |
| | 44 | Middle | 2.089 | 6.228 | 10.205 |
| | 45 | Bottom | 2.044 | 6.216 | 10.193 |

TABLE 39

Results for a composition including 3 API dispersed in EMP 1 L Jar

| Formulation # | Sample # | Layer (top, middle, bottom) | Baclofen (w/w) | Cyclobenzaprine (w/w) | Diclofenac (w/w) |
|---|---|---|---|---|---|
| 16 | 46 | Top | 2.113 | 6.376 | 10.454 |
| | 47 | Middle | 2.073 | 6.097 | 10.003 |
| | 48 | Bottom | 2.101 | 6.147 | 10.093 |
| 17 | 49 | Top | 2.031 | 6.294 | 10.301 |
| | 50 | Middle | 2.094 | 6.488 | 10.558 |
| | 51 | Bottom | 1.987 | 6.182 | 10.021 |
| 18 | 52 | Top | 2.098 | 6.396 | 10.284 |
| | 53 | Middle | 2.154 | 6.506 | 10.486 |
| | 54 | Bottom | 2.088 | 6.182 | 9.932 |

TABLE 40

% RSD Results for the compositions of Table 34 to 39

| Formulation # | Baclofen, 2% | Cyclobenzaprine, 6% | Diclofenac, 10% |
|---|---|---|---|
| | | % RSD | |
| 1 | 1.2% | 0.9% | 1.0% |
| 2 | 2.3% | 1.2% | 1.2% |
| 3 | 1.3% | 0.9% | 1.0% |
| 4 | 0.9% | 0.2% | 0.2% |
| 5 | 0.9% | 0.7% | 1.0% |
| 6 | 0.6% | 0.7% | 0.6% |
| 7 | 1.1% | 1.3% | 1.2% |
| 8 | 0.5% | 0.3% | 0.2% |
| 9 | 0.6% | 1.2% | 1.0% |
| 10 | 4.0% | 3.5% | 3.4% |
| 11 | 2.1% | 1.8% | 1.8% |
| 12 | 3.3% | 2.2% | 2.1% |
| 13 | 3.8% | 3.1% | 3.0% |
| 14 | 4.5% | 4.2% | 4.2% |
| 15 | 4.6% | 4.7% | 4.6% |
| 16 | 1.0% | 2.4% | 2.3% |
| 17 | 2.6% | 2.4% | 2.6% |
| 18 | 1.7% | 2.6% | 2.7% |

Example 13

In the following experiment, a compounding composition including 2 API was dispersed in an excipient was prepared according to the herein described superimposed revolution and rotation movements, or using an Electric Mortar and Pestle (EMP) Mixer as control comparative mixing device. The characteristics of the resulting composition were assessed. Notably, this experiment demonstrated that the superimposed revolution and rotation movements can be implemented independently of the processing capacity or planetary mixer model used.

Homogeneity was assessed as in Example 12. The dispersing processes were performed with the same devices as in Example 12.

Samples were prepared using six (6) different mixer/volume configurations with a formula of Estradiol 0.05% and Estriol 0.2% in VersaPro Cream. Briefly, the estradiol and estriol were weighted into separate plastic weigh boats. A 3 decimal place balance was used to prepare the formulation. Desired amounts of propylene glycol were incorporated into the powder blend until the powder blend was levigated and a smooth homogeneous liquid. The dispersing container (Mazerustar or EMP jar) was filled with the desired amount of Versapro Cream and placed into the respective device (planetary Mazerustar or EMP). The parameters for operating the devices were set, including revolution, rotation and time variables for the planetary mixers.

The resulting 2 API formulation composition were separated in the container into three layers, namely top (T), middle (M) and bottom (B) layers.

TABLE 41

List of Ingredients for 2-API Formulation

| Ingredient | 1 KK-300SS (200 g) | 2 KK-400 (300 g) | 3 KK-1000 (750 g) | 4 EMP (200 g) | 5 EMP (300 g) | 6 EMP (750 g) | NDC | Lot |
|---|---|---|---|---|---|---|---|---|
| Estradiol, USP (Micronized) | 0.1 | 0.15 | 0.375 | 0.1 | 0.15 | 0.375 | 0869 | 614901/B |
| Estriol USP (Micronized) | 0.4 | 0.6 | 1.5 | 0.4 | 0.6 | 1.5 | 0732 | 615107/B |
| Propylene Glycol | 1 | 1.5 | 3.75 | 1 | 1.5 | 3.75 | 0510 | 605764/C |
| VersaPro Cream Base | 198.5 | 297.75 | 744.375 | 198.5 | 297.75 | 744.375 | 2529 | 611448 |

The superimposed revolution and rotation movement parameters in the planetary mixer (samples 1-3) and the EMP parameters (samples 4-6) were the same as in Example 12.

Each of the resulting composition was then separated and analyzed as in Example 12. The results are shown in the following Tables:

TABLE 42

Results for a composition including 2 API dispersed in KK-300SS

| Formulation # | Sample # | Layer (top, middle, bottom) | Estriol (w/w) | Estradiol (w/w) |
|---|---|---|---|---|
| 19 | 55 | Top | 0.181 | 0.055 |
|  | 56 | Middle | 0.179 | 0.055 |
|  | 57 | Bottom | 0.183 | 0.054 |
| 20 | 58 | Top | 0.211 | 0.046 |
|  | 59 | Middle | 0.204 | 0.044 |
|  | 60 | Bottom | 0.208 | 0.045 |
| 21 | 61 | Top | 0.199 | 0.048 |
|  | 62 | Middle | 0.198 | 0.047 |
|  | 63 | Bottom | 0.196 | 0.047 |

TABLE 43

Results for a composition including 2 API dispersed in Mazerustar KK-400W

| Formulation # | Sample # | Layer (top, middle, bottom) | Estriol (w/w) | Estradiol (w/w) |
|---|---|---|---|---|
| 22 | 64 | Top | 0.195 | 0.049 |
|  | 65 | Middle | 0.194 | 0.048 |
|  | 66 | Bottom | 0.194 | 0.049 |
| 23 | 67 | Top | 0.201 | 0.048 |
|  | 68 | Middle | 0.201 | 0.048 |
|  | 69 | Bottom | 0.201 | 0.048 |
| 24 | 70 | Top | 0.18 | 0.05 |
|  | 71 | Middle | 0.181 | 0.051 |
|  | 72 | Bottom | 0.181 | 0.05 |

TABLE 44

Results for a composition including 2 API dispersed in Mazerustar KK-1000W

| Formulation # | Sample # | Layer (top, middle, bottom) | Estriol (w/w) | Estradiol (w/w) |
|---|---|---|---|---|
| 25 | 73 | Top | 0.201 | 0.05 |
|  | 74 | Middle | 0.203 | 0.051 |
|  | 75 | Bottom | 0.202 | 0.05 |
| 26 | 76 | Top | 0.198 | 0.037 |
|  | 77 | Middle | 0.198 | 0.037 |
|  | 78 | Bottom | 0.197 | 0.037 |
| 27 | 79 | Top | 0.203 | 0.051 |
|  | 80 | Middle | 0.201 | 0.051 |
|  | 81 | Bottom | 0.201 | 0.051 |

TABLE 45

Results for a composition including 2 API dispersed in EMP 200 mL Jar

| Formulation # | Sample # | Layer (top, middle, bottom) | Estriol (w/w) | Estradiol (w/w) |
|---|---|---|---|---|
| 28 | 82 | Top | 0.236 | 0.058 |
|  | 83 | Middle | 0.19 | 0.047 |
|  | 84 | Bottom | 0.169 | 0.041 |
| 29 | 85 | Top | 0.247 | 0.064 |
|  | 86 | Middle | 0.164 | 0.043 |
|  | 87 | Bottom | 0.132 | 0.034 |
| 30 | 88 | Top | 0.303 | 0.07 |
|  | 89 | Middle | 0.179 | 0.041 |
|  | 90 | Bottom | 0.141 | 0.033 |

TABLE 46

Results for a composition including 2 API dispersed in EMP 300 mL Jar

| Formulation # | Sample # | Layer (top, middle, bottom) | Estriol (w/w) | Estradiol (w/w) |
|---|---|---|---|---|
| 31 | 91 | Top | 0.213 | 0.055 |
|  | 92 | Middle | 0.207 | 0.053 |
|  | 93 | Bottom | 0.177 | 0.045 |
| 32 | 94 | Top | 0.207 | 0.053 |
|  | 95 | Middle | 0.168 | 0.043 |
|  | 96 | Bottom | 0.17 | 0.044 |

TABLE 46-continued

Results for a composition including 2 API dispersed in EMP 300 mL Jar

| Formulation # | Sample # | Layer (top, middle, bottom) | Estriol (w/w) | Estradiol (w/w) |
|---|---|---|---|---|
| 33 | 97 | Top | 0.204 | 0.056 |
|  | 98 | Middle | 0.203 | 0.055 |
|  | 99 | Bottom | 0.193 | 0.053 |

TABLE 47

Results for a composition including 2 API dispersed in EMP 1 L Jar

| Formulation # | Sample # | Layer (top, middle, bottom) | Estriol (w/w) | Estradiol (w/w) |
|---|---|---|---|---|
| 34 | 100 | Top | 0.183 | 0.044 |
|  | 101 | Middle | 0.184 | 0.044 |
|  | 102 | Bottom | 0.178 | 0.043 |
| 35 | 103 | Top | 0.15 | 0.038 |
|  | 104 | Middle | 0.16 | 0.041 |
|  | 105 | Bottom | 0.16 | 0.041 |
| 36 | 106 | Top | 0.183 | 0.043 |
|  | 107 | Middle | 0.166 | 0.039 |
|  | 108 | Bottom | 0.174 | 0.041 |

TABLE 48

% RSD Results for the compositions of Tables 42 to 47

|  | Estriol | Estradiol |
|---|---|---|
| Formulation | % RSD | |
| 19 | 1.1% | 1.1% |
| 20 | 1.7% | 2.2% |
| 21 | 0.8% | 0.0% |
| 22 | 0.3% | 1.2% |
| 23 | 0.0% | 0.0% |
| 24 | 0.3% | 1.1% |
| 25 | 0.5% | 1.1% |
| 26 | 0.3% | 0.0% |
| 27 | 0.6% | 0.0% |
| 28 | 17.3% | 17.7% |
| 29 | 32.8% | 32.8% |
| 30 | 40.8% | 40.6% |
| 31 | 9.7% | 10.4% |
| 32 | 12.1% | 11.8% |
| 33 | 3.0% | 2.8% |
| 34 | 1.8% | 1.3% |
| 35 | 3.7% | 4.3% |
| 36 | 4.9% | 4.9% |

Other examples of implementations will become apparent to the reader in view of the teachings of the present description and as such, will not be further described here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this disclosure pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

In the present disclosure, each of the variously stated ranges is intended to be continuous so as to include each numerical parameter between the stated minimum and maximum value of each range. For Example, a range of about 1 to about 4 includes: about 1, 1, about 2, 2, about 3, 3, about 4, and 4.

Although various embodiments of the disclosure have been described and illustrated, it will be apparent to those skilled in the art in light of the present description that numerous modifications and variations can be made. The scope of the invention is defined more particularly in the appended claims.

What is claimed is:

1. A dispensing container and adapter system for use with a planetary mixer, the system comprising:
   a dispensing container having a central longitudinal axis and a transverse axis and including:
      a nozzle including an aperture configured to allow contents to exit from the dispensing container;
      a removable cap configured to cover the nozzle, the removable cap having a first external width dimension measured along the transverse axis; and
      a body connected to and spaced apart from the nozzle along the longitudinal axis, the body having a second width dimension to an inner surface of the body as measured along the transverse axis;
   an adapter configured to receive the dispensing container, the adapter including:
      a first wall portion defining a cavity configured to receive the removable cap, the cavity having a cavity width that exceeds the first width dimension; and
      a second wall portion defining a recess configured to receive a portion of the dispensing container, the recess extending from the cavity and at least a portion of the recess having a width dimension measured from the central longitudinal axis along the transverse axis that is smaller than both the first width dimension and the second width dimension; and
   a jar configured to receive the dispensing container and the adapter.

2. The system of claim 1, wherein the adapter includes an opening radially spaced apart from the recess.

3. The system of claim 1, wherein the dispensing container includes an actuator to meter the contents through the nozzle.

4. The system of claim 1, wherein the removable cap is threadably mounted to the nozzle.

5. The system of claim 1, wherein the recess is configured to slidably receive the portion of the dispensing container.

6. The system of claim 1, wherein the adapter includes:
a first adapter portion having a first outer diameter; and
a second adapter portion having a second outer diameter larger than the first outer diameter.

7. The system of claim 1, wherein the recess includes threads.

8. The system of claim 7, wherein the recess is configured to threadably engage with threads on the nozzle.

9. The system of claim 1, wherein the jar, the dispensing container, and the adapter are configured to permit superimposed revolution and rotation movements.

10. The system of claim 9, wherein the superimposed revolution and rotation movements last between 20 and 900 seconds and with a revolution speed of at least 400 revolutions per minute.

11. A container assembly for use with a planetary mixer, the assembly comprising:
a dispensing container having a central longitudinal axis and a transverse axis and including:
  a first container part having a first external width dimension measured along the transverse axis; and
  a second container part connected to the first container part and having a second width dimension to an inner surface of the second container part as measured along the transverse axis;
an adapter configured to receive the dispensing container, the adapter including:
  a first wall portion defining a cavity configured to receive the first container part, the cavity having a cavity width that exceeds the first width dimension; and
  a second wall portion defining a recess configured to support a portion of the second container part, the recess extending from the cavity and the recess having a width dimension measured from the central longitudinal axis along the transverse axis that is smaller than both the first width dimension and the second width dimension; and
a jar configured to receive the dispensing container and the adapter.

12. The container assembly of claim 11, wherein the adapter includes:
a first adapter portion having a first outer diameter; and
a second adapter portion having a second outer diameter different from the first outer diameter.

13. The container assembly of claim 12, wherein the recess extends through the second adapter portion.

14. The container assembly of claim 11, wherein the recess is concentric with the cavity.

15. The container assembly of claim 11, wherein the jar includes a threaded cap.

16. The container assembly of claim 11, wherein the adapter is configured to engage with an inner wall of the jar.

17. The container assembly of claim 11 wherein the jar includes:
a bottom wall; and
an inner wall attached to the bottom wall, the bottom wall and the inner wall defining a chamber configured to receive the adapter.

18. The container assembly of claim 17, wherein a dimension of the chamber increases or decreases along a direction generally perpendicular to the bottom wall.

19. The container assembly of claim 11, wherein the container assembly is configured to permit superimposed revolution and rotation movements.

20. The container assembly of claim 19, wherein the superimposed revolution and rotation movements last between 20 and 900 seconds and with a revolution speed of at least 400 revolutions per minute.

* * * * *